United States Patent [19]

Meinke et al.

[11] Patent Number: 5,962,499
[45] Date of Patent: Oct. 5, 1999

[54] NODULISPORIC ACID DERIVATIVES

[75] Inventors: Peter T. Meinke, New York, N.Y.; Thomas Shih, Edison; Michael H. Fisher, Ringoes, both of N.J.

[73] Assignee: Merck & Co., Inc., Rahway, N.J.

[21] Appl. No.: 09/046,052

[22] Filed: Mar. 23, 1998

Related U.S. Application Data

[63] Continuation of application No. 08/716,012, Sep. 19, 1996, abandoned, and a continuation-in-part of application No. 08/606,312, Mar. 11, 1996, abandoned, which is a continuation-in-part of application No. 08/406,619, Mar. 20, 1995, abandoned.

[51] Int. Cl.$^6$ .................. A61K 31/35; C07D 207/12; C07D 311/94; C07D 405/10
[52] U.S. Cl. .................. 514/410; 514/422; 514/423; 514/428; 514/444; 514/453; 514/461; 548/417; 548/518; 549/356; 549/381; 549/414; 549/472; 549/473; 549/59; 549/60
[58] Field of Search ............... 514/410, 422; 548/417; 549/381, 414

[56] References Cited

U.S. PATENT DOCUMENTS

| 5,399,582 | 3/1995 | Dombrowski et al. | 514/410 |
| 5,595,991 | 1/1997 | Shoop et al. | 514/233.2 |

*Primary Examiner*—Johann Richter
*Assistant Examiner*—Jane C. Oswecki
*Attorney, Agent, or Firm*—Mollie M. Yang; David L. Rose

[57] ABSTRACT

The present invention relates to novel nodulosporic acid derivatives, which are acaricidal, antiparasitic, insecticidal and anthelmintic agents.

31 Claims, No Drawings

NODULISPORIC ACID DERIVATIVES

CROSS REFERENCE

This is a continuation of application Ser. No. 08/716,012 filed Sep. 19, 1996 abandoned.

This is a continuation-in part of application U.S. Ser. No. 08/606,312 filed Mar. 11, 1996, now abandoned, which is a continuation-in-part of U.S. Ser. No. 08/406,619, filed Mar. 20, 1995, now abandoned. The disclosures of the applications are hereby incorporated by reference.

BACKGROUND OF THE INVENTION

Nodulosporic acid and two related components are antiparasitic agents and ectoparasiticidal agents isolated from the fermentation culture of Nodulisporium sp. MF-5954 (ATCC 74245). These three compounds have the following structures:

nodulisporic acid (compound A)

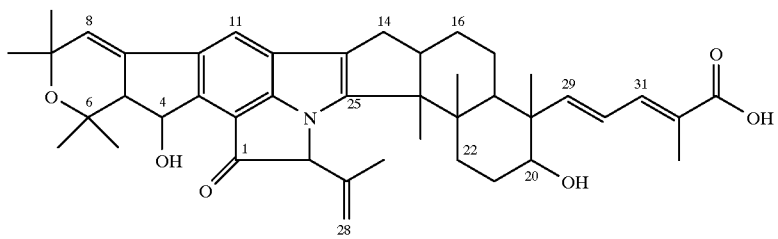

29,30-dihydro-20,30-oxa-nodulisporic acid (compound B)

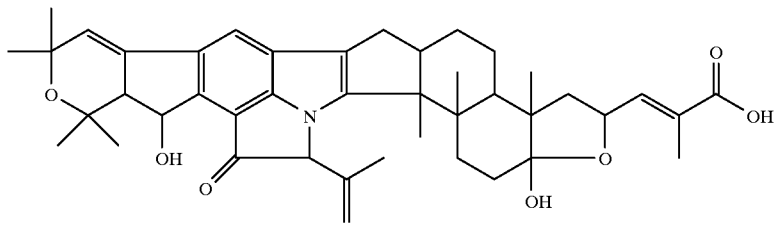

31-hydroxy-20,30-oxa-29,30,31,32-tetrahydro-nodulisporic acid (compound C)

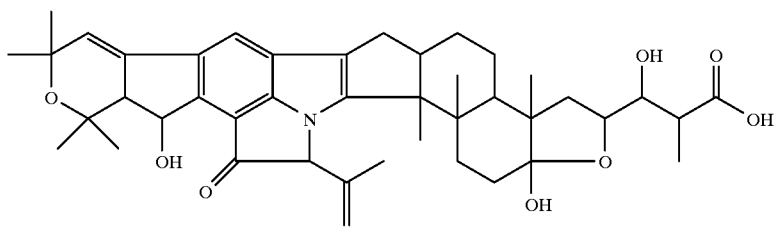

SUMMARY OF THE INVENTION

This invention relates to new acaricidal, antiparasitic, insecticidal and anthelmintic agents related to the nodulisporic acids, to processes for their preparation, compositions thereof, their use in the treatment of parasitic infections, including helminthiasis, in human and animals, and their use in the treatment of parasitic infections in plants or plant products.

DETAILED DESCRIPTION OF THE INVENTION

The present invention provides compounds having the formula I:

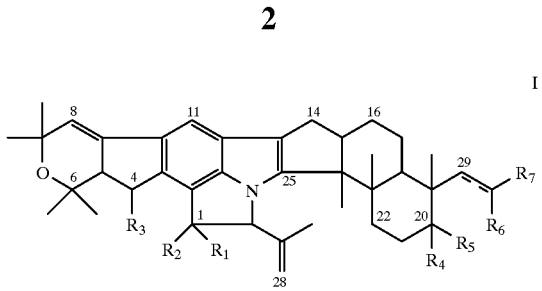

wherein
$R_1$ is (1) hydrogen,
(2) optionally substituted $C_1$–$C_{10}$ alkyl,
(3) optionally substituted $C_2$–$C_{10}$ alkenyl,
(4) optionally substituted $C_2$–$C_{10}$ alkynyl,
(5) optionally substituted $C_3$–$C_8$ cycloalkyl,
(6) optionally substituted $C_5$–$C_8$ cycloalkenyl where the substitutents on the alkyl, alkenyl, alkynyl, cycloalkyl and cycloalkenyl are 1 to 3 groups independently selected from
(i) $C_1$–$C_5$ alkyl,
(ii) X—$C_1$–$C_{10}$ alkyl, where X is O or $S(O)_m$.
(iii) $C_3$–$C_8$ cycloalkyl,
(iv) hydroxy,
(v) halogen,
(vi) cyano,
(vii) carboxy,
(viii) $NY^1Y^2$, where $Y^1$ and $Y^2$ are independently H or $C_1$–$C_{10}$ alkyl,
(ix) $C_1$–$C_{10}$ alkanoylamino, and (x) aroyl amino wherein said aroyl is optionally substituted with 1 to 3 groups independently selected from $R^f$
(7) aryl $C_0$–$C_5$ alkyl wherein said aryl is optionally substituted with 1 to 3 groups independently selected from
(8) $C_1$–$C_5$ perfluoroalkyl
(9) a 5- or 6-membered heterocycle containing from 1 to 4 heteroatoms independently selected from oxygen, sulfur and nitrogen atoms optionally substituted by 1 to 3 groups independently selected from hydroxy, oxo, $C_1$–$C_{10}$ alkyl and halogen, and which may be saturated or partly unsaturated, $R_2$, $R_3$, and $R_4$ are independently $OR^a$; $OCO_2R^b$, $OC(O)NR^cR^d$; or $R_1+R_2$ represent =O, =$NOR^a$ or =N—$NR^cR^d$;
$R_5$ and $R_6$ are H; or
$R_5$ and $R_6$ together represent —O—;
$R_7$ is (1) CHO, or
(2) the fragment

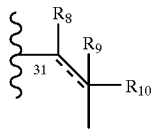

$R_8$ is (1) H,
(2) $OR^a$, or
(3) $NR^cR^d$
$R_9$ is (1) H, or
(2) $OR^a$;
$R_{10}$ is (1) CN,
(2) $C(O)OR^b$,
(3) $C(O)N(OR^b)R^c$,
(4) $C(O)NR^cR^d$,
(5) $NHC(O)OR^b$,
(6) $NHC(O)NR^cR^d$,
(7) $CH_2OR^a$,
(8) $CH_2OCO_2R^b$,
(9) $CH_2OC(O)NR^cR^d$,
(10) $C(O)NR^cNR^cR^d$, or
(11) $C(O)NR^cSO_2R^b$;
---- represents a single or a double bond;
$R^a$ is (1) hydrogen,
(2) optionally substituted $C_1$–$C_{10}$ alkyl,
(3) optionally substituted $C_3$–$C_{10}$ alkenyl,
(4) optionally substituted $C_3$–$C_{10}$ alkynyl,
(5) optionally substituted $C_1$–$C_{10}$ alkanoyl,
(6) optionally substituted $C_3$–$C_{10}$ alkenoyl,
(7) optionally substituted $C_3$–$C_{10}$ alkynoyl,
(8) optionally substituted aroyl,
(9) optionally substituted aryl,
(10) optionally substituted $C_3$–$C_7$ cycloalkanoyl,
(11) optionally substituted $C_5$–$C_7$ cycloalkenoyl,
(12) optionally substituted $C_1$–$C_{10}$ alkylsulfonyl (13) optionally substituted $C_3$–$C_8$ cycloalkyl
(14) optionally substituted $C_5$–$C_8$ cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, $C_1$–$C_6$ alkoxy, $C_3$–$C_7$ cycloalkyl, aryl $C_1$–$C_3$ alkoxy, $NR^gR^h$, $CO_2R^b$, $CONR^cR^d$ and halogen,
(15) $C_1$–$C_5$ perfluoroalkyl,
(16) arylsulfonyl optionally substituted with 1 to 3 groups independently selected from $C_1$–$C_5$ alkyl, $C_1$–$C_5$ perfluoroalkyl, nitro, halogen and cyano,
(17) a 5- or 6-membered heterocycle containing 1 to 4 heteroatoms selected from oxygen, sulfur and nitrogen optionally substituted by 1 to 4 groups independently selected from $C_1$–$C_5$ alkyl, $C_1$–$C_5$ alkenyl, $C_1$–$C_5$ perfluoroalkyl, amino, $C(O)NR^cR^d$, cyano, $CO_2R^b$ and halogen, and which may be saturated or partly unsaturated;

$R^b$ is (1) H,
(2) optionally substituted aryl,
(3) optionally substituted $C_1$–$C_{10}$ alkyl,
(4) optionally substituted $C_3$–$C_{10}$ alkenyl,
(5) optionally substituted $C_3$–$C_{10}$ alkynyl,
(6) optionally substituted $C_3$–$C_{15}$ cycloalkyl,
(7) optionally substituted $C_5$–$C_{10}$ cycloalkenyl, or
(8) optionally substituted 5- to 10-membered heterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from
(i) hydroxy,
(ii) $C_1$–$C_6$ alkyl,
(iii) oxo,
(iv) $SO_2NR^gR^h$,
(v) aryl $C_1$–$C_6$ alkoxy,
(vi) hydroxy $C_1$–$C_6$ alkyl,
(vii) $C_1$–$C_{12}$ alkoxy,
(viii) hydroxy $C_1$–$C_6$ alkoxy,
(ix) amino $C_1$–$C_6$ alkoxy,
(x) cyano,
(xi) mercapto,
(xii) $C_1$–$C_6$ alkyl-S(O)m,
(xiii) $C_3$–$C_7$ cycloalkyl optionally substituted with 1 to 4 groups independently selected from $R^e$,
(xiv) $C_5$–$C_7$ cycloalkenyl,
(xv) halogen,
(xvi) $C_1$–$C_5$ alkanoyloxy,
(xvii) $C(O)NR^gR^h$,
(xviii) $CO_2R^i$,
(xix) formyl,
(xx) —$NR^gR^h$,
(xxi) 5 to 9-membered heterocycle, which may be saturated or partially unsaturated, containing from 1 to 4 heteroatoms independently selected from oxygen, sulfur and nitrogen, and optionally substituted with 1 to 5 groups independently selected from $R^e$,
(xxii) optionally substituted aryl, wherein the aryl substituents are 1,2-methylenedioxy or 1 to 5 groups independently selected from $R^e$,
(xxiii) optionally substituted aryl $C_1$–$C_3$ alkoxy, wherein the aryl substituents are 1,2-methylenedioxy or 1 to 5 groups independently selected from $R^e$, and
(xxiv) $C_1$–$C_5$ perfluoroalkyl;

$R^c$ and $R^d$ are independently selected from $R^b$; or
$R^c$ and $R^d$ together with the N to which they are attached form a 3- to 10-membered ring containing 0 to 2 additional heteroatoms selected from O, $S(O)_m$, and N, optionally substituted with 1 to 3 groups independently selected from $R^g$, hydroxy, thioxo and oxo;

$R^e$ is (1) halogen,
(2) $C_1$–$C_7$ alkyl,
(3) $C_1$–$C_3$ perfluoroalkyl,
(4) —$S(O)_m R^i$,
(5) cyano,
(6) nitro,
(7) $R^i O(CH_2)_v$—,
(8) $R^i CO_2(CH_2)_v$—,
(9) $R^i OCO(CH_2)_v$,
(10) optionally substituted aryl where the substituents are from 1 to 3 of halogen, $C_1$–$C_6$ alkyl, $C_1$–$C_6$ alkoxy, or hydroxy,
(11) $SO_2 NR^g R^h$, or
(12) amino;

$R^f$ is (1) $C_1$–$C_4$ alkyl,
(2) X—$C_1$–$C_4$ alkyl, where X is O or $S(O)_m$,
(3) $C_2$–$C_4$ alkenyl,
(4) $C_2$–$C_4$ alkynyl,
(5) $C_1$–$C_3$-perfluoroalkyl,
(6) $NY^1 Y^2$, where $Y^1$ and $Y^2$ are independently H or $C_1$–$C_5$ alkyl,
(7) hydroxy,
(8) halogen, and
(9) $C_1$–$C_5$ alkanoyl amino, $R^g$ and $R^h$ are independently
(1) hydrogen,
(2) $C_1$–$C_6$ alkyl optionally substituted with hydroxy, amino, or $CO_2 R^i$
(3) aryl optionally substituted with halogen, 1,2-methylenedioxy, $C_1$–$C_7$ alkoxy, $C_1$–$C_7$ alkyl or $C_1$–$C_3$ perfluoroalkyl,
(4) aryl $C_1$–$C_6$ alkyl, wherein the aryl is optionally substituted with $C_1$–$C_3$ perfluorolkyl or 1,2-methylenedioxy;
(5) $C_1$–$C_5$ alkoxycarbonyl,
(6) $C_1$–$C_5$ alkanoyl,
(7) $C_1$–$C_5$ alkanoyl $C_1$–$C_6$ alkyl,
(9) aryl $C_1$–$C_5$ alkoxycarbonyl,
(10) aminocarbonyl,
(11) $C_1$–$C_5$ monoalkylaminocarbonyl
(12) $C_1$–$C_5$ dialkylaminocarbonyl; or $R^g$ and $R^h$ together with the N to which they are attached form a 3- to 7-membered ring containing 0 to 2 additional heteroatoms selected from O, $S(O)_m$, and N, optionally substituted with 1 to 3 groups independently selected from $R^e$ and oxo;

$R^i$ is (1) hydrogen,
(2) $C_1$–$C_3$ perfluoroalkyl,
(3) $C_1$–$C_6$ alkyl,
(4) optionally substituted aryl $C_0$–$C_6$ alkyl, where the aryl substituents are from 1 to 3 groups independently selected from halogen, $C_1$–$C_6$ alkyl, $C_1$–$C_6$ alkoxy, and hydroxy;

m is 0 to 2; and
v is 0 to 3; or
a pharmaceutically acceptable salt thereof; and excluding nodulisporic acid, 29,30-dihydro-20,30-oxa-nodulisporic acid, and 31-hydroxy-20,30-oxa-29,30,31,32-tetrahydro-nodulisporic acid.

In a preferred embodiment, the present invention provides compounds of Formula I wherein $R_1$ is (1) hydrogen,
(2) optionally substituted $C_1$–$C_6$ alkyl,
(3) optionally substituted $C_2$–$C_6$ alkenyl,
(4) optionally substituted $C_2$–$C_6$ alkynyl,
(5) optionally substituted $C_5$–$C_6$ cycloalkyl,
(6) optionally substituted $C_5$–$C_6$ cycloalkenyl where the substitutents on the alkyl, alkenyl, alkynyl, cycloalkyl and cycloalkenyl are 1 to 3 groups independently selected from
 (i) $C_1$–$C_3$ alkyl,
 (ii) X—$C_1$–$C_6$ alkyl, where X is O or $S(O)_m$,
 (iii) $C_5$–$C_6$ cycloalkyl,
 (iv) hydroxy,
 (v) halogen,
 (vi) cyano,
 (vii) carboxy, and
 (viii) $NY^1 Y^2$, where $Y^1$ and $Y^2$ are independently H or $C_1$–$C_6$ alkyl,
(7) aryl $C_0$–$C_3$ alkyl wherein said aryl is optionally substituted with 1 to 3 groups independently selected from $R^f$,
(8) $C_1$–$C_3$ perfluoroalkyl,
(9) a 5- or 6-membered heterocycle containing from 1 to 4 heteroatoms independently selected from oxygen, sulfur and nitrogen atoms optionally substituted by 1 to 3 groups independently selected from hydroxy, oxo, $C_1$–$C_6$ alkyl and halogen, and which may be saturated or partly unsaturated, $R^8$ is (1) H,
(2) OH, or
(3) $NH_2$;

$R_9$ is (1) H or
(2) OH;

$R^{10}$ is (1) $C(O)OR^b$,
(2) $C(O)N(OR^b)R^c$,
(3) $C(O)NR^c Rd$,
(4) $NHC(O)OR^b$,
(5) $NHC(O)NR^c R^d$,
(6) $CH_2 OR^a$,
(7) $CH_2 OCO_2 R^b$,
(8) $CH_2 OC(O)NR^c R^d$,
(9) $C(O)NR^c NR^c R^d$, or
(10) $C(O)NR^c SO_2 R^b$;

$R^a$ is (1) hydrogen,
(2) optionally substituted $C_1$–$C_6$ alkyl,
(3) optionally substituted $C_3$–$C_6$ alkenyl,
(4) optionally substituted $C_3$–$C_6$ alkynyl,
(5) optionally substituted $C_1$–$C_6$ alkanoyl,
(6) optionally substituted $C_3$–$C_6$ alkenoyl,
(7) optionally substituted $C_3$–$C_6$ alkynoyl,
(8) optionally substituted aroyl,
(9) optionally substituted aryl,
(10) optionally substituted $C_5$–$C_6$ cycloalkanoyl,
(11) optionally substituted $C_5$–$C_6$ cycloalkenoyl,
(12) optionally substituted $C_1$–$C_6$ alkylsulfonyl
(13) optionally substituted $C_5$–$C_6$ cycloalkyl
(14) optionally substituted $C_5$–$C_6$ cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, $C_1$–$C_4$ alkoxy, $C_5$–$C_6$ cycloalkyl, aryl $C_1$–$C_3$ alkoxy, $NR^gR^h$, $CO_2R^b$, $CONR^cR^d$ and halogen,
(15) $C_1$–$C_3$ perfluoroalkyl,
(16) arylsulfonyl optionally substituted with 1 to 3 groups independently selected from $C_1$–$C_3$ alkyl, $C_1$–$C_3$ perfluoroalkyl, halogen and cyano,
(17) a 5- or 6-membered heterocycle containing 1 to 4 heteroatoms selected from oxygen, sulfur and nitrogen optionally substituted by 1 to 4 groups independently selected from $C_1$–$C_3$ alkyl, $C_1$–$C_3$ alkenyl, $C_1$–$C_3$ perfluoroalkyl, amino, $C(O)NR^cR^d$, cyano, $CO_2R^b$ and halogen, and which may be saturated or partly unsaturated;

$R^b$ is (1) H,
(2) optionally substituted aryl,
(3) optionally substituted $C_1$–$C_7$ alkyl,
(4) optionally substituted $C_3$–$C_7$ alkenyl,
(5) optionally substituted $C_3$–$C_7$ alkynyl,
(6) optionally substituted $C_5$–$C_7$ cycloalkyl,
(7) optionally substituted $C_5$–$C_7$ cycloalkenyl, or
(8) optionally substituted 5- to 10-membered heterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from
  (i) hydroxy,
  (ii) $C_1$–$C_3$ alkyl,
  (iii) oxo,
  (iv) $SO_2NR^gR^h$,
  (v) aryl $C_1$–$C_3$ alkoxy,
  (vi) hydroxy $C_1$–$C_3$ alkyl,
  (vii) $C_1$–$C_7$ alkoxy,
  (viii) hydroxy $C_1$–$C_3$ alkoxy,
  (ix) amino $C_1$–$C_3$ alkoxy,
  (x) cyano,
  (xi) $C_1$–$C_3$ perfluoroalkyl,
  (xii) $C_1$–$C_3$ alkyl-S(O)m,
  (xiii) $C_5$–$C_6$ cycloalkyl optionally substituted with 1 to 4 groups independently selected from $R^e$,
  (xiv) $C_5$–$C_6$ cycloalkenyl,
  (xv) halogen,
  (xvi) $C_1$–$C_3$ alkanoyloxy,
  (xvii) $C(O)NR^gR^h$,
  (xviii) $CO_2R^i$,
  (xix) optionally substituted aryl $C_1$–$C_3$ alkoxy, wherein the aryl substituents are 1,2-methylenedioxy or 1 to 5 groups independently selected from $R^e$,
  (xx) —$NR^gR^h$,
  (xxi) 5 to 6-membered heterocycle, which may be saturated or partially unsaturated, containing from 1 to 4 heteroatoms independently selected from oxygen, sulfur and nitrogen, and optionally substituted with 1 to 5 groups independently selected from $R^e$, and
  (xxii) optionally substituted aryl, wherein the aryl substituents are 1,2-methylenedioxy or 1 to 5 groups independently selected from $R^e$;

$R^e$ is (1) halogen,
(2) $C_1$–$C_3$ alkyl,
(3) $C_1$–$C_3$ perfluoroalkyl,
(4) —$S(O)_mR^i$,
(5) cyano,
(6) amino,
(7) $R^iO(CH_2)_v$—,
(8) $R^iCO_2(CH_2)_v$—,
(9) $R^iOCO(CH_2)_v$,
(10) optionally substituted aryl where the substituents are from 1 to 3 of halogen, $C_1$–$C_3$ alkyl, $C_1$–$C_3$ alkoxy, or hydroxy, or
(11) $SO_2NR^gR^h$;

$R^f$ is (1) methyl,
(2) X—$C_1$–$C_2$ alkyl, where X is O or $S(O)_m$,
(3) halogen,
(4) acetylamino,
(5) trifluoromethyl,
(6) $NY^1Y^2$, where $Y^1$ and $Y^2$ are independently H or methyl, and
(7) hydroxy;

$R^g$ and $R^h$ are independently
(1) hydrogen,
(2) $C_1$–$C_6$ alkyl optionally substituted with hydroxy, amino, or $CO_2R^i$
(3) aryl optionally substituted with halogen, 1,2-methylenedioxy, $C_1$–$C_7$ alkoxy, $C_1$–$C_7$ alkyl or $C_1$–$C_3$ perfluoroalkyl,
(4) aryl $C_1$–$C_6$ alkyl, wherein the aryl is optionally substituted with $C_1$–$C_3$ perfluorolkyl or 1,2-methylenedioxy;
(5) $C_1$–$C_5$ alkoxycarbonyl,
(6) $C_1$–$C_5$ alkanoyl,
(7) $C_1$–$C_5$ alkanoyl $C_1$–$C_6$ alkyl,
(9) aryl $C_1$–$C_5$ alkoxycarbonyl,
(10) aminocarbonyl,
(11) $C_1$–$C_5$ monoalkylaminocarbonyl
(12) $C_1$–$C_5$ dialkylaminocarbonyl; or $R^g$ and $R^h$ together with the N to which they are attached form a 5- to 6-membered ring containing 0 to 2 additional heteroatoms selected from O, $S(O)_m$, and N, optionally substituted with 1 to 3 groups independently selected from $R^e$ and oxo;

$R^i$ is (1) hydrogen,
(2) $C_1$–$C_3$ perfluoroalkyl,
(3) $C_1$–$C_4$ alkyl,
(4) optionally substituted aryl $C_0$–$C_4$ alkyl, where the aryl substituents are from 1 to 3 groups independently selected from halogen, $C_1$–$C_4$ alkyl, $C_1$–$C_4$ alkoxy, and hydroxy;

all other variables are as defined under Formula I.

In another preferred embodiment, the present invention provides compounds of Formula I wherein
$R_1$ is (1) hydrogen,
(2) optionally substituted $C_1$–$C_3$ alkyl,
(3) optionally substituted $C_2$–$C_3$ alkenyl,
(4) optionally substituted $C_2$–$C_3$ alkynyl, where the substitutents on the alkyl, alkenyl, and alkynyl are 1 to 3 groups independently selected from
  (i) methyl,
  (ii) X-methyl, where X is O or $S(O)_m$ and
  (iii) halogen,
(5) aryl $C_0$–$C_1$ alkyl wherein said aryl is optionally substituted with 1 to 3 groups independently selected from $R^f$, (6) trifluoromethyl $R_8$ is (1) H,
(2) OH, or
(3) $NH_2$ $R_9$ is (1) H, or
(2) OH;

$R_{10}$ is (1) $C(O)OR^b$,
(2) $C(O)N(OR^b)R^c$,
(3) $C(O)NR^cR^d$,
(4) $NHC(O)OR^b$,
(5) $NHC(O)NR^cR^d$,
(6) $CH_2OR^a$,
(7) $CH_2OCO_2R^b$,
(8) $CH_2OC(O)NR^cR^d$,
(9) $C(O)NR^cNR^cR^d$, or
(10) $C(O)NR^cSO_2R^b$;

$R^a$ is (1) hydrogen,
(2) optionally substituted $C_1$–$C_4$ alkyl,
(3) optionally substituted $C_3$–$C_4$ alkenyl,
(4) optionally substituted $C_3$–$C_4$ alkynyl,
(5) optionally substituted $C_1$–$C_4$ alkanoyl,
(6) optionally substituted aroyl,
(7) optionally substituted $C_5$–$C_6$ cycloalkanoyl,
(8) optionally substituted $C_5$–$C_6$ cycloalkenoyl,
(9) optionally substituted $C_1$–$C_3$ alkylsulfonyl where the substituents on the alkyl, alkenyl, alkynyl, alkanoyl, aroyl, cycloalkanoyl, cycloalkenoyl, and alkylsulfonyl, are from 1 to 5 groups independently selected from hydroxy, $C_1$–$C_2$ alkoxy, aryl $C_1$–$C_3$ alkoxy, $NR^gR^h$, $CO_2R^b$, $CONR^cR^d$ and halogen,
(10) trifluoromethyl,
(11) arylsulfonyl optionally substituted with 1 to 3 groups independently selected from methyl, trifluoromethyl and halogen,
(12) a 5- or 6-membered heterocycle containing 1 to 4 heteroatoms selected from oxygen, sulfur and nitrogen optionally substituted by 1 to 4 groups independently selected from methyl, trifluoromethyl, $C(O)NR^cR^d$, $CO_2R^b$ and halogen, and which may be saturated or partly unsaturated;

$R^b$ is (1) H,
(2) optionally substituted aryl,
(3) optionally substituted $C_1$–$C_6$ alkyl,
(4) optionally substituted $C_3$–$C_6$ alkenyl,
(5) optionally substituted $C_3$–$C_6$ alkynyl,
(6) optionally substituted $C_5$–$C_6$ cycloalkyl,
(7) optionally substituted $C_5$–$C_6$ cycloalkenyl, or
(8) optionally substituted 5- to 6-membered heterocycle containing from 1 to 4 heteroatoms independently selected from oxygen, sulfur and nitrogen; where the substituents on the aryl,. alkyl, alkenyl, cycloalkyl, cycloalkenyl, heterocycle, or alkynyl are from 1 to 10 groups independently selected from
(i) hydroxy,
(ii) $C_1$–$C_3$ alkyl,
(iii) oxo,
(iv) $SO_2NR^gR^h$,
(v) aryl $C_1$–$C_3$ alkoxy,
(vi) hydroxy $C_1$–$C_4$ alkyl,
(vii) $C_1$–$C_4$ alkoxy,
(viii) hydroxy $C_1$–$C_4$ alkoxy,
(ix) amino $C_1$–$C_4$- alkoxy,
(x) cyano,
(xi) $C_1$–$C_4$ alkyl-S(O)m,
(xii) $C_5$–$C_6$ cycloalkyl optionally substituted with 1 to 4 groups independently selected from $R^e$,
(xiii) $C_5$–$C_6$ cycloalkenyl,
(xiv) halogen,
(xv) $C_1$–$C_3$ alkanoyloxy,
(xvi) $C(O)NR^gR^h$,
(xvii) $CO_2R^i$,
(xvii) —$NR^gR^h$,
(xix) 5 to 6-membered heterocycle, which may be saturated or partially unsaturated, containing from 1 to 4 heteroatoms independently selected from oxygen, sulfur and nitrogen, and optionally substituted with 1 to 5 groups independently selected from $R^e$,
(xx) optionally substituted aryl, wherein the aryl substituents are 1,2-methylenedioxy or 1 to 5 groups independently selected from $R^e$,
(xxi) optionally substituted aryl $C_1$–$C_3$ alkoxy, wherein the aryl substituents are 1,2-methylenedioxy or 1 to 5 groups independently selected from $R^e$, and
(xxii) $C_1$–$C_3$ perfluoroalkyl;

$R^e$ is (1) halogen,
(2) $C_1$–$C_3$ alkyl,
(3) $C_1$–$C_3$ perfluoroalkyl,
(4) —$S(O)_mR^i$,
(5) cyano,
(6) $R^iO(CH_2)_v$—,
(7) $R^iCO_2(CH_2)_v$—,
(8) $R^iOCO(CH_2)_v$,
(9) optionally substituted aryl where the substituents are from 1 to 3 of halogen, $C_1$–$C_3$ alkyl, $C_1$–$C_3$ alkoxy, or hydroxy,
(10) $SO_2NR^gR^h$, or
(11) amino;

$R^f$ is (1) methyl,
(2) X—$C_1$–$C_2$ alkyl, where X is O or $S(O)_m$,
(3) trifluoromethyl,
(4) $NY^1Y^2$, where $Y^1$ and $Y^2$ are independently H or methyl,
(5) hydroxy,
(6) halogen, and
(7) acetylamino, $R^g$ and $R^h$ are independently
(1) hydrogen,
(2) $C_1$–$C_6$ alkyl optionally substituted with hydroxy, amino, or $CO_2R^i$
(3) aryl optionally substituted with halogen, 1,2-methylenedioxy, $C_1$–$C_7$ alkoxy, $C_1$–$C_7$ alkyl or $C_1$–$C_3$ perfluoroalkyl,
(4) aryl $C_1$–$C_6$ alkyl, wherein the aryl is optionally substituted with $C_1$–$C_3$ perfluorolkyl or 1,2-methylenedioxy;
(5) $C_1$–$C_5$ alkoxycarbonyl,
(6) $C_1$–$C_5$ alkanoyl,
(7) $C_1$–$C_5$ alkanoyl $C_1$–$C_6$ alkyl,
(9) aryl $C_1$–$C_5$ alkoxycarbonyl,
(10) aminocarbonyl,
(11) $C_1$–$C_5$ monoalkylaminocarbonyl
(12) $C_1$–$C_5$ dialkylaminocarbonyl; or
$R^g$ and $R^h$ together with the N to which they are attached form a 5- to 6-membered ring containing 0 to 2 additional heteroatoms selected from O, S(O)$_m$, and N, optionally substituted with 1 to 3 groups independently selected from R$^e$ and oxo;

R$^i$ is (1) hydrogen,
(2) C$_1$–C$_3$ perfluoroalkyl,
(3) C$_1$–C$_4$ alkyl,
(4) optionally substituted aryl C$_0$–C$_6$ alkyl, where the aryl substituents are from 1 to 3 groups independently selected from halogen, C$_1$–C$_6$ alkyl, C$_1$–C$_6$ alkoxy, and hydroxy; and all other variables are as defined under Formula I.

In another aspect of the present invention there are provided compounds having the formula X

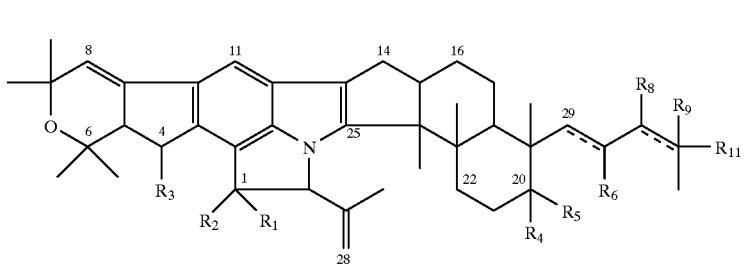

X where R$_1$–R$_6$, R$_8$ and R$_9$ are as defined under formula I; and
R$_{11}$ is (1) COCl,
(2) CON$_3$, or
(3) NCO.

Compounds of formula X are useful as intermediates in the preparation of certain compounds of formula I from Compounds A, B and C.

The present invention provides in another aspect pharmaceutical compositions comprising a compound of Formula I and a pharmaceutically acceptable carrier. Such compositions may further comprise one or more other active ingredients such as anthelmintic agents, insect regulators, ecdosyne agonists and fipronil.

The present invention provides in another aspect a method for treating parasitic diseases in a mammal which comprises administering an antiparasitic amount of a compound of Formula I. The treatment may further comprise co-administering one or more other active ingredients such as anthelmintic agents, insect regulators, ecdosyne agonists and fipronil.

"Alkyl" as well as other groups having the prefix "alk", such as alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as benzofused carbocycles. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "halogen" is intended to include the halogen atoms fluorine, chlorine, bromine and iodine.

The term "heterocycle", unless otherwise specfied, means mono- or bicyclic compounds that are saturated or partly unsaturated, as well as benzo- or heteroaromatic ring fused saturated heterocycles or partly unsaturated heterocycles, and containing from 1 to 4 heteroatoms independently selected from oxygen, sulfur and nitrogen. Examples of saturated heterocycles include morpholine, thiomorpholine, piperidine, piperazine, tetrahydropyran, tetrahydrofuran, dioxane, tetrahydrothiophene, oxazolidine, pyrrolidine; examples of partly unsaturated heterocycles include dihydropyran, dihydropyridazine, dihydrofuran, dihydrooxazole, dihydropyrazole, dihydropyridine, dihydropyridazine and the like. Examples of benzo- or heteroaromatic ring fused heterocycle include 2,3-dihydrobenzofuranyl, benzopyranyl, tetrahydroquinoline, tetrahydroisoquinoline, benzomorpholinyl, 1,4-benzodioxanyl, 2,3-dihydrofuro(2,3-b)pyridyl and the like.

The term "aryl" is intended to include mono- and bicyclic aromatic and heteroaromatic rings containing from 0 to 5 heteroatoms independently selected from nitrogen, oxygen and sulfur. The term "aryl" is also meant to include benzofused cycloalkyl, benzofused cycloalkenyl, and benzofused heterocyclic groups. Examples of "aryl" groups include phenyl, pyrrolyl, isoxazolyl, pyrazinyl, pyridinyl, oxazolyl, thiazolyl, imidazolyl, triazolyl, tetrazolyl, furanyl, triazinyl, thienyl, pyrimidinyl, pyridazinyl, pyrazinyl, naphthyl, benzoxazolyl, benzothiazolyl, benzimidazolyl, benzofuranyl, furo(2,3-B)pyridyl, 2,3-dihydrofuro(2,3-b) pyridyl, benzoxazinyl, benzothiophenyl, quinolinyl, indolyl, 2,3-dihydrobenzofuranyl, benzopyranyl, 1,4-benzodioxanyl, indanyl, indenyl, fluorenyl, 1,2,3,4-tetrahydronaphthalene and the like.

Aroyl means arylcarbonyl in which aryl is as defined above.

Examples of NR$^c$R$^d$ or NR$^g$R$^h$ forming a 3- to 10-membered ring containing 0 to 2 additional heteroatoms selected from 0, S(O)$_m$ and N are aziridine, azetidine, pyrrolidine, piperidine, thiomorpholine, morpholine, piperazine, octahydroindole, tetrahydroisoquinoline and the like.

The term "optionally substituted" is intended to include both substituted and unsubstituted; thus, for example, optionally substituted aryl could represent a pentafluorophenyl or a phenyl ring.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

Accordingly, the pharmaceutical compositions of the present invention encompass any composition made by admixing a compound of the present invention and a pharmaceutically acceptable carrier.

Certain of the above defined terms may occur more than once in the above formula and upon such occurrence each term shall be defined independently of the other; thus, for example, $OR^a$ at C4 may represent OH and at C20 represent O-acyl.

Compounds described herein contain one or more asymmetric centers and may thus give rise to diastereomers and optical isomers. The present invention is intended to include all possible diastereomers as well as their racemic and resolved, enantiomerically pure forms and all possible geometric isomers. In addition, the present invention includes all pharmaceutically acceptable salts thereof. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Compounds of the present invention are named based on the trivial name of the parent compound, nodulisporic acid (compound A), and their position numbers are those as indicated in formula I.

Compounds of the present invention are prepared from the three nodulisporic acids (Compounds A, B and C), which in turn are obtained from the fermentation culture of Nodulisporium sp. MF-5954 (ATCC 74245). The description of the producing microorganism, the fermentation process, and the isolation and purification of the three nodulisporic acids are disclosed in U.S. Pat. No. 5,399,582, issued Mar. 21, 1995, which is hereby incorporated by reference in its entirety.

The above structural formula is shown without a definitive stereochemistry at certain positions. However, during the the course of the synthetic procedures used to prepare such compounds, or using racemization or epimerization procedures known to those skilled in the art, the products of such procedures can be a mixture of stereoisomers. In particular, the stereoisomers at C1, C4, C20, C26, C31 and C32 may be oriented in either the alpha- or beta-position, representing such groups oriented below or above the plane of the molecule, respectively. In each such case, and at other positions in the molecule, both the alpha- and beta-configurations are intended to be included within the ambit of this invention.

Compounds of formula I wherein the allyl group at position 26 is in the epi configuration may be obtained by treatment of the appropriate precursor with a bases such as hydroxide, methoxide, imidazole, triethylamine, potassium hydride, lithium diisopropylamide and the like in protic or aprotic solvents (as appropriate) such as water, methanol, ethanol, methylene chloride, chloroform, tetrahydrofuran, dimethylformamide and the like. The reaction is complete at temperatures from −78° C. to the reflux temperature of the solution in from 15 minutes to 12 hours.

Compounds of formula I where $R_2$ (and $R_1$ is hydrogen), $R_3$, $R_4$ and $R_8$ independently are hydroxy may be inverted by treatment of the appropriate alcohol using protocols known to those skilled in the art. For example, the alcohol may be reacted under Mitsunobu conditions with a carboxylic acid (formic acid, propionic acid, 2-chloroacetic acid, benzoic acid, para-nitro-benzoic acid and the like), a tri-substituted phosphine (triphenylphosphine, tri-n-butylphoshine, tripropylphosphine and the like) and a dialkyl diazodicarboxylate (diethyl diazodicarboxylate, dimethyl diazodicarboxylate, diisopropyl diazodicarboxylate and the like) in an aprotic solvent such as methylene chloride, tetrahydrofuran, chloroform, benzene and the like. The Mitsunobu reactions are complete in from 1 to 24 hours at temperatures from 0° C. to the reflux temperature of the solution. The resultant esters may be hydrolyzed by treatment with hydroxide or ammonium hydroxide in a protic solvent such as methanol, ethanol, water, tetrahydrofuran/water or dimethylformamide/water and the like at from 0° C. to the reflux temperature of the solution. Alternatively, the resultant esters may be hydrolyzed by treatment with a Lewis acid, such as, magnesium chloride, aluminum chloride, titanium tetra-isopropoxide and the like in a protic solvent such as methanol, ethanol, isopropanol and the like and the reactions are complete in from 1 to 24 hours at 0° C. to the reflux temperature of the solution.

During certain reactions described below, it may be necessary to protect the groups at $R_2$, $R_3$, $R_4$, $R_8$, $R_9$ and $R_{10}$. With these positions protected, the reactions may be carried out at other positions without affecting the remainder of the molecule. Subsequent to any of the described reactions (vida infra), the protecting group(s) may be removed and the unprotected product isolated. The protecting groups employed at $R_2$, $R_3$, $R_4$, $R_8$, $R_9$ and $R_{10}$ are those which may be readily synthesized, not significantly affected by the reactions at the other positions, and may be removed without significantly affecting any other functionality of the molecule. One preferred type of protecting group is the tri-substituted silyl group, preferably the tri-loweralkyl silyl group or di-loweralkyl-aryl silyl group. Especially preferred examples are the trimethylsilyl, triethylsilyl, triisopropylsilyl, tert-butyldimethylsilyl and dimethylphenylsilyl groups.

The protected compound may be prepared with the appropriately substituted silyl trifluoromethanesulfonate or silyl halide, preferably the silyl chloride. The reaction is carried out in an aprotic solvent such as methylene chloride, benzene, toluene, ethyl acetate, isopropyl acetate, tetrahydrofuran, dimethylformamide and the like. In order to minimize side reactions, there is included in the reaction mixture a base to react with the acid released during the course of the reaction. Preferred bases are amines such as imidazole, pyridine, triethylamine or diisopropylethylamine and the like. The base is required in amounts equimolar to the amount of hydrogen halide liberated, however, generally several equivalents of the amine are employed. The reaction is stirred at from 0° C. to the reflux temperature of the reaction mixture and is complete from 1 to 24 hours.

The silyl group is removed by treatment of the silyl compound with anhydrous pyridine-hydrogen fluoride in tetrahydrofuran or dimethylsulfoxide or with tetraalkylammonium fluoride in tetrahydrofuran. The reaction is complete in from 1 to 24 hours at from 0° C. to 50° C. Alternatively, the silyl group may be removed by stirring the silylated compound in lower protic solvents such as methanol, ethanol, isopropanol and the like catalyzed by an acid, preferably a sulfonic acid monohydrate such as para-toluenesulfonic acid, benzenesulfonic acid or carboxylic acids such as acetic acid, propionic acid, monochloroacetic acid, dichloroacetic acid, trichloroacetic acid and the like. The reaction is complete in 1 to 24 hours at from 0° C. to 50° C.

Protecting groups that may also be suitably used in the preparation of compounds of the present invention may be found in standard textbooks such as Greene and Wutz, *Protective Groups in Organic Synthesis,* 1991, John Wiley & Sons, Inc.

Compounds of formula I where $R_1$ and $R_2$ together represent an oxime, $=NOR^a$, may be prepared by treating the appropriate oxo analog with $H_2NOR^a$ to produce the corresponding oxime. Oxime formation may be accomplished using techniques known to those skilled in the art, including, but not restricted to, the use of $H_2NOR^a$ either as the free base or as an acid addition salt such as the HCl salt, or an O-protected hydroxylamine such as O-trialkylsilylhydroxylamine, in a protic solvent such as methanol, ethanol, isopropanol and the like or aprotic solvents such as methylene chloride, chloroform, ethyl acetate, isopropyl acetate, tetrahydrofuran, dimethylformamide, benzene, toluene and the like, as appropriate. The reactions may by catalyzed by the addition of sulfonic acids, carboxylic acids or Lewis acids, including, but not limited to, benzenesulfonic acid monhydrate, para-toluenesulfonic acid monohydrate, acetic acid, zinc chloride and the like.

Similarly, compounds of formula I wherein $R_1$ and $R_2$ together represent $=NNR^cR^d$ may be prepared by treating the appropriate oxo analog with $H_2NNR^cR^d$ to give the corresponding hydrazones using conditions directly analogous to those described for oxime formation.

Compounds of formula I wherein one or both of the ---- bonds represent a single bond may be prepared from the corresponding compound wherein ---- is a double bond by conventional hydrogenation procedures. The double bonds may be hydrogenated with any of a variety of standard precious metal hydrogenation catalysts such as Wilkinson's catalyst, Pearlman's catalyst, 1–25% palladium on carbon, 1–25% platinum on carbon and the like. The reaction is generally carried out in a non-reducible solvents (either protic or aprotic) such as methanol, ethanol, isopropanol, tetrahydrofuran, ethyl acetate, isopropyl acetate, benzene, toluene, dimethylformamide and the like. The hydrogen source may be hydrogen gas from 1 to 50 atmospheres of pressure or other hydrogen sources such as ammonium formate, cyclohexene, cyclohexadiene and the like. The reduction also may be carried out using sodium dithionite and sodium bicarbonate in the presence of a phase transfer catalyst, in particular a tetraalkylammonium phase transfer catalyst, and the like. The reactions may be run from 0° C. to 100° C. and are complete in from 5 min to 24 hours.

Compounds of formula I wherein $R_8$ and $R_9$ are both hydroxyl groups may be prepared according to the procedure shown in Scheme I.

SCHEME I

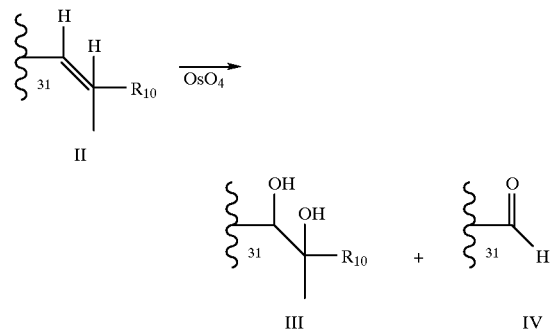

Thus, Compound II is treated with osmium tetroxide under conditions known to those skilled in the art to yield the diol product III. Also produced during this reaction is the aldehyde IV. Osmium tetroxide may be used either stoichiometrically or catalytically in the presence of an oxidant, including, but not restricted to, morpholine N-oxide, trimethylamine N-oxide, hydrogen peroxide, tert-butyl hydroperoxide and the like. The dihydroxylation reactions may be performed in a variety of solvents or mixtures of solvents. These include both protic and aprotic solvents such as water, methanol, ethanol, tert-butanol, ether, tetrahydrofuran, benzene, pyridine, acetone and the like. The reactions may be performed at from –78° C. to 80° C. and are complete in from 5 minutes to 24 hours.

Compounds of formula I wherein $R_8$ is $NR^cR^d$ and $R_9$ is hydrogen may be prepared by treatment of the appropriate precursor containing the C31–C32 unsaturation with $HNR^cR^d$ or $HCl.HNR^cR^d$ in an appropriate protic or aprotic solvents such as methanol, ethanol, benzene, toluene, dimethylformamide, dioxane, water and the like. The reaction may be facilitated by the addition of bases such as pyridine, triethylamine, sodium carbonate and the like or Lewis acids such as zinc chloride, magnesium chloride and the like. The reactions are complete in from 1 to 24 hours at temperatures from 0° C. to the reflux temperature of the solution.

Compounds of formula I wherein $R_2$ is OH and $R_1$ is H may be prepared from the corresponding ketone by treating the appropriate oxo analog with standard reducing agents including, but not restricted to, sodium borohydride, lithium borohydride, lithium aluminum hydride, potassium tri-sec-butyl borohydride, diisobutylaluminum hydride, diborane oxazaborolidines and alkylboranes (both achiral and chiral). These reactions are performed in a manner known to those skilled in the art and are carried out in non-reducible solvents such as methanol, ethanol, diethyl ether, tetrahydrofuran, hexanes, pentane, methylene chloride and the like. The reactions are complete in from 5 minutes to 24 hours at temperatures ranging from.–78° C. to 60° C. Compounds of formula I wherein $R_2$ is OH, $R_1$ is H and $R_{10}$ is $CH_2OH$ may be obtained by reacting the appropriate carboxylic acid or ester analog (e.g., where $R_{10}$ is $CO_2H$ or $CO_2R^a$) with the more reactive reducing agents as described above, including lithium aluminum hydride, lithium borohydride and the like. Compounds of formula I wherein $R_2$ and $R_1$ together are oxo and $R_{10}$ is $CH_2OH$ may be obtained by reacting the appropriate carboxylic acid (e.g., where $R_{10}$ is $CO_2H$) with less reactive reducing agents such as diborane and the like.

Compounds of formula I wherein $R_2$ is OH and $R^1$ is other than H, may be prepared from the corresponding ketone by treating the appropriate oxo analog with a Grignard reagent $R_1MgBr$, or with a lithium reagent $R_1Li$. These reactions are performed in a manner known to those skilled in the art and preferably are performed in aprotic solvents such as diethyl ether, tetrahydrofuran, hexanes or pentanes. The reactions are complete in from 5 minutes to 24 hours at temperatures ranging from −78° C. to 60° C.

Compounds of formula I where $R_{10}$ is $C(O)N(OR^b)R^c$ or $C(O)NR^cR^d$ are prepared from the corresponding carboxylic acid using standard amide-forming reagents known to those skilled in the art. The reaction is carried out using at least one equivalent of an amine nucleophile, $HN(OR^b)R^c$ or $HNR^cR^d$, although preferably ten to one hundred equivalents of amine nucleophiles are employed. Amide-forming reagents include, but are not restricted to, dicyclohexylcarbodiimide, 1-(3-dimethylaminopropyl)-3-ethylcarbodiimide hydrochloride (EDC.HCl), diisopropylcarbodiimide, benzotriazol-1-yloxy-tris (dimethylamino)phosphonium hexafluorphosphate (BOP), bis(2-oxo-3-oxazolidinyl)phosphinic chloride (BOP-Cl), benzotriazole-1-yl-oxy-tris-pyrrolidino-phosphonium hexafluorophosphate (PyBOP), chloro-tris-pyrrolidino-phosphonium hexafluorophosphate (PyCloP), bromo-tris-pyrrolidino-phosphonium hexafluorophosphate (PyBroP), diphenylphosphoryl azide (DPPA), 2-(1H-benzotriazole-1-yl)-1,1,3,3-tetramethyluronium hexafluorophosphate (HBTU), O-benzotriazol-1-yl-N,N,N',N'-bis (pentamethylene)uronium hexafluorophosphate and 2-chloro-1-methylpyridinium iodide. The amide-forming reactions may be facilitated by the optional addition of N-hydroxybenzotriazole or N-hydroxy-7-aza-benzotriazole. The amidation reaction is generally performed using at least one equivalent (although several equivalents may be employed) of amine bases such as triethylamine, diisopropylethylamine, pyridine, N,N-dimethylaminopyridine and the like. The carboxyl group may be activated for amide bond formation via its corresponding acid chloride or mixed anhydride, using conditions known to those skilled in the art. These amide-forming reactions are carried out in aprotic solvents such as methylene chloride, tetrahydrofuran, diethyl ether, dimethylformamide, N-methylpyrrolidine and the like at −20° C. to 60° C. and are complete in 15 minutes to 24 hours.

Compounds of formula I where $R_{10}$ is cyano may be prepared by treatment of the appropriate carboxamide with dehydrating reagents known to those skilled in the art such as para-toluenesulfonyl chloride, methanesulfonyl chloride, acetyl chloride, thionyl chloride, phosphorus oxychloride or catecholboron chloride in an aprotic solvent such as methylene chloride, chloroform, tetrahydrofuran, benzene, toluene and the like. The reactions are complete in from 15 minutes to 24 hours at temperatures from −78° C. to the reflux temperature of the solution.

Compounds of formula I where $R_{10}$ is $C(O)OR^b$ are prepared from the corresponding carboxylic acid using standard ester-forming reagents known to those skilled in the art. The esterification reaction is carried out using at least one equivalent of an alcohol, $HOR^b$, although preferably ten to one hundred equivalents of alcohol are used; the esterification also may be carried out using the alcohol as solvent. Esterification reagents include, but are not restricted to, dicyclohexylcarbodiimide, 1-(3-dimethylaminopropyl)-3-ethylcarbodiimide hydrochloride (EDC.HCl), diisopropylcarbodlimide, benzotriazol-1-yloxy-tris (dimethylamino)phosphonium hexafluorphosphate (BOP), bis(2-oxo-3-oxazolidinyl)phosphinic chloride (BOP-Cl), benzotriazole-1-yl-oxy-tris-pyrrolidino-phosphonium hexafluorophosphate (PyBOP), chloro-tris-pyrrolidino-phosphonium hexafluorophosphate (PyCloP), bromo-tris-pyrrolidino-phosphonium hexafluorophosphate (PyBroP), diphenylphosphoryl azide (DPPA), 2-(1H-benzotriazole-1-yl)-1,1,3,3-tetramethyluronium hexafluorophosphate (HBTU), O-benzotriazol-1-yl-N,N,N',N'-bis (pentamethylene)uronium hexafluorophosphate and 2-chloro-1-methylpyridinium iodide. The ester-forming reactions may be facilitated by the optional addition of N-hydroxybenzotriazole, N-hydroxy-7-aza-benzotriazole, 4-(N,N-dimethylamino)pyridine or 4-pyrrolidinopyridine. The reaction is generally performed using at least one equivalent (although several equivalents may be employed) of amine bases such as triethylamine, diisopropylethylamine, pyridine and the like. The carboxyl group may be activated for ester bond formation via its corresponding acid chloride or mixed anhydride, using conditions known to those skilled in the art. These ester-forming reactions are carried out in aprotic solvents such as methylene chloride, tetrahydrofuran, diethyl ether, dimethylformamide, N-methylpyrrolidine and the like at temperatures ranging from −20° C. to 60° C. and are complete in 15 minutes to 24 hours.

Compounds of formula I wherein one or more of $R_2$, $R_3$, $R_4$, $R_8$ and $R_9$ is $OR^a$, $OCO_2R^b$ or $OC(O)NR^cR^d$, and/or where $R_{10}$ is $CH_2OR^a$, $CH_2OCO_2R^b$ or $CH_2OC(O)NR^cR^d$ may be prepared using known methods for acylation, sulfonylation and alkylation of alcohols. Thus, acylation may be accomplished using reagents such as acid anhydrides, acid chlorides, chloroformates, carbamoyl chlorides, isocyanates and amine bases according to general procedures known to those skilled in the art. Sulfonylations may be carried out using sulfonylchlorides or sulfonic anhydrides. The acylation and sulfonylation reactions may be carried out in aprotic solvents such as methylene chloride, chloroform, pyridine, benzene, toluene and the like. The acylation and sulfonylation reactions are complete in from 15 minutes to 24 hours at temperatures ranging from −20° C. to 80° C. The degree of acylation, sulfonylation and alkylation will depend on the amount of the reagents used. Thus, for example, using one equivalent of an acylating reagent and one equivalent of nodulisporic acid results in a product mixture containg 4- and 20-acylated nodulisporic acid; such a mixture may be separated by conventional techniques such as chromatography.

Compounds of formula I wherein one or more of $R_2$, $R_3$, $R_4$, $R_8$ and $R_9$ is $OR^a$ and/or where $R_{10}$ is $CH_2OR^a$, may be prepared using methods known to those skilled in the art for the alkylation of alcohols. Thus, alkylation may be accomplished using reagents including, but not restricted to, halides $IR^a$, $BrR^a$, $ClR^a$, diazo reagents $N_2R^a$, trichloroacetimidates $R^aOC(NH)CCl_3$, sulfates $R^aOSO_2Me$, $R^aOSO_2CF_3$, and the like. The alkylation reactions may be facilitated by the addition of acid, base or Lewis acids, as appropriate. The reactions are performed in aprotic solvents such as methylene chloride, chloroform, tetrahydrofuran, benzene, toluene, dimethylformamide, N-methylpyrrolidine, dimethyl sulfoxide, hexamethylphosphoramide and are complete at from 0° C. to the reflux temperature of the solution from 15 minutes to 48 hours.

Compounds of formula I where $R^iO$ is $NHC(O)OR^b$ or $C(O)NR^cR^d$ are prepared from the corresponding carboxylic acid via the corresponding acyl azide (VI) and isocyanate (VII) as shown in Scheme

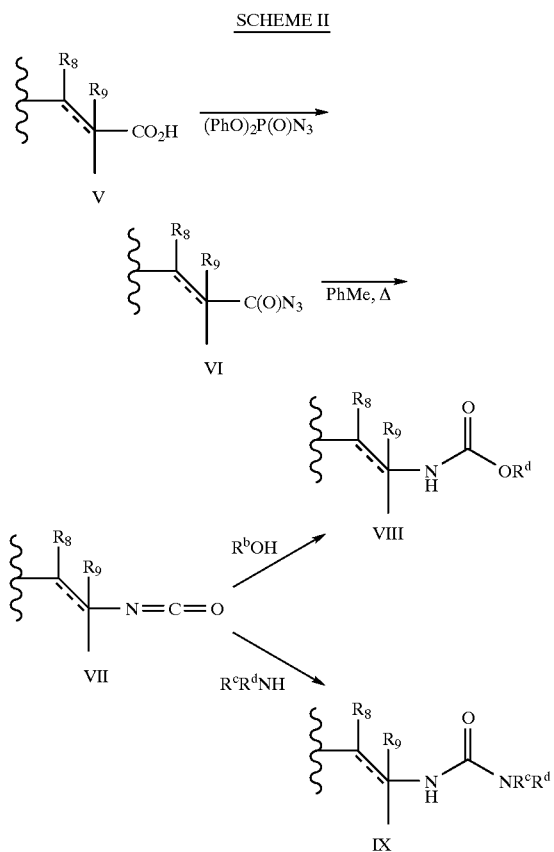

SCHEME II

In Scheme II, $R_8$, $R_9$, $R^b$, $R^c$, $R^d$ and ---- have the same meaning as defined under formula I. Thus, the carboxylic acid (compound V) is treated with diphenylphosphoryl azide to provide the acyl azide (compound VI). Heating of compound VI in an aprotic solvent such as benzene, toluene, dimethylformamide and the like results in a rearrangement yielding compound VII, an isocyanate. Compound VII may be reacted in an aprotic solvent such as benzene, toluene, methylene chloride, 1,2-dichloroethylene, dimethylformamide and the like, with an alcohol $R^bOH$, such as methanol, ethanol, benzyl alcohol, 2-trimethylsilylethanol, 2,2,2-trichloroethanol, methyl glycocolate, phenol and the like to yield compound VIII, a carbamate. The addition of one or more equivalents of an amine base such as triethylamine, diisopropylethylamine, pyridine and the like may be employed to accelerate carbamate formation. The carbamate-forming reactions may be performed from 0° C. to 100° C. and are complete in 15 minutes to 24 hours.

Compounds of formula IX may be prepared when compounds of formula VII are reacted with an appropriate amine $HNR^cR^d$ in an aprotic solvent such as methylene chloride, tetrahydrofuran, dimethylformamide, dimethylsulfoxide, benzene, toluene and the like. The urea-forming reactions may be performed from 0° C. to 100° C. and are complete in 15 minutes to 24 hours.

The instant compounds are potent endo- and ecto-antiparasitic agents, particularly against helminths, ectoparasites, insects, and acarids, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the hehminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoyma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have activity against these parasites, and in addition are also active against Dirofilaria in dogs and cats, Nematospiroides, Syphacia, Aspiculuris in rodents, arthropod ectoparasites of animals and birds such as ticks, mites such as scabies lice, fleas, blowflies, and other biting insects in domesticated animals and poultry, such as Tenophalides, Ixodes, Psoroptes, and Hemotobia, in sheep Lucilia sp., biting insects and such migrating dipterous larvae as Hypoderma sp. in cattle, Gastrophilus in horses, and Cuterebra sp. in rodents and nuisance flies including blood feeding flies and filth flies.

The instant compounds are also useful against parasites which infect humans. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acreage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

Accordingly, the present invention provides a method for the treatment or prevention of diseases caused by parasites which comprises administering to a host in need of such treatment or prevention an antiparasitic effective amount of a compound of Formula I. The parasites may be, for example, arthropod parasites such as ticks, lice, fleas, mites and other biting arthropods in domesticated animals and poultry. The parasites also include helminths such as those mentioned above.

Compounds of formula I are effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 500 mg per kg of animal body weight, such total dose being given at one time or in divided doses over a relatively short period of time such as 1–5 days. With the preferred compounds of the invention, excellent control of such parasites is obtained in animals by administering from about 0.025 to 100 mg per kg of body weight in a single dose. Repeat treatments are given as required to combat re-infections and are dependent upon the species of parasite and the husbandry techniques being employed. Repeat treatments may be given daily, weekly, biweekly, monthly, or longer for example up to six months, or any combination thereof, as required. The techniques for administering these materials to animals are known to those skilled in the veterinary field.

Compounds of formula I may be co-administered or used in combination with one or more other agents to the host. Co-administration or combination use includes administering all active ingredients in one formulation, for example a tablet, capsule, feed stuff, or liquid containing a compound of formula I and one or more said other agents; administering each ingredient in a separate formulation; and combinations thereof. When one or more of a compound of formula I or said other agent(s) is contained in a separate formulation, any order of administration as well as any interval between the administration of the active ingredients are within the meaning of co-administration or combination use.

Agents that may be co-administered or used in combination with compounds of formula I include any that are used in the treatment or prevention of human or animal diseases or conditions, or used in agricultural applications, or for pest control. In a preferred embodiment, the co-administered agents are used in veterinary medicine, particularly those used in domesticated animals such as dogs and cats or other companion animals. Examples of other agents that may be co-administered with compounds of formula I are provided below. It is to be understood that the specific agents enumerated are illustrative only, and are not meant to be restrictive in any manner.

Accordingly, compounds of the present invention may be co-administered or used in combination with anthelmintic agents. These anthelmintic agents are meant to include, but not be restricted to, compounds selected from the avermectin and milbemycin class of compounds such as ivermectin, avermectin, abamectin, emamectin, eprinamectin, doramectin, milbemycin derivatives described in EPO 357460, EPO 444964 and EPO 594291, moxidectin, milbemycin oxime ("INTERCEPTOR™") and nemadectin. Additional anthelmintic agents include the benzimidazoles such as thiabendazole, cambendazole, parbendazole, oxibendazole, mebendazole, flubendazole, fenbendazole, oxfendazole, albendazole, cyclobendazole, febantel, thiophanate and the like. Additional anthelmintic agents include imidazothiazoles and tetrahydropyrimidines such as tetramisole-levamisole, butamisole, pyrantel, pamoate, oxantel or morantel.

Compounds of this invention may be co-administered or used in combination with fipronil FRONTLINE™, or with an insect growth regulator with molt inhibiting activity such as lufenuron PROGRAM™ and the like; or with ecdysone agonists such as tebufenozide and the like, which induces premature molt and causes feeding to cease; or with imidacloprid ADVANTAGE™.

Compounds of this invention may be co-administered or used in combination with avermectin or milbemycin or doramectin derivatives such as those described in U.S. Pat. No. 5,015,630, WO 94/15944, WO95/22552.

Compounds of this invention may be co-administered or used in combination with cyclic depsipeptides that exhibit anthelmintic efficacy such as those described in WO96/11945, WO93/19053, WO 93/25543, EP 626375, EP 382173, WO 94/19334, EP 382173 and EP 503538.

Compounds of this invention may be used in combination or be co-administered with derivatives and analogs of the general class of dioxomorpholine antiparasitic and anthelmintic agents as illustrated by WO 9615121; or with pyrethroids or organophosphates or insecticidal carbamates, such as those described in "Chemotherapy of Parasitic Diseases", Campbell, W. C. and Rew, R. S, Eds., 1986; or with derivatives and analogs of the general class of paraherquamide and macfortine anthelmintic agents.

The co-administered compounds are given via routes, and in doses, that are customarily used for those compounds.

Compounds of formula I may be administered orally in a unit dosage form such as a capsule, bolus or tablet including chewable tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for 'such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 50% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 10% in the feed in order to achieve the desired anti-parasitic result.

In using the compounds of this invention, the individual compounds may be prepared and used in that form. Alternatively, mixtures of the individual compounds may be used, or they may be combined with other active compounds not related to the compounds of this invention.

Also included in the present invention are pharmaceutical compositions comprising a compound of formula I and a pharmaceutically acceptable carrier. The pharmaceutical compositions of the present invention may further comprise a second active ingredient such as those described above for co-administration. Preferred second ingredient is selected from an anthelmintic agent, fipronil, imidocloprid, an insect growth regulator, or a ecdysone agonist. Said second ingredient is preferably selected from the group consisting of: ivermectin, avermectin 5-oxime, abamectin, emamectin, eprinamectin, doramectin, doramectin monosaccharide 5-oximes, fulladectin, milbemycin, milbemycin 5-oxime, moxidectin, INTERCEPTOR™, nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

The following examples are provided to more fully illustrate the present invention, and shall not be construed as limiting the scope in any manner.

EXAMPLE 1

Methyl nodulisporate

To 5.4 mg nodulisporic acid in 5 mL methanol at room temperature was added 0.5 mL 10% trimethylsilyldiazomethane in hexanes. After 15 minutes, three drops of glacial acetic acid was added and the solution diluted with benzene, frozen and lyophilized. Pure methyl ester was obtained following reversed-phase HPLC purification using 85:15 methanol:water as eluant and the product was characterized by $^1$H NMR and mass spectrometry.

EXAMPLE 2

Methyl 29,30-dihydro-20,30-oxa-nodulisporate

To 0.8 mg Compound B in 1 mL methanol at room temperature was added 0.2 mL 1 M trimethylsilyldiazomethane in hexanes. After 5 minutes, 0.1 mL glacial acetic acid was added, the solution stirred for three minutes and the 2 mL saturated NaHCO$_3$ was added (foaming occurred). The solution was extracted with ethyl acetate, dried with Na$_2$SO$_4$, filtered and concentrated in vacuo. The crude was purifed by reversed-phase HPLC using 15:85 water/methanol as eluant and the purified product was characterized by $^1$H NMR.

EXAMPLE 3

Methyl 31-hydroxy-20,30-oxa-29,30,31,32-tetrahydronodulisporate

To 1 mg Compound C in 1 mL methanol at room temperature was added 0.2 mL 1 M trimethylsilyldiazomethane in hexanes. After 5 minutes, 0.1 mL glacial acetic acid was added, the solution stirred for three minutes and the 2 mL saturated NaHCO$_3$ was added (foaming occurred). The solution was extracted with ethyl acetate, dried with Na$_2$SO$_4$, filtered and concentrated in vacuo. The crude was purifed by reversed-phase HPLC using 17.5:82.5 water/methanol as eluant and the purified product was characterized by $^1$H NMR.

EXAMPLE 4

Ethyl nodulisporate

To a solution containing 20 mg nodulisporic acid in 2 mL methylene chloride at room temperature was added 0.11 mL ethanol, 0.008 mL diisopropylethylamine, 1 mg N,N-dimethylaminopyridine (DMAP) followed by 13 mg BOP reagent. After 50 hours at room temperature, the solution was poured into 1/1 saturated sodium bicarbonate/brine and extracted with methylene chloride. The combined organic layers were dried over sodium sulfate, the solids were removed by filtration and the solution concentrated under reduced pressure. Pure product was obtained following preparative TLC on silica gel (one 1000 micron plate) using ⅓ acetone/hexanes as eluant. Purified product (15 mg) was characterized by proton NMR and mass spectrometry (m/z: 708.4 (M+1)).

The general procedure of Example 4 was repeated using the alcohols listed in Table 1 below to provide the corresponding nodulisporate derivatives. These compounds were characterized by proton NMR and/or mass spectrometry (m/z is for (M+1) unless otherwise specified).

TABLE 1

Ester Derivatives of Nodulisporic Acid

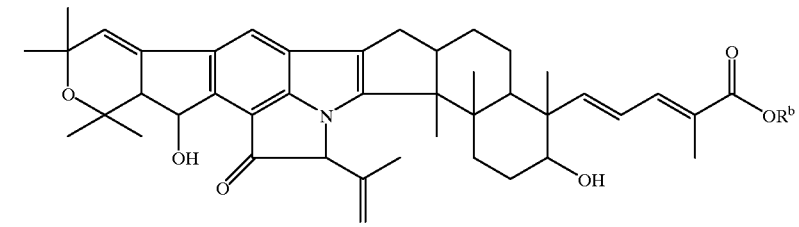

| Ex. | m/z | Alcohol | R$^b$ |
|---|---|---|---|
| 5 | 797.6 | N-Hydroxybenzotriazole | (benzotriazole structure) |
| 6 | 724.4 | 2-Hydroxyethanol | CH$_2$CH$_2$OH |
| 7 | 807.5 | 2-(Diisopropylamino)-ethanol | CH$_2$CH$_2$N(CH(CH$_3$)$_2$)$_2$ |
| 8 | 738.4 | 3-Hydroxypropanol | CH$_2$CH$_2$CH$_2$OH |
| 9 | 752.3 | 4-Hydroxybutanol | CH$_2$CH$_2$CH$_2$CH$_2$OH |
| 10 | 767.0 | 5-Hydroxypentanol | CH$_2$CH$_2$CH$_2$CH$_2$CH$_2$OH |
| 11 | 751.5 | 2-Dimethylaminoethanol | CH$_2$CH$_2$N(CH$_3$)$_2$ |
| 12 | 837.7 | 3-Diisopropylamino-2-hydroxypropanol | CH$_2$CH(OH)CH$_2$N(CH(CH$_3$)$_2$)$_2$ |
| 13 | 768.9 | 2-(2-Hydroxyethoxy)-ethanol | CH$_2$CH$_2$OCH$_2$CH$_2$OH |
| 14 | 815.4 | 4-Nitrobenzyl alcohol | CH$_2$Ph(4-NO$_2$) |
| 15 | 815.4 | 3-Nitrobenzyl alcohol | CH$_2$Ph(3-NO$_2$) |
| 16 | 807.7 | 2-Hydroxy-3-(1-pyrrolidinyl)propanol | CH$_2$CH(OH)C(H$_2$)—N(pyrrolidine) |
| 17 | 793.7 | 4-(2-Hydroxyethyl)-morpholine | CH$_2$CH$_2$—N(morpholine) |
| 18 | 762.4 | 2,2,2-Trifluoroethanol | CH$_2$CF$_3$ |
| 19 | | 2-(Hydroxymethyl)furan | CH$_2$-(furan) |
| 20 | 764.5 | 5-Hydroxypentan-2-one | CH$_2$CH$_2$CH$_2$C(=O)CH$_3$ |

TABLE 1-continued

Ester Derivatives of Nodulisporic Acid

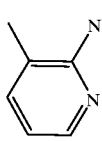

| Ex. | m/z | Alcohol | R$^b$ |
|---|---|---|---|
| 21 | | 3-Phenylpropanol | CH$_2$CH$_2$CH$_2$Ph |
| 22 | 764.3 | 3,3-Dimethylbutanol | CH$_2$CH$_2$C(CH$_3$)$_2$CH$_3$ |
| 23 | | 2-(N-Acetylamino)-3-hydroxypyridine | 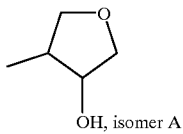 |
| 24 | 766.7 | 3,4-Dihydroxytetrahydrofuran, Isomer A | 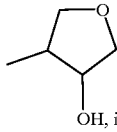 OH, isomer A |
| 25 | 766.6 | 3,4-Dihydroxytetrahydrofuran, Isomer B | OH, isomer B |
| 26 | 831.5 | 1,1,1,3,3,3-hexafluoro-isopropanol | CH(CF$_3$)$_2$ |
| 27 | | 2-(Trifluoromethyl)benzyl alcohol | CH$_2$Ph(2-CF$_3$) |

EXAMPLE 28

General Procedure for the Preparation of Additional Ester Derivatives of Compounds A, B and C To a solution containing 20 mg Compound A, B or C in 2 mL methylene chloride at room temperature add 110 mg of an alcohol selected from Table 2, 0.008 mL diisopropylethylamine and 1 mg DMAP followed by 13 mg BOP reagent. After from 1 hour to 3 days at room temperature, pour the solution into 1/1 saturated sodium bicarbonate/brine and extract with methylene chloride. The combined organic layers may be dried over sodium sulfate and the solids may be removed by filtration. Concentrate the solution under reduced pressure. Pure product may be obtained following flash chromatography or preparative TLC on silica gel or reversed-phase liquid chromatography. Purified product may be characterized by proton NMR and/or mass spectrometry.

Table 2: Alcohols for the Preparation of Additional Ester Derivatives of Compounds A, B and C 3-(Methylthio)propanol, 1H,1H-Pentafluoropropanol, 2-Pentyn-1-ol, 3-Pentyne-1-ol, 4-Pentyne-1-ol, Propanol, 2-Hydroxyethanol, Methyl glycolate, Glycolic acid, 4-(Methoxy)benzyl alcohol, 3-(Dimethylamino)propanol, 3-(4-Morpholinyl)propanol, 2-(Hydroxymethyl)pyridine, 1-(2-Hydroxyethyl)piperazine, 2-Hydroxy-3-phenylpropanol, 2-(Hydroxyethoxy)ethanol, 4-(2-Hydroxyethyl)morpholine, 1-(2-Hydroxyethyl)piperidine, 3-(Hydroxymethyl)pyridine, 1-(Hydroxymethyl)pyrimidine, 3-Hydroxypropanol, 4-Hydroxybutanol, 1-(2-Hydroxyethyl)-4-methylpiperazine, 2-(2-Hydroxyethyl)pyridine, 1-(3-Hydroxypropyl)-2-pyrrolidinone, 1-(2-Hydroxyethyl)pyrrolidine, 1-(3-Hydroxypropyl)imidazole, 2-Hydroxybutanol, 4-(Hydroxymethyl)pyridine, 2-Hydroxypyrazine, Hydroxyacetonitrile, 6-Hydroxyhexanol, 4-(3-Hydroxypropyl)morpholine, 2-Hydroxypropanol, 2-Hydroxypentanol, 1-Hydroxy-1-(hydroxymethyl)cyclopentane, 2-(Methylthio)ethanol, 3-Hydroxy-1,2,4-triazine, 2-Amino-3-hydroxypyridine, 2-(Ethylthio)ethanol, Glycolamide, 2-Hydroxy-2-(hydroxymethyl)propanol, trans-2-Hydroxycyclohexanol, 2-Hydroxyl-4-methylphenol, 2-(Hydroxymethyl)pyridine, 1-Hydroxymethyl-1-cyclohexanol, 2-Hydroxyhexanol, 2-Hydroxy-1-methoxypropane, 2-(Hydroxymethyl) imidazole, 3-Hydroxymethylpyrazole, trans-4-Hydroxycyclohexanol, N-Acetyl-4-hydroxybutylamine, Hydroxycyclopentane, 2-(Methylsulfonyl)ethanol, 2-(Methylsulfinyl)ethanol, 4-(2-Hydroxyethyl)phenol, 2-(2-Hydroxyethyl)phenol, 2-Hydroxy-3-methylbutanol, 3-(N-Acetylamino)propanol, 3-(Diethylamino)propanol, 3-(Dimethylamino)propanol, Allyl alcohol, 2-(Dimethylamino)ethanol, Glycerol, 2-Methoxyethanol, 2-(N-Acetylamino)ethanol, D-(Hydroxymethyl)pyrrolidine, 3-Hydroxypyrrolidine, 2-(Hydroxyethyl)benzene, 2-Hydroxyethyl-1-methylpyrrolidine, 2-Hydroxy-2-methyl-propanol, Cyclopropanol, Cyclohexanol, 3-Hydroxypropanol, 3-Ethoxypropanol, Propargyl alcohol, Ethyl glycolate, 2-Fluoroethanol, 3-(Dodecyloxy)propanol, 4-Hydroxybutanol, 5-Hydroxypentanol, 2-(Dimethylamino) ethanol, 2-(2-Hydroxyethoxy)ethanol, 1-(2-Hydroxyethyl) imidazolone, 2-(2-Hydroxyethoxy)ethylamine, Isopropanol, 2,2,2-Trifluoroethanol, 4-Nitrobenzyl alcohol, 3-Nitrobenzyl alcohol, 2-Methoxyethanol, 4-(Hydroxyethyl)phenol, 4-(3-Hydroxypropyl)-1-sulfonamidobenzene, D,L-2-(Hydroxymethyl) tetrahydrofuran, Methyl lactate, 5-Hydroxyhexanoic acid, methyl ester, 3-Methoxypropanol, 3-Hydroxypiperidine, Pentanol, 4-Hydroxyheptane, 4-(2-Hydroxyethyl)-1,2-dimethoxybenzene, 4-Hydroxymethyl-1,2-methylenedioxybenzene, 4-(Trifluoromethyl)benzyl alcohol, 4-(Methylthio)pheno, 2-(Hydroxymethyl)furan, 5-Hydroxypentan-2-one, 2-Hydroxy-3-methylbutanoic acid, methyl ester, 2-Hydroxy-3-phenyl-propanoic acid, ethyl ester, 1-(Hydroxymethyl)napthalene, 3-Phenylpropanol, 3,3-Dimethylbutanol, 3-(2-Hydroxyethyl)fluorobenzene, 4-Hydroxy-1-carboethoxypiperidine, (R)-2-(Hydroxymethyl)tetrahydrofuran, (S)-2-(Hydroxymethyl) tetrahydrofuran, (S)-2-Hydroxy-3-methylbutanol, (R)-2-Hydroxy-3-methylbutanol, (S)-2-Hydroxy-propanol, 3,4-Dihydroxytetrahydrofuran, 1,1,1,3,3,3-hexfluoroisopropanol, 2-Fluorobenzyl alcohol, tert-Butanol, 2-Hydroxy-1-phenylethanol, iso-Butanol, 4-(2-Hydroxyethyl)fluorobenzene, 3-(Hydroxymethyl)toluene, 2–Chlorobenzyl alcohol, 2,4-Dichorobenzyl alcohol, sec-Butanol, R-2-Hydroxypropanol, Butanol, 4–Chlorobenzyl alcohol, 2-Ethoxyethanol, 2-(2-Hydroxyethyl) chlorobenzene, 2-(N-Methyl-N-phenylamino)ethanol, 3-(Trifluoromethyl)benzyl alcohol, 2-(Trifluoromethyl) benzyl alcohol, 2-(Hydroxyethyl)tetrahydrofuran, 4-Phenylbutanol, Nonyl alcohol, 2,6-Difluorobenzyl alcohol, 2-(Hydroxymethyl)thiophene, 2-(Hydroxyethyl)-1-methylpyrrole, 2-Hydroxy-3-methylbutane, 4-Hydroxymethyl-1,2-dichlorobenzene, 3-(Methylamino) propanol, 1,4-Difluorobenzyl alcohol, (2-Hydroxymethyl) furan,

EXAMPLE 29

N-Methyl nodulisporamide and 26-epi-N-methyl nodulisporamide

To 1 mg nodulisporic acid in 1 mL dimethylformamide at room temperature was added 2 mg HCl.H$_2$NMe, 2 mg N-hydroxybenzotriazole and 10 μL diisopropylethylamine to which was added 2 mg EDC.HCl. After 30 minutes, the reaction was quenched by addition of methanol and 1 drop glacial acetic acid. The solution was diluted with brine, extracted with ethyl acetate, dried with Na$_2$SO$_4$, filtered and concentrated under reduced pressure. The reaction was partially purified by preparative TLC (1×0.5 mm silica gel plate) using 6:3:1 EtOAc/acetone/methanol. N-Methyl nodulisporamide and 26-epi-N-methyl nodulisporamide were purified to homogeniety by reversed-phase HPLC using a 60 minute linear gradient from 25:75 to 100:0 acetonitrile/ water. The purified products were characterized by $^1$H NMR and mass spectrometry.

EXAMPLE 30

N-(n-Propyl)-nodulisporamide

To 0.5 mg nodulisporic acid in 1 mL methylene chloride at room temperature was added 2 drops diisopropylethylamine, 5 mg H$_2$NCH$_2$CH$_2$CH$_3$, 3 mg N-hydroxylbenzotriazole and 3 mg PyBOP. After 30 minutes at room temperature, the reaction was quenched with 2 mL saturated NaHCO$_3$, extracted with ethyl acetate, dried (Na$_2$SO$_4$), filtered and concentrated in vacuo. The crude was partially purified by silica gel flash chromatography using 0.5:5:95 NH$_4$OH/MeOH/CHCl$_3$ as eluant followed by reversed-phase HPLC purification using 20:80 water/ methanol as eluant. The product was characterized by $^1$H NMR.

EXAMPLE 31

4-Morpholinyl-nodulisporamide

To 1.5 mg nodulisporic acid in 1 mL methylene chloride at room temperature was added 1 drop diisopropylethylamine, 1 drop morpholine and 2 mg N-hydroxybenzotriazole. 2 mg pyBOP was then added. After 1 hour at room temperature, the solution was filtered through 2 inches silica gel in a pipet without workup using ethyl acetate as eluant. The resultant solution was concentrated under reduced pressure and pure product was obtained following reversed-phase HPLC using 20:80 water/MeOH as eluant. The product was characterized by $^1$H NMR.

EXAMPLE 32

N-(2-Hydroxyethyl)-nodulisporamide

To 0.5 mg nodulisporic acid in 1 mL methylene chloride at room temperature was added 2 drops diisopropylethylamine, 5 mg H$_2$NCH$_2$CH$_2$OH, 3 mg N-hydroxybenzotriazole and 3 mg PyBOP. After 30 minutes, the reaction was quenched with 2 mL saturated NaHCO$_3$, extracted with ethyl acetate, dried (Na$_2$SO$_4$), filtered and concentrated in vacuo. The crude was purified by reversed-phase HPLC using 20:80 water/methanol as eluant and the product was characterized by $^1$H NMR and mass spectrometry.

EXAMPLE 33

N-(1-Methoxycarbonyl-2-hydroxyethyl)-nodulisporamide

To 1.5 mg nodulisporic acid in 1 mL methylene chloride at room temperature was added 2 drops diisopropylethylamine, 5 mg HCl.H$_2$NCH(CH$_2$OH) CO$_2$Me, 3 mg N-hydroxybenzotriazole and 3 mg PyBOP. After 30 minutes, the reaction was quenched with 2 mL saturated NaHCO$_3$, extracted with ethyl acetate, dried (Na$_2$SO$_4$), filtered and concentrated in vacuo. Pure product was obtained following reversed-phase HPLC using 20:80 water/methanol as eluant and the product was characterized by $^1$H NMR.

EXAMPLE 34

Nodulisporamide and 31-amino-31,32-dihydro-nodulisporamide

To 1.5 mg nodulisporic acid in 1 mL methylene chloride at room temperature was added 1 drop diisopropylethylamine, 1 drop NH$_4$OH and 2 mg N-hydroxybenzotriazole. To this was added 3 mg PyBOP and the solution was stirred for 15 min. The reaction was quenched with 2 mL saturated NaHCO$_3$, extracted with ethyl acetate, dried with $Na_2SO_4$, filtered and concentrated in vacuo. Pure nodulisporamide was obtained following preparative TLC (1×0.5 mm silica gel) using 1:9 methanol/chloroform as eluant. Nodulisporamide was characterized by $^1H$ NMR and mass spectrometry. Also obtained from this reaction was 31-amino-31,32-dihydro-nodulisporamide.

EXAMPLE 35

N-(Methoxycarbonylmethyl)-nodulisporamide

To 1.5 mg nodulisporic acid in 1 mL methylene chloride at room temperature was added 1 drop diisopropylethylamine, 2 mg N-hydroxybenzotriazole and 2 mg $HCl.H_2NCH_2CO_2Me$. To this solution was added 2 mg PyBOP. After 30 min, the reaction was quenched with 2 mL saturated $NaHCO_3$, extracted with ethyl acetate, dried using $Na_2SO_4$, filtered and concentrated under reduced pressure. Pure product was obtained following reversed-phase HPLC purification using 17.5:82.5 water/methanol as eluant. The product was characterized by $^1H$ NMR and mass spectrometry.

EXAMPLE 36

N,N-Tetramethylene-nodulisporamide

To 125 mg nodulisporic acid in 10 mL methylene chloride at 0° C. was added 0.18 mL diisopropylethylamine, 0.15 mL pyrrolidine followed by 108 mg PyBOP. After 5 minutes, the solution was warmed to room temperature. After 1.5 hours, the solution was poured in 25 mL saturated $NaHCO_3$, extracted with methylene chloride, dried with $Na_2SO_4$, filtered and concentrated under reduced pressure. Pure N,N-tetramethylene-nodulisporamide was obtained following reversed-phase HPLC purification using 50:50 acetonitrile/water as eluant (isocratic for ten min), followed by a linear 30 minute gradient to 75:25 acetonitrile/water. Pure product (26 mg) was characterized by $^1H$ NMR and MS.

EXAMPLE 37

N-Ethyl 29,30-dihydro-20,30-oxa-nodulisporamide

To 1 mg Compound B in 1 mL methylene chloride at room temperature was added 1 drop diisopropylethylamine, 1 drop $CH_3CH_2NH_2$, 3 mg N-hydroxybenzotriazole and 3 mg PyBOP. After 15 minutes, the reaction was quenched with 2 mL saturated $NaHCO_3$, extracted with ethyl acetate, dried with $Na_2SO_4$, filtered and concentrated in vacuo. The crude was purified by reversed-phase HPLC using 15:85 water/methanol as eluant and the purified product was characterized by $^1H$ NMR.

EXAMPLE 38

N-(2-Hydroxyethyl)-29,30-dihydro-20,30-oxa-nodulisporamide

To 0.7 mg Compound B in 1 mL methylene chloride at room temperature was added 1 drop diisopropylethylamine, 1 drop $HOCH_2CH_2NH_2$, 3 mg N-hydroxybenzotriazole and 3 mg PyBOP. After 15 minutes, the reaction was quenched with 2 mL saturated $NaHCO_3$, extracted with ethyl acetate, dried with $Na_2SO_4$, filtered and concentrated in vacuo. The crude was purified by reversed-phase HPLC using first 20:80 water/methanol then 15:85 water/methanol as eluant and the purified product was characterized by $^1H$ NMR.

EXAMPLE 39

N-(2-Hydroxyethyl)-3 1-hydroxy-20,30-oxa-29,30,31,32-tetrahydro-nodulisporamide

To 1 mg Compound C in 1 mL methylene chloride at room temperature was added 1 drop diisopropylethylamine, 1 drop $HOCH_2CH_2NH_2$, 3 mg N-hydroxybenzotriazole and 3 mg PyBOP. After 15 minutes, the reaction was quenched with 2 mL saturated $NaHCO_3$, extracted with ethyl acetate, dried with $Na_2SO_4$, filtered and concentrated in vacuo. The crude was purified by reversed-phase HPLC using first 20:80 water/methanol as eluant and the purified product was characterized by $^1H$ NMR.

EXAMPLE 40

N-tert-Butyl Nodulisporamide

To a solution of 30 mg of nodulisporic acid in 3 mL methylene chloride at 0° C. was added 0.03 mL triethylamine and 12 mg N-hydroxybenzotriazole followed by 28 mg BOP reagent. The solution was stirred for 10 minutes and then 0.05 mL tert-butylamine was added. The solution was stirred overnight at 4° C. and then poured into 1/1 saturated sodium bicarbonate/brine, extracted with methylene chloride and the combined organic layers dried over sodium sulfate. The solids were removed by filtration and the solution concentrated to dryness under reduced pressure. The residue was partially purified by preparative TLC on silica gel (one 1000 micron plate) using ½ acetone/hexanes as eluant. Additional purification using HPLC (6/4 acetonitrile/water for 15 minutes, then a 45 minute linear gradient to 7/3 acetontrile/water) yielded pure product (17 mg). The purified product was characterized by proton NMR and MS (m/z: 735.7 (M+1)).

The general procedure of Example 40 was repeated using the appropriate amines listed in Table 3 below to provide the corresponding monosubstituted nodulisporamide compounds. These compounds were characterized by proton NMR and/or mass spectrometry (unless otherwise specified, m/z is for M+1).

TABLE 3

Monosubstituted Aliphatic Nodulisporamide Derivatives

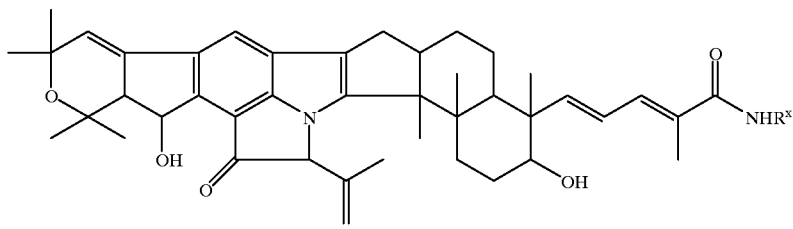

| Ex. | m/z | Amines | R$^x$ |
|---|---|---|---|
| 41 | 796.5 | Aminoacetaldehyde diethyl acetal | CH$_2$CH(OCH$_2$CH$_3$)$_2$ |
| 42 | 767.6 | (2-Hydroxyethoxy)-ethylamine | CH$_2$CH$_2$OCH$_2$CH$_2$OH |
| 43 | 792.5 | 4-(2-Aminoethyl)-morpholine | —CH$_2$CH$_2$—N(morpholine) |
| 44 | 790.4 | 1-(2-Aminoethyl)-piperidine | —CH$_2$CH$_2$—N(piperidine) |
| 45 | 807.5 | 6-Amino-2-methylheptan-2-ol | CH(CH$_3$)(CH$_2$)$_3$C(CH$_3$)$_2$OH |
| 46 | 737.5 | 3-Aminopropanol | (CH$_2$)$_3$OH |
| 47 | 751.5 | 4-Aminobutanol | (CH$_2$)$_4$OH |
| 48 | 765.6 | 5-Aminopentanol | (CH$_2$)$_5$OH |
| 49 | 791.5 | 1-(2-Aminoethyl)-piperazine | —CH$_2$CH$_2$—N(piperazine)N |
| 50 | 804.6 | 1-(3-Aminopropyl)-2-pyrrolidinone | —(CH$_2$)$_3$—N(pyrrolidinone) |
| 51 | 776.4 | 1-(2-Aminoethyl)-pyrrolidine | —(CH$_2$)$_2$—N(pyrrolidine) |
| 52 | 751.4 | 2-Aminobutanol | CH(CH$_2$OH)CH$_2$CH$_3$ |
| 53 | 750.5 | tert-Butylhydrazine | NHC(CH$_3$)$_3$ |
| 54 | 718.3 | Aminoacetonitrile | CH$_2$CN |
| 55 | 779.6 | 6-Aminohexanol | (CH$_2$)$_6$OH |
| 56 | 806.8 | 4-(3-Aminopropyl)-morpholine | —CH$_2$CH$_2$CH$_2$—N(morpholine) |
| 57 | 737.4 | 3-Aminopropan-2-ol | CH$_2$CH(OH)CH$_3$ |
| 58 | 765.4 | 2-Aminopentanol | CH(CH$_2$OH)CH$_2$CH$_2$CH$_3$ |

TABLE 3-continued

Monosubstituted Aliphatic Nodulisporamide Derivatives

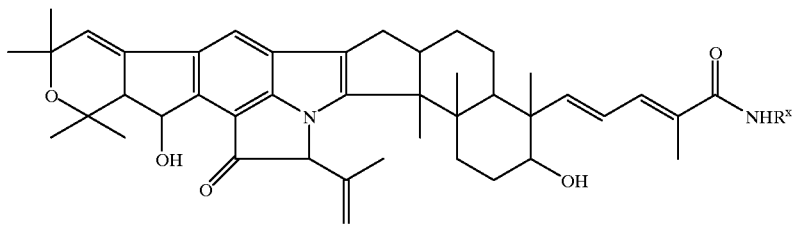

| Ex. | m/z | Amines | $R^x$ |
|---|---|---|---|
| 59 | 777.7 | 1-Amino-1-cyclopentane-methanol | HOCH$_2$—[cyclopentyl] |
| 60 |  | 2-(Methylthio)ethylamine | $CH_2CH_2SCH_3$ |
| 61 | 765.4 | 2-(Ethylthio)ethylamine | $CH_2CH_2SCH_2CH_3$ |
| 62 | 736.5 | Glycineamide | $CH_2CONH_2$ |
| 63 | 748.4 | 1-Aminopyrrolidine | —N[pyrrolidine] |
| 64 |  | 2-Amino-2-(hydroxymethyl)propanol | $CH(CH_3)(CH_2OH)_2$ |
| 65 | 777.6 | trans-2-Aminocyclohexanol | [2-hydroxycyclohexyl] |
| 66 | 777.6 | 1-Amino-4-methyl-piperazine | —N[piperazine]N—CH$_3$ |
| 67 | 766.5 | 2-(2-Aminoethylamino)-ethanol | $CH_2CH_2NHCH_2CH_2OH$ |
| 68 | 791.4 | 1-Aminomethyl-cyclohexan-1-ol | HO-[cyclohexyl]-CH$_2$— |
| 69 | 779.4 | 2-Aminohexanol | $CH(CH_2OH)(CH_2)_3CH_3$ |
| 70 | 751.5 | 2-Amino-1-methoxypropane | $CH(CH_2OCH_3)CH_3$ |
| 71 | 764.4 | 4-Aminomorpholine | —N[morpholine]O |
| 72 | 777.6 | trans-4-Aminocyclohexan-1-ol | [cyclohexyl]—OH |
| 73 | 739.4 | 2-Aminoethanethiol | $(CH_2)_2SH$ |
| 74 | 750.5 | 4-Aminobutylamine | $(CH_2)_4NH_2$ |

TABLE 3-continued

Monosubstituted Aliphatic Nodulisporamide Derivatives

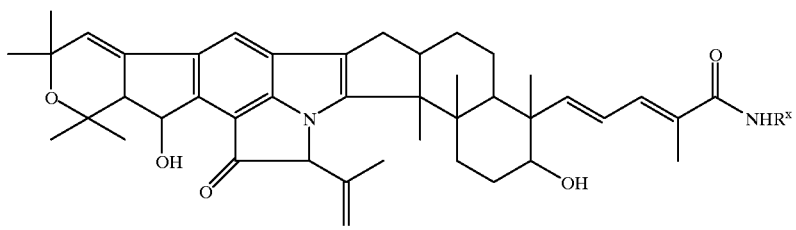

| Ex. | m/z | Amines | $R^x$ |
|---|---|---|---|
| 75 | 764.4 | 2-Amino-4,5-dihydrothiazole | |
| 76 | 747.5 | Aminocyclopentane | |
| 77 | | 2-(Methylsulfonyl)-ethylamine | $CH_2CH_2SO_2CH_3$ |
| 78 | | 2-(Methylsulfinyl)-ethylamine | $CH_2CH_2S(O)CH_3$ |
| 79 | 765.4 | 2-Amino-3-methylbutanol | $CH(CH(CH_3)_2)CH_2OH$ |
| 80 | 736.5 | 3-Aminopropylamine | $(CH_2)_3NH_2$ |
| 81 | 792.5 | 3-(Diethylamino)-propylamine | $(CH_2)_3N(CH_2CH_3)_2$ |
| 82 | 764.5 | 3-(Dimethylamino)-propylamine | $(CH_2)_3N(CH_3)_2$ |
| 83 | 723.5 | O-Ethylhydroxylamine | $OCH_2CH_3$ |
| 84 | 753.5 | 3-Amino-2-hydroxypropanol | $CH_2CH(OH)CH_2OH$ |
| 85 | 709.4 | O-Methylhydroxylamine | $OCH_3$ |
| 86 | 737.4 | 2-Methoxyethylamine | $CH_2CH_2OCH_3$ |
| 87 | 764.4 | N-Acetylethylenediamine | $CH_2CH_2NHC(O)CH_3$ |
| 88 | 790.6 | 2-Aminoethyl-1-methylpyrrolidine | |
| 89 | 751.5 | 2-Amino-2-methyl-propanol | $C(CH_3)_2CH_2OH$ |
| 90 | 719.4 | Cyclopropylamine | $c-C_3H_5$ |
| 91 | 760.5 | Cyclohexylamine | $c-C_6H_{11}$ |
| 92 | 765.5 | 3-Ethoxypropylamine | $(CH_2)_3OCH_2CH_3$ |
| 93 | 719.5 | Allylamine | $CH_2CH=CH_2$ |
| 94 | 789.5 | 2-Amino-2-(hydroxymethyl)butanol | $C(CH_2CH_3)(CH_2OH)_2$ |
| 95 | 717.5 | Propargylamine | $CH_2C\equiv CH$ |
| 96 | 765.5 | Glycine ethyl ester | $CH_2CO_2CH_2CH_3$ |
| 97 | 725.7 | 2-Fluoroethylamine | $CH_2CH_2F$ |
| 98 | 905.5 | 3-(Dodecyloxy)-propylamine | $(CH_2)_3O(CH_2)_{11}CH_3$ |
| 99 | 751.0 | 2-(Dimethylamino)-ethylamine | $CH_2CH_2N(CH_3)_2$ |
| 100 | 791.4 | 1-(2-Aminoethyl)-imidazolone | |
| 101 | 766.4 | 2-(2-Aminoethoxy)- | $CH_2CH_2OCH_2CH_2NH_2$ |

TABLE 3-continued

Monosubstituted Aliphatic Nodulisporamide Derivatives

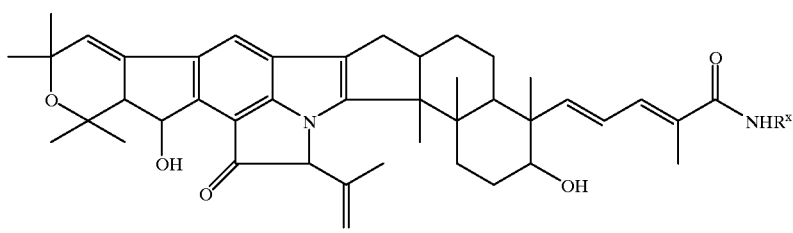

| Ex. | m/z | Amines | R$^x$ |
|---|---|---|---|
| 102 | | ethylamine 2,2,2-Trifluoroethylamine | $CH_2CF_3$ |
| 103 | 780.5 | Ethyl hydrazinoacetate | $NHCH_2CO_2CH_2CH_3$ |
| 104 | 763.5 | D,L-2-(Aminomethyl)-tetrahydrofuran | —CH$_2$—[tetrahydrofuran-2-yl] |
| 105 | | 1-Aminopiperidine | —N[piperidinyl] |
| 106 | 765.6 | D-Alanine methyl ester | $CH(CH_3)CO_2CH_3$ |
| 107 | 777.5 | 4-Amino-4-methyl-pentan-2-one | $C(CH_3)_2CH_2C(O)CH_3$ |
| 108 | 837.6 | Diethyl 2-aminomalonate | $CH(CO_2CH_2CH_3)_2$ |
| 109 | | 5-Aminouracil | [5-uracilyl] |
| 110 | 707.6 | Ethylamine | $CH_2CH_3$ |
| 111 | 807.8 | Norleucine methyl ester | $CH(CH_2CH_2CH_3)CO_2CH_3$ |
| 112 | 751.7 | 3-Methoxypropylamine | $CH_2CH_2CH_2OCH_3$ |
| 113 | 745.5 | 1,1-Dimethylpropargyl-amine | $C(CH_3)_2C\equiv CH$ |
| 114 | 749.7 | Pentylamine | $(CH_2)_4CH_3$ |
| 115 | 777.9 | 4-Aminoheptane | $CH(CH_2CH_2CH_3)_2$ |
| 116 | 763.8 | Hexylamine | $(CH_2)_5CH_3$ |
| 117 | 776.8 | cis-1,2-Diaminocyclohexane | H$_2$N-[cyclohexyl] |
| 118 | 788.9 | 3-Aminoquinuclidine | [quinuclidin-3-yl] |
| 119 | 751.7 | beta-Alanine | $CH_2CH_2CO_2H$ |
| 120 | 793.5 | L-Valine methyl ester | $CH(CH(CH_3)_2)CO_2CH_3$ |

TABLE 3-continued

Monosubstituted Aliphatic Nodulisporamide Derivatives

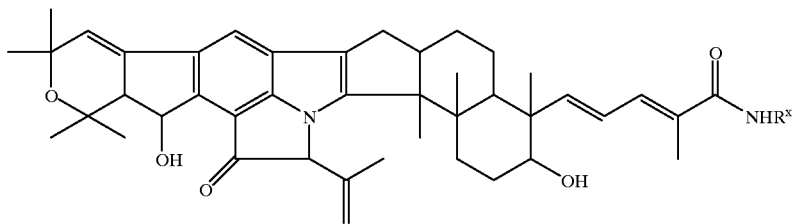

| Ex. | m/z | Amines | R$^x$ |
|---|---|---|---|
| 121 | | 1-Amino-4-(2-Hydroxyethyl)piperazine | —N(piperazine)N•CH$_2$CH$_2$•OH$_2$ |
| 122 | 753.4 | Aminooxyacetic acid | OCH$_2$CO$_2$H |
| 123 | 834.5 | 4-Amino-1-carboethoxypiperidine | —(piperidine)N—CO$_2$CH$_2$CH$_3$ |
| 124 | 763.5 | (R)-2-(Aminomethyl)-tetrahydrofuran | —CH$_2$-(tetrahydrofuran) |
| 125 | 763.6 | (S)-2-(Aminomethyl)-tetrahydrofuran | —CH$_2$-(tetrahydrofuran) |
| 126 | 765.6 | L-Valinol | CH(CH(CH$_3$)$_2$)CH$_2$OH |
| 127 | 765.7 | D-Valinol | CH(CH(CH$_3$)$_2$)CH$_2$OH |
| 128 | 737.7 | L-Alaninol | CH(CH$_3$)CH$_2$OH |
| 129 | 737.6 | D-Alaninol | CH(CH$_3$)CH$_2$OH |
| 130 | 721.7 | Isopropylamine | CH(CH$_3$)$_2$ |
| 131 | 735.7 | tert-butylamine | C(CH$_3$)$_3$ |
| 132 | 735.7 | iso-Butylamine | (CH$_2$)CH(CH$_3$)$_2$ |
| 133 | 735.5 | sec-Butylamine | CH(CH$_3$)CH$_2$CH$_3$ |
| 134 | 737.6 | (R)-3-Aminopropan-2-ol | CH$_2$CH(CH$_3$)OH |
| 135 | 735.6 | n-Butylamine | (CH$_2$)$_3$CH$_3$ |
| 136 | 751.7 | 2-Ethoxyethylamine | (CH$_2$)$_2$OCH$_2$CH$_3$ |
| 137 | 787.7 | 2-Aminoethylcyclohexane | —CH$_2$CH$_2$-(cyclohexenyl) |
| 138 | 813.7 | 1-Aminoadamantane | 1-adamantyl |
| 139 | 805.7 | n-Nonylamine | (CH$_2$)$_8$CH$_3$ |
| 140 | 749.8 | 2-Amino-3-methylbutane | CH(CH$_3$)CH(CH$_3$)$_2$ |
| 141 | 750.6 | 3-(Methylamino)-propylamine | (CH$_2$)$_3$NHCH$_3$ |
| 142 | 778.7 | 2-(Diethylamino)-ethylamine | (CH$_2$)$_2$N(CH$_2$CH$_3$)$_2$ |
| 143 | 776.7 | 1-Amino-homopiperidine | —(homopiperidine) |

The general procedure of Example 40 was repeated using the amines listed in Table 4 below to provide the corresponding nodulisporamide compounds. These compounds were characterized by proton NMR and/or mass spectrometry (unless otherwise specified, m/z is for M+1).

TABLE 4

Nodulisporamide Derivatives

| Ex. | m/z | Amine | NR$^{x}$R$^{y}$ |
|---|---|---|---|
| 144 | 791.5 | 1-(2-Aininoethyl)-piperazine | —N(piperazine)N•CH$_2$CH$_2$—NH$_2$ |
| 145 | 776.6 | 4-Aminomethylpiperidne | —N(piperidine)CH$_3$•NH$_2$ |
| 146 | 765.4 | Thiomorpholine | —N(thiomorpholine)S |
| 147 | 759.4 | Diallylamine | N(CH$_2$CH=CH$_2$)$_2$ |
| 148 | 737.4 | 2-(Methylamino)ethanol | N(CH$_3$)CH$_2$CH$_2$OH |
| 149 | 795.4 | Diisopropanolamine | N(CH$_2$CH(CH$_3$)OH)$_2$ |
| 150 | 763.5 | L-2-(Hydroxymethyl)-pyrrolidine | (pyrrolidine with CH$_2$OH) |
| 151 | 763.5 | D-2-(Hydroxymethyl)-pyrrolidine | (pyrrolidine with CH$_2$OH) |
| 152 | 749.5 | 3-Hydroxypyrrolidine | (pyrrolidine with OH) |
| 153 | 732.7 | Methylaminoacetonitrile | N(CH$_3$)CH$_2$C≡N |
| 154 |  | 4-(2-hydroxyethyl)-piperazine | —N(piperazine)N—CH$_2$CH$_2$OH |
| 155 | 777.7 | 4-Ethylpiperazine | —N(piperazine)N—CH$_2$CH$_3$ |

TABLE 4-continued

Nodulisporamide Derivatives

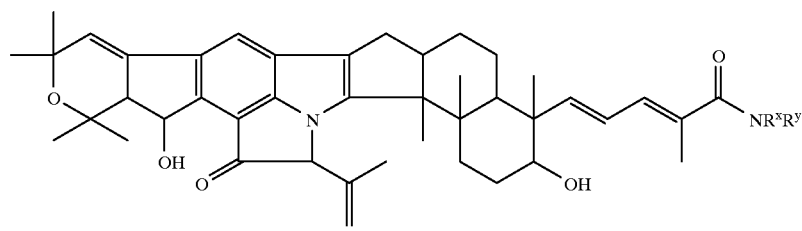

| Ex. | m/z | Amine | NR$^x$R$^y$ |
|---|---|---|---|
| 156 | 721.5 | N-Ethylmethylamine | N(CH$_3$)CH$_2$CH$_3$ |
| 157 | 735.6 | N-(Methyl)isopropylamine | N(CH$_3$)CH(CH$_3$)$_2$ |
| 158 | 735.5 | N-Methylpropylamine | N(CH$_3$)CH$_2$CH$_2$CH$_3$ |
| 159 | 749.5 | N-Methylbutylamine | N(CH$_3$)CH$_2$CH$_2$CH$_2$CH$_3$ |
| 160 | 765.7 | N-Ethyl-2-methoxyethyl-amine | N(CH$_2$CH$_3$)CH$_2$CH$_2$OCH$_3$ |
| 161 | 751.7 | N-Methyl-2-methoxyethyl-amine | N(CH$_3$)CH$_2$CH$_2$OCH$_3$ |
| 162 | 749.7 | N-Ethylpropylamine | N(CH$_2$CH$_3$)CH$_2$CH$_2$CH$_3$ |
| 163 | 751.5 | Tetrahydrothiazole | |
| 164 | 767.8 | Diethanolamine | N(CH$_2$CH$_2$OH)$_2$ |
| 165 | 763.8 | 3-Hydroxypiperidine | |
| 166 | 763.9 | 4-Hydroxypiperidine | |
| 167 | 749.6 | N-(Ethyl)isopropylamine | N(CH$_2$CH$_3$)CH(CH$_3$)$_2$ |
| 168 | 747.8 | Piperidine | |
| 169 | 735.8 | Diethylamine | N(CH$_2$CH$_3$)$_2$ |
| 170 | 762.7 | 4-Methylpiperazine | |
| 171 | 767.6 | Tetrahydrothiazole-S-oxide | |
| 172 | 791.7 | Dibutylamine | N(CH$_2$CH$_2$CH$_2$CH$_3$)$_2$ |
| 173 | 745.7 | 1,2,3,6-Tetrahydropyridine | |

TABLE 4-continued

Nodulisporamide Derivatives

| Ex. | m/z | Amine | NR$^x$R$^y$ |
|---|---|---|---|
| 174 | 790.8 | 3-(Carboxamido)piperidine | piperidine with CONH$_2$ at 3-position |
| 175 | 819.6 | 3-(Carboethoxy)piperidine | piperidine with CO$_2$CH$_2$CH$_3$ at 3-position |
| 176 | 761.6 | Hexamethyleneimine | 7-membered N ring |
| 177 | 820.7 | 1-(Carboethoxy)piperazine | piperazine with —CO$_2$CH$_2$CH$_3$ |
| 178 | 819.7 | Dipentylamine | N(CH$_2$CH$_2$CH$_2$CH$_2$CH$_3$)$_2$ |
| 179 | 775.6 | Heptamethyleneimine | 8-membered N ring |
| 180 | 787.6 | Octahydroindole | octahydroindole |
| 181 | 760.5 | 4,5-Dihydro-5,5-dimethylimidazole | 4,5-dihydro-5,5-dimethylimidazole |
| 182 | 707.5 | Dimethylamine | N(CH$_3$)$_2$ |
| 183 | 763.7 | Dipropylamine | N(CH$_2$CH$_2$CH$_3$)$_2$ |
| 184 | 761.7 | 2-Methylpiperidine | 2-methylpiperidine |

TABLE 4-continued

Nodulisporamide Derivatives

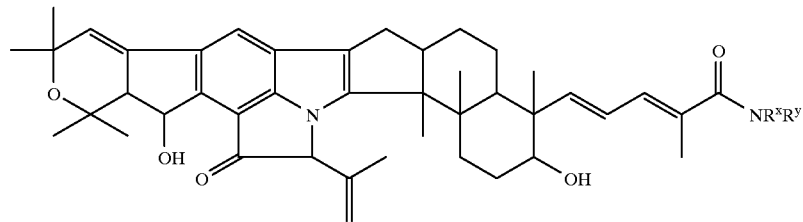

| Ex. | m/z | Amine | NR$^x$R$^y$ |
|---|---|---|---|
| 185 | 779.5 | 2-(Butylamino)ethanol | N((CH$_2$)$_2$CH$_3$)CH$_2$CH$_2$OH |
| 186 | 731.7 | Methylpropargylamine | N(CH$_3$)CH$_2$C≡CH |
| 187 | 854.7 | 1-(4-Methoxyphenyl)-piperazine | [piperazine structure with OCH$_3$] |
| 188 | 931.9 | Dinonylamine | N((CH$_2$)$_8$CH$_3$)$_2$ |
| 189 | 903.8 | Dioctylamine | N((CH$_2$)$_7$CH$_3$)$_2$ |
| 190 | 815.7 | 4,6,6-Trimethyl-2-aza[3.2.1]bicyclooctane | [bicyclic structure with CH$_3$ groups] |
| 191 | 750.7 | N,N'-Dimethylethylene-diamine | N(CH$_3$)(CH$_2$)$_2$NHCH$_3$ |
| 192 | 750.6 | 3-(Methylamino)-propylamine | N(CH$_3$)(CH$_2$)$_3$NH$_2$ |
| 193 | 813.7 | L-2-Amino-3-phenylpropanol | NHCH(CH$_2$OH)CH$_2$Ph |
| 194 | 785.6 | 2-Amino-4-methylphenol | NHPh(2-OH,4-CH$_3$) |
| 195 | | 4-Amiobenzylamine | NHCH$_2$Ph(4-NH$_2$) |
| 196 | 789.4 | 4-Chloroaniline | NHPh(4-Cl) |
| 197 | 799.5 | 4-(2-Hydroxyethyl)aniline | NHPh(4-CH$_2$CH$_2$OH) |
| 198 | 799.5 | 2-(2-Hydroxyethyl)aniline | NHPh(2-CH$_2$CH$_2$OH) |
| 199 | 783.4 | 2-Phenylethylamine | NHCH$_2$CH$_2$Ph |
| 200 | 785.4 | 2-(Hydroxymethyl)aniline | NHPh(2-CH$_2$OH) |
| 201 | 798.8 | 3-(Diniethylamino)aniline | NHPh(3-N(CH$_3$)$_2$ |
| 202 | 835.1 | 4-(Sulfonylamido)aniline | NHPh(4-SO$_2$NH$_2$) |
| 203 | | Phenylhydrazine | NHNHPh |
| 204 | 798.4 | 2-Carboxamidoaniline | NHPh(2-CONH$_2$) |
| 205 | 799.8 | 4-(Aminoethyl)phenol | NHCH$_2$CH$_2$Ph(4-OH) |
| 206 | 884.5 | 4-(3-Aminopropyl)-1-sulfonamidobenzene | NHCH$_2$CH$_2$Ph(4-SO$_2$NH$_2$) |
| 207 | 770.5 | 2-Aminoaniline | NHPh(2-NH$_2$) |
| 208 | 883.7 | L-Leucine benzyl ester | NHCH(CH$_2$CH(CH$_3$)$_2$)CO$_2$CH$_2$Ph |
| 209 | 888.5 | 4-(tert-butyl)benzyl-sulfonamide | NHSO$_2$CH$_2$Ph(4-C(CH$_3$)$_3$) |
| 210 | 833.6 | Benzylsulfonamide | NHSO$_2$CH$_2$Ph |
| 211 | 788.7 | 2-fluorophenylhydrazine | NHNHPh(2-F) |
| 212 | 843.8 | 4-(2-Aminoethyl)-1,2-dimethoxybenzene | [dimethoxybenzene structure with NHCH$_2$CH$_2$-] |

TABLE 4-continued

Nodulisporamide Derivatives

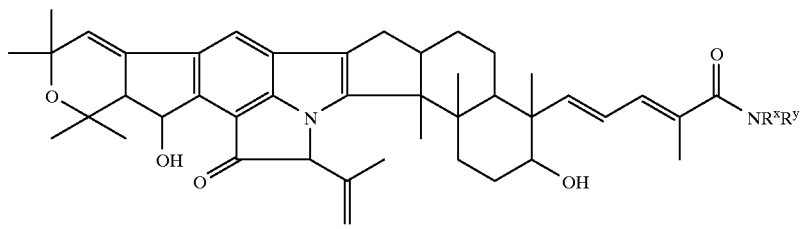

| Ex. | m/z | Amine | NR$^{xRy}$ |
|---|---|---|---|
| 213 | 867.5 | L-Proline benzyl ester | *(structure: N-methyl pyrrolidine with PhCH$_2$O$_2$C substituent)* |
| 214 | 813.8 | 4-Aminomethyl-1,2-methylenedioxybenzene | *(structure: NH-CH$_2$-benzodioxole)* |
| 215 | 837.5 | 4-(Trifluoromethyl)-benzylamine | NHCH$_2$Ph(4-CF$_3$) |
| 216 | 882.6 | 1-((3,4-methylenedioxy)-benzyl)piperazine | *(structure: piperazine-CH$_2$-benzodioxole)* |
| 217 | 862.7 | 3-(Benzyloxy)aniline | NHPh(4-OCH$_2$Ph) |
| 218 | 801.4 | 4-(Methylthio)aniline | NHPh(4-SCH$_3$) |
| 219 | 855.5 | L-Phenylalanine ethyl ester | NHCH(CH$_2$Ph)CO$_2$CH$_2$CH$_3$ |
| 220 | 841.4 | D-Phenylalanine methyl ester | NHCH(CH$_2$Ph)CO$_2$CH$_3$ |
| 221 | 799.4 | 4-(Methoxy)benzylamine | NHCH$_2$Ph(4-OCH$_3$) |
| 222 | 819.5 | 1-(Aminomethyl)napthalene | NHCH$_2$-1-naphthyl |
| 223 | 792.4 | 1,2,3,4-Tetrahydro-isoquinoline | *(structure: N-methyl tetrahydroisoquinoline)* |
| 224 | 821.8 | 3-Amino-2-hydroxy-napthalene | *(structure: 2-hydroxy-3-aminonaphthalene)* |
| 225 | 801.7 | 3-(2-Aminoethyl)-fluorobenzene | NHCH$_2$CH$_2$(3-F)Ph |
| 226 | 823.7 | 4-Phenylpiperazine | *(structure: N-Ph piperazine)* |
| 227 | 814.7 | D-Phenylaninol | NHCH(CH$_2$Ph)CH$_2$OH |

TABLE 4-continued

Nodulisporamide Derivatives

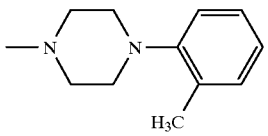

| Ex. | m/z | Amine | NR$^{xRy}$ |
|---|---|---|---|
| 228 | 838.6 | 1-(o-Tolyl)piperazine | 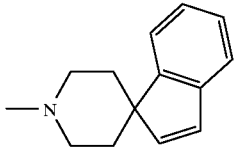 |
| 229 | 847.6 | Spiro(1H-indene-1,4'-piperidine) | 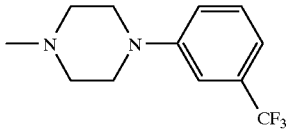 |
| 230 | 773.6 | 4-Fluoroaniline | NHPh(4-F) |
| 231 | 787.5 | 2-Fluorobenzylamine | NHCH$_2$Ph(2-F) |
| 232 | 799.7 | 2-Amino-1-phenylethanol | NHCH$_2$CH(Ph)OH |
| 234 | 801.8 | 4-(2-Aminoethyl)-1-fluorobenzene | NHCH$_2$CH$_2$Ph(4-F) |
| 235 | 829.5 | 4-(2-Amino-2-methylpropyl)-1-fluorobenzene | NHC(CH$_3$)$_2$CH$_2$Ph(3-F) |
| 236 | 791.7 | 3,4-Difluoroaniline | NHPh(3,4-diF) |
| 237 | 783.7 | 3-(Aminomethyl)toluene | NHCH$_2$Ph(3-CH$_3$) |
| 238 | 784.5 | 3-Methylphenylhydrazine | NHNH(3-CH$_3$)Ph |
| 239 | 803.5 | 2-Chlorobenzylamine | NHCH$_2$Ph(2-Cl) |
| 240 | 838.8 | 2,4-Dichorobenzylamine | NHCH$_2$Ph(2,4-diCl) |
| 241 | 782.7 | 4-Methylphenylhydrazine | NHNHPh(4-CH$_3$) |
| 242 | 803.8 | 4-Chlorobenzylamine | NHCH$_2$Ph(4-Cl) |
| 243 | 797.7 | 3-phenylpropylamine | NH(CH$_2$)$_3$Ph |
| 244 | 817.6 | 4-(2-Annnoethyl)-1-chlorobenzene | NHCH$_2$CH$_2$Ph(4-Cl) |
| 245 | 893.8 | 1-(m-Trifluoromethyl phenyl)piperazine | 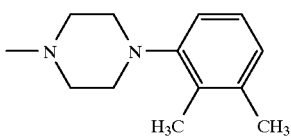 |
| 246 | 852.6 | 1-(2,3-Dimethylphenyl)piperazine |  |
| 247 | 812.7 | N-Methyl-N-phenyl-ethylenediamine | NHCH$_2$CH$_2$N(CH$_3$)Ph |
| 248 | 837.6 | 3 L(Trifluoromethyl)-benzylamine | NHCH$_2$Ph(3-CF$_3$) |
| 249 | 837.7 | 2-(Trifluoromethyl)-benzylamine | NHCH$_2$Ph(2-CF$_3$) |

TABLE 4-continued

Nodulisporamide Derivatives

| Ex. | m/z | Amine | NR^xR^y |
|---|---|---|---|
| 250 | | 1-(4-Methoxyphenyl)-piperazine | —N(piperazine)N—C6H4—OCH3 |
| 251 | 795.7 | 2-Aminoindane | (2-aminoindane structure) |
| 252 | 843.6 | 9-Aminofluorene | (9-aminofluorene structure) |
| 253 | 811.7 | 4-Phenylbutylamine | NH(CH$_2$)$_4$Ph |
| 254 | 827.8 | (R,R)-2-Methylamino-3-phenylbutane | N(CH$_3$)CH(CH$_3$)CH(CH$_3$)Ph |
| 255 | 827.8 | (S,S)-2-Methylamino-3-phenylbutane | N(CH$_3$)CH(CH$_3$)CH(CH$_3$)Ph |
| 256 | 825.9 | Benzylbutylalnine | N(CH$_2$Ph)(CH$_2$)$_3$CH$_3$ |
| 257 | 785.6 | O-Benzylhydroxylamine | NHOCH$_2$Ph |
| 258 | 805.5 | 2,6-Difluorobenzylamine | NCH$_2$Ph(2,6-diF) |
| 259 | 920.9 | 1-(2-(o-Trifluoromethyl-phenyl)ethyl)piperazine | —N(piperazine)N—CH$_2$CH$_2$—C6H4-F |
| 260 | 797.7 | (S)-N,alpha-Dimethylbenzylamine | N(CH$_3$)CH(CH$_3$)Ph |
| 261 | 783.7 | (S)-alpha-Methylbenzylamine | NHCH(CH$_3$)Ph |
| 262 | 797.6 | Methyl benzyl amine | N(CH$_3$)CH$_2$Ph |
| 263 | | 4-Aminomethyl-1,2-djchlorobenzene | NHCH$_2$Ph(3,4-diCl) |
| 264 | 783.7 | (R)-alpha-Methylbenzylamine | N(CH$_3$)CH(CH$_3$)Ph |
| 265 | 873.8 | 1-Benzylamino-2-phenylethane | N(CH$_2$Ph)CH$_2$CH$_2$Ph |
| 266 | 784.6 | Benzylhydrazine | NHNHCH$_2$Ph |
| 267 | 805.7 | 2,4-Difluorobenzylamine | NHCH$_2$Ph(2,4-diF) |
| 268 | 838.8 | 2,5-Dichlorophenyl-hydrazine | NHNHPh(2,5-diCl) |
| 269 | 787.7 | 3-Fluorobenzylamine | NHCH$_2$Ph(3-F) |

TABLE 4-continued

Nodulisporamide Derivatives

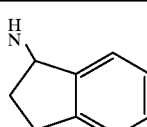

| Ex. | m/z | Amine | NR$^{x}$R$^{y}$ |
|---|---|---|---|
| 270 | 795.5 | 1-Aminoindane | 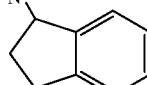 |
| 271 | 859.8 | 1,2-Diphenylethylamine | NHCH(Ph)CH$_2$Ph |
| 272 | 801.8 | 3,4-Dihydroxybenzylamine | NHCH$_2$Ph(3,4-diOH) |
| 273 | 829.7 | 2,4-Dimethoxy-benzylamine | NHCH$_2$Ph(3,4-diOCH$_3$) |
| 274 | 783.8 | N-Benzylmethylamine | N(CH$_3$)CH$_2$Ph |
| 275 | 797.7 | N-Benzylethylamine | N(CH$_2$CH$_3$)CH$_2$Ph |
| 276 |  | (R)-N,alpha-Dimethylbenzylamine | N(CH$_3$)CH(CH$_3$)Ph |
| 277 | 770.5 | 3-(Aminomethyl)pyridine | 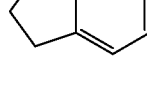 |
| 278 | 745.9 | 3-Amino-1,2,4-triazole | 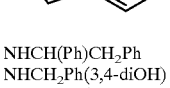 |
| 279 | 757.4 | 2-Aminopyrimidine | 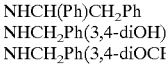 |
| 280 | 784.6 | 2-(2-Aminoethyl)pyridine | 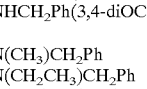 |
| 281 | 787.5 | 1-(3-Aminopropyl)-imidazole | 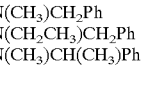 |
| 282 | 770.6 | 4-(Aminomethyl)pyridine | 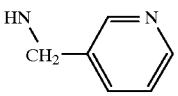 |
| 283 | 757.4 | 2-Aminopyrazine | 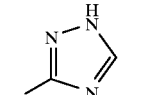 |

TABLE 4-continued
Nodulisporamide Derivatives
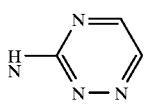
| Ex. | m/z | Amine | NR^xR^y |
|---|---|---|---|
| 284 | | 3-Amino-1,2,4-triazine | 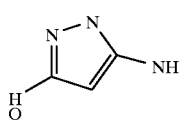 |
| 285 | | 5-Amino-3-hydroxypyrazole | 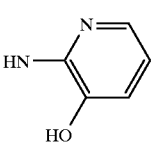 |
| 286 | | 2-Amino-3-hydroxypyridine | 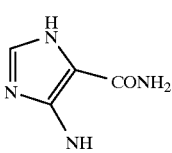 |
| 287 | | 4-Amino-5-carboxamidoimidazole | 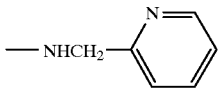 |
| 288 | 770.4 | 2-(Aminomethyl)pyridine | 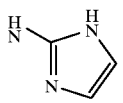 |
| 289 | 751.5 M + Li | 2-Aminoimidazole | 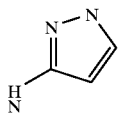 |
| 290 | 745.4 | 3-Aminopyrazole | 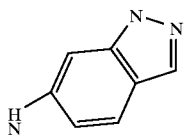 |
| 291 | 795.2 | 6-Aminobenzopyrazole | |

TABLE 4-continued

Nodulisporamide Derivatives

| Ex. | m/z | Amine | NR$^x$R$^y$ |
|---|---|---|---|
| 292 | 797.5 | 4-Amino-1,2,4-triazole | |
| 293 | | 2-Amino-4,5-dihydrothiazole | |
| 294 | 762.4 | 2-Aminothiazole | |
| 295 | 795.4 | 5-Aminobenzopyrazole | |
| 296 | 761.6 | 3,5-Diamino-1,2,4-triazole | |
| 297 | 825.7 | 1-(2-Pyridyl)piperazine | |
| 298 | 798.7 | 4-(Ethylaminomethyl)-pyridine | |
| 299 | 1032.7 | L-Tryptophan-1,1-diphenylmethylamide | |

TABLE 4-continued

Nodulisporamide Derivatives

[Structure of nodulisporamide derivative with NR^x R^y group]

| Ex. | m/z | Amine | NR^xR^y |
|-----|-------|------------------------------|---------|
| 300 |       | 2-(Aminomethyl)thiophene     | [HN-CH2-thiophene] |
| 301 |       | 2-(2-Aminoethyl)-1-methylpyrrole | [HN-CH2CH2-N-methylpyrrole with CH3] |
| 302 | 759.5 | 2-(Aminomethyl)furan         | [HN-CH2-furan] |

EXAMPLE 303

General Procedure for the Preparation of Additional Amide Derivatives of Nodulisporic Acid To a solution of 30 mg of nodulisporic acid in 3 mL methylene chloride at 0° C. add 0.03 mL triethylamine and 12 mg N-hydroxybenzotriazole followed by 28 mg BOP reagent. Stir the solution for 10 minutes and then add 50 mg of amine selected from Table 5. Stir the solution overnight at 4° C. and then pour into 1/1 saturated sodium bicarbonate/brine, extract with methylene chloride and dry the combined organic layers over sodium sulfate. Remove the solids by filtration and concentrate the solution to dryness under reduced pressure. Pure product may be obtained by flash chromatography or preparative TLC on silica gel or reversed-phase liquid chromatography. The purified product may be characterized by proton NMR and mass spectrometry.

Table 5: Amines for the Preparation of Additional Nodulisporamide Derivatives

N-Methyl-2,2,2-trifluoroethylamine, 2,2,3,3,3-Pentafluoropropylamine, N-Methyl-2,2,3,3,3-pentafluoropropylamine, 1,1,1,3,3,3-Hexafluoroisopropylamine, 2-Difluoro-3-Methoxy-1-methylpropylamine, N-Methyl- 1,1,1,3,3,3-hexafluoroisopropylamine, 1,1,1-Trifluoromethylpropylamine, 2-(3,3,3-Trifluoromethyl)propylamine, N--Methyl-1,1,1,3,3,3-hexafluoroisopropylamine, Di-(2,2,2-trifluoroethyl)amine, N-(2-Methoxyethyl)-2,2,2-trifluoroethylamine, 2-Methoxy-1-methyl-ethylamine, 3-Methoxy-1-methyl-propylamine, 2-Methoxy-1-methyl-ethylamine, N-Methyl-2-methoxy-1-benzylethylamine, 1-Methoxymethyl-3-methyl-butylamine, Methylsulfonamide, Isopropylsulfonamide, Ethylsulfonamide, Benzylsulfonamide, sec-Butylsulfonamide, N-Methyl-ethylsulfonamide, N,1,1-Trimethylpropargylamine, N-Ethyl- 1,1-dimethyl-propargylamine, N,1-Dimethyl-propargylamine, 1-Methyl-propargylamine, 1-Trifluoromethylpropargylamine, N,1,1-Trimethyl-propargylamine, N-Ethyl-1,1-dimethyl-propargylamine, N,1-Dimethyl-propargylamine, N,1,1-Trimethyl-propargylamine, 1-Methyl-propargylamine, 1-Trifluoromethylpropargylamine, N-Ethylpropargylamine, N-(2-Methoxyethyl)propargylamine, 1-Amino-2-pentyne, 1-Amino-3-pentyne, 1-Amino-4-pentyne, 1-Methylamino-2-pentyne, 1-Methylamino-3-pentyne, 1-Methylamino-4-pentyne, 1-Ethylamino-4-pentyne, 1-Trifluoromethylamino-2-pentyne, 1-Trifluoromethylamino-3-pentyne, 1-Trifluoromethylamino-4-pentyne, N-(2-Methoxyethyl)-2-amino-1,1-dimethyl-2-butyne, 1-Amino-2-butyne, 1-Amino-3-butyne, N-Methylamino-2-butyne, N-Methylamino-3-butyne, 1-Ethylamino-3-butyne, 2-(Aminomethyl)dioxane, 2-(2-Aminoethyl)dioxane, 2-(3-Aminopropyl)dioxane, 2-(2-Aminopropyl)dioxane, 2-(Methylaminomethyl)dioxane, 2-(l-Aminoethyl)dioxane, 2-Aminomethyl-2H-tetrahydropyran, 2-(2-Aminoethyl)-2H-tetrahydropyran, 2-(3-Aminopropyl)-2H-tetrahydropyran, 2-(2-Aminopropyl)-2H-tetrahydropyran, 2-(2-Aminoethyl)-5-ethyl-2H-tetrahydropyran, 2-Methylaminomethyl-2H-tetrahydropyran, 2-(1-Aminoethyl)-2H-tetrahydropyran, 2-(2-Aminopropyl) tetrahydrofuran, 2-Aminomethyl-5-ethyl-tetrahydrofuran, 2-Methylaminomethyl-tetrahydrofuran, 2-(Ethylaminomethyl)tetrahydrofuran, 2-(1-Aminoethyl) tetrahydrofuran, 4-(Methoxymethyl)benzylamine, 4-(2-Methoxyethyl)benzylamine, 4-(Ethoxymethyl) benzylamine, 4-(Acetoxyoxymethyl)benzylamine, 3-(Dimethylaminomethyl)benzylamine, 4-(Sulfonamidomethyl)benzylamine, 2-Chloro-6-fluoro-benzylamine, 3-Chloro-4-fluoro-benzylamine, 2-Chloro-4-fluoro-benzylamine, 3,5-Difluoro-benzylamine, 2,4-Difluoro-benzylamine, Pentafluorobenzylamine, 4-Methoxy-2,3,5,6-tetrafluorobenzylamine, 4-(Methyl) benzylamine, Benzylamine, 4-(Ethyl)benzylamine, 4-(Ethoxy)benzylamine, 4-(Isopropyl)benzylamine, 4-(Isobutyl)benzylamine, 4-(Isopropoxy)benzylamine, 4-(Isobutoxy)benzylamine, 4-(Allyl)benzylamine, 4-(Allyloxy)benzylamnine, 4-(3,3,1,1-Tetrafluoroallyloxy) benzylamine, 4-(Trifluoromethoxy)benzylamine, 4-(2,2,2-trifluoroethoxy)benzylamine, 3,4-Ethylenedioxybenzylamine, 4-Methoxymethyl-2-chloro-phenethylamine, 4-(2-Methoxyethyl)phenethylamine, 4-(Ethoxymethyl)phenethylamine, 4-(Acetoxyoxymethyl) phenethylamine, 3-(Dimethylaminomethyl) phenethylamine, 1-Phenyl-2,2,2-trifluoroethylamine, 4-(Trifluoromethoxy)aniline, 4-Methoxyaniline, 4-Ethoxyaniline, 3-Chloro-4-fluoro-aniline, 4-Chloro-2-fluoro-aniline, 4-(Acetoxy)aniline, 4-(Butoxy)aniline, 3-Chloroaniline, 4-(Methylthio)aniline, 5-(Aminomethyl) benzofuran, 5-(Methylaminomethyl)benzofuran, 4-(1-Aminoethyl)benzofuran, 5-(2-Aminoethyl)benzofuran, 5-Aminomethyl-2,3-dihydro-benzofuran, 5-Methylaminomethyl-2,3-dihydro-benzofuran, 4-1-Aminoethyl-2,3-dihydro-benzofuran, 5-2-Aminoethyl-2,3-dihydro-benzofuran, 5-Aminomethyl-2H-tetrahydrobenzopyran, 5-Methylaminomethyl-2H-tetrahydrobenzopyran, 4-1-Aminoethyl-2H-tetrahydrobenzopyran, 5-2-Aminoethyl-2H-tetrahydrobenzopyran, 5-Aminomethyl-2H-tetrahydrobenzopyran, 5-Methylaminomethyl-2H-tetrahydrobenzopyran, 4-(1-Aminoethyl)-2H-tetrahydrobenzopyran, 5-(2-Aminoethyl)-2H-tetrahydrobenzopyran, 5-Aminomethyl-benzo-1,4-dioxane, 5-Methylaminomethyl-benzo-1,4-dioxane, 4-1-Aminoethyl-benzo-1,4-dioxane, 5-2-Aminoethyl-benzo-1,4-dioxane, 5-Aminomethyl-benzo-1,4-dioxane, 5-Methylaminomethyl-benzo 1,4-dioxane, 4-(1-Aminomethyl)-benzo-1,4-dioxane, 5-(2-Aminoethyl)-benzo-1,4-dioxane, 3-Amino-5-methoxy-thiophene, 2-Amino-5-chloro-thiophene, 2-(2-Aminoethyl)thiophene, 2-(3-Aminopropyl)thiophene, 3-(3-Aminopropyl)thiophene, 3-(2-Methylaminoethyl)thiophene, 2-Chloro-3-(2-aminoethyl)-thiophene, 2-Aminoethyl-4-methoxy-thiophene, 2-Amino-3-ethyl-thiophene, 2-(MethyIaminomethyl)thiophene, 3-(Aminomethyl) thiophene, 2-(2-Aminoethyl)-4-methoxy-thiophene, 1-(Aminomethyl)tetrazole, 1-(1-Aminoethyl)tetrazole, 1-(3-Aminopropyl)tetrazole, 5-Amino-3-methyl-isoxazole, 3-Aminopyridine, 4-Aminomethylthiazole, 2-(2-Aminoethyl)pyrazine, 2-(1-Aminoethyl)imidazole, 2-(Aminomethyl)isoxazole, 3-(2-Aminoethyl)pyrazole, 2-(Aminomethyl)-1,3,4-thiadiazole, 1,1-dimethylpropylamine, 1,1-dimethylprop-2-enylamine, 3,4,4-trichlorobut-3-enylamine, 1,1,2-trimethylprop-2-enylamine, 1,1-dimethyl-2-trifluoromethylprop-2-enylamine, 3-methyoxypropylamine, 1,1-dimethylbutylamine, 1,1-bis(fluoromethyl)ethylamine, 1,1-bis(fluoromethyl)-2-fluoroethylamine, 4,4,4-trifluorobutylamine, 2,2,3,3,3-pentafluoropropylamine, 3,3,4,4,4-pentafluorobutylamine, 5,5,5-trifuoropentylamine, 1-fluoromethyl-2-fluoroethylamine, 1-methyl-2,2,2-trifluoroethylamine, 2-fluoromethyl-3-fluoropropylamine, 1,1-dimethyl-2,2,2-trifluoroethylamine, 2,2-difluoropropylamine, 3,3-difluorobutylamine, 2,2-difluorobutylamine, 2-methyl-3,3,3-trifluoropropylamine, 2,2,3,3,4,4,4-heptafluorobutylamine, 2,2-difluoro-3-methylbutylamine, 2-methyl-3,3,3-trifluoropropylamine, 3-methylbutylamine, 1,1-dimethyl-2-oxo-4,4,4trifluorobutylamine, 1,1-dimethyl-2-oxo-5,5,5-trifluoropentylamine, 1,1,3-trimethyl-2-oxobutylamine, 1,1,3,3-tetramethyl-2-oxobutylamine, propyl 2-amino-2-methylpropanoate, isopropyl 2-amino-2-methylpropanoate, phenyl 2-amino-2-methylpropanoate, 1,1-bis (fluoromethyl)-2-oxo-4,4,4-trifluorobutylamine, 1,1-bis (fluoromethyl)-2-oxo-3,3-dimethylbutylamine, 2-amino-2, 2-bis(fluoromethyl)-(N-methyl-N-ethyl)acetamide, ethyl 2-amino-2,2-bis(fluoromethyl)acetate, propyl 2-amino-2,2-bis(fluoromethyl)acetate, isopropyl 2-amino-2,2-bis (fluoromethyl)acetate, phenyl 2-amino-2,2-bis (fluoromethyl)acetate, 1,1-dimethyl-2-oxopropylamine, 1,1-dimethyl-2-oxobutylamine, 1,1,3-trimethyl-2-oxobutylamine, α,α-dimethyl-β-oxophenethylamine, 2,3-dimethyl-3-hydroxy-2-butylamine.

EXAMPLE 304

General Procedure for Synthesis of Amide Derivatives of Compounds B and C

To a solution of 30 mg of compound B or C in 3 mL methylene chloride at 0° C. add 0.03 mL triethylamine and 12 mg N-hydroxybenzotriazole followed by 28 mg BOP reagent. Stir the solution for 10 minutes and then add 50 mg of an amine selected from Table 6. Stir overnight at 4° C. and then at room temperature for 2 hours. Pour the solution into 1/1 saturated sodium bicarbonate/brine. Extract the solution with methylene chloride and dry the combined organic layers over sodium sulfate. Remove the solids by filtration and concentrate the solution under reduced pressure. Pure product may be obtained following purification by flash chromatography, preparative TLC or reversed-phase liquid chromatography. Products may be characterized by proton NMR and/or mass spectrometry.

TABLE 6: Additional Amide Derivatives of Compounds B and C 2-(2-Hydroxyethoxy)ethylamine, 4-(2-Aminoethyl) morpholine, 1-(2-Aminoethyl)piperidine, 6-Amino-2-methylheptan-2-ol, 3-(Aminomethyl)pyridine, 3-Aminopropanol, 4-Aminobutanol, 5-Aminopentanol, 2-(2-Aminoethyl)piperidine, 1-(3-Aminopropyl)-2-pyrrolidinone, 1-(2-Aminoethyl)pyrrolidine, 2-Aminobutanol, 4-(Aminomethyl)pyridine, 2-Aminopyrazine, tert-Butylhydrazine, 6-Aminohexanol, 4-(3-Aminopropyl)morpholine, 3-Aminopropan-2-ol, 2-Aminopentanol, 1-Amino-1-hydroxymethyl-cyclopentane, 2-(Methylthio)ethylamine, 2-(Ethylthio) ethylamine, Thiomorpholine, 4-Amino-5-carboxamidoimidazole, 1-Aminopyrrolidine, 2-Amino-2-hydroxymethyl-propanol, trans-2-Aminocyclohexan-1-ol, 4-Aminobenzylamine, 2-(Aminomethyl)pyridine, 1-Aminomethylcyclohexan-1-ol, 2-Amino-1-methoxypropane, 2-Aminoimidazole, 4-Aminomorpholine, trans-4-Aminocyclohexan-1-ol, 4-Amino-1,2,4-triazole, 2-Amino-4,5-dihydrothiazole, 2-(Methanesulfonyl) ethylamine, 2-(Methanesulfinyl)ethylamine, 4-(2-Hydroxyethyl)aniline, 2-(2-Hydroxyethyl)aniline, 2-Amino-3-methylbutanol, Diallylamine, 2-(Methylamino) ethanol, O-Ethylhydroxylamine, 3-Amino-2-hydroxypropanol, O-Methylhydroxylamine, L-(Hydroxymethyl)pyrolidine, 2-Methoxyethylamine, N-Acetylethylenediamine, D-(Hydroxymethyl)pyrrolidine, 3-Hydroxypyrolidine, 2-(Aminoethyl)benzene, 2-Amino-2- methylpropanol, Cyclohexylamine, 3-Ethoxypropylamine, Allylamine, 2-Amino-2-hydroxymethyl-butanol, Propargylamine, 2-Fluoroethylamine, 3-(Dimethylamino) aniline, 2-Dimethylaminoethanol, 4-(2-hydroxyethyl) piperazine, 4-Ethylpiperazine, N-Ethylmethylamine, N-(Methyl)isopropylamine, 2,2,2-Trifluoroethylamine, N-Methylpropylamine, N-Methylbutylamine, N-Ethyl-2-methoxyethylamine, 4-(Aminoethyl)phenol, N-Methyl-2-methoxyethylamine, N-Ethylpropylamine, D,L-2-(Aminomethyl)tetrahydrofuran, 1-Aminopiperidine, D-Alanine methyl ester, 3,5-Diamino-1,2,4-triazole, Benzylsulfonamide, 4-Amino-4-methyl-pentan-2-one, 5-Aminouracil, Ethylamine, Norleucine methyl ester, 3-Methoxypropylamine, 3-Hydroxypiperidine, 4-Hydroxypiperidine, 1,1-Dimethylpropargylamine, N-(Ethyl)isopropylamine, Pentylamine, Piperidine, 2-Fluorophenylhydrazine, Hexylamine, Diethylamine, 4-(2-Aminoethyl)-1,2-dimethoxybenzene, 1-(2-Pyridyl) piperazine, 4-Methylpiperazine, 4-(2-Hydroxyethyl) morpholine, 4-Aminomethyl-1,2-methylenedioxybenzene, 1-((3,4-methylenedioxy)benzyl)piperazine, 4-(Ethylaminomethyl)pyridine, L-Valine methyl ester, D-Phenylalanine methyl ester, 4-(Methoxy)benzylamine, 1-Amino-4-(2-hydroxyethyl)piperazine, 1,2,3,6-Tetrahydropyridine, 3-(2-Aminoethyl)fluorobenzene, 1-Phenylpiperazine, 4-Amino-1-carboethoxypiperidine, 1-(Carboethoxy)piperazine, (R)-2-(Aminomethyl) tetrahydrofuran, (S)-2-(Aminomethyl)tetrahydrofuran, L-Valinol, D-Valinol, L-Alaninol, D-Phenylalaninol, 3,4-Dihydroxytetrahydrofuran, D-Alaninol, 2-Fluorobenzylamine, 4-Fluoroaniline, Isopropylamine, tert-Butylamine, iso-Butylamine, 4-(2-Aminoethyl) fluorobenzene, 4,5-Dihydro-5,5-dimethylimidazole, sec-Butylamine, Dimethylamine, (R)-3-Aminopropan-2-ol, Di-n-propylamine, n-Butylamine, 2-Methylpiperidine, 4–Chlorobenzylamine, 3-Phenylpropylamine, 2-Ethoxyethylamine, Methylpropargylamine, 2-(Trifluoromethyl)benzylamine, 4-Phenylbutylamine, O-Benzylhydroxylamine, 2,6-Difluorobenzylamine, 2-(Aminomethyl)thiophene, 2-(2-Aminoethyl)-1-methylpyrrole, (S)-N,alpha-Dimethylbenzylamine, 2-Amino-3-methylbutane, (S)-alpha-Methylbenzylamine, 1-Methylamino-2-phenylethane, 3,4-Dichlorobenzylamine, 1,4-Difluorobenzylamine, 2-(Aminomethyl)furan, 3-Fluorobenzylamine, 2,4-Dimethoxybenzylamine, N-Benzylmethylamine, N-Ethylbenzylamine, N-Methyl-2,2,2-trifluoromethylamine, 2,2,3,3,3-Pentafluoropropylamine, N-Methyl-2,2,3,3,3-pentafluoropropylamine, 1,1,1,3,3,3-Hexafluoroisopropylamine 2-Difluoro-3-Methoxy-1-methyl-propylamine, N-Methyl-1,1,1,3,3,3-hexafluoroisopropylamine, 1,1,1-Trifluoromethylpropylamine, 2-(3,3,3-Trifluoromethyl) propylamine, N-Methyl-1,1,1,3,3,3-hexafluoroisopropylamine, Di-(2,2,2-trifluoroethyl)amine, N-(2-Methoxyethyl)-2,2,2-trifluoroethylamine, 2-Methoxy-1-methylethylamine, 3-Methoxy-1-methyl-propylamine, 2-Methoxy-1-methylethylamine, N-Methyl-2-methoxy-1-benzyl-ethylamine, 1-Methoxymethyl-3-methyl-butylamine, Methylsulfonamide, Isopropylsulfonamide, Ethylsulfonamide, Benzylsulfonamide, sec-Butylsulfonamide, N-Methyl-ethylsulfonamide, N,1,1-Trimethylpropargylamine, N-Ethyl-1,1-dimethyl-propargylamine, N,1-Dimethyl-propargylamine, 1-Methyl-propargylamine, 1-Trifluoromethylpropargylamine, N,1,1-Trimethyl-propargylamine, N-Ethyl-1,1-dimethyl-propargylamine, N, 1-Dimethyl-propargylamine, N,1,1-Trimethyl-propargylamine, 1-Methyl-propargylamine, 1-Trifluoromethylpropargylamine, N-Ethylpropargylamine, N-(2-Methoxyethyl)propargylamine, 1-Amino-2-pentyne, 1-Amino-3-pentyne, 1-Amino-4-pentyne, 1-Methylamino-2-pentyne, 1-Methylamino-3-pentyne, 1-Methylamino-4-pentyne, 1-Ethylamino-4-pentyne, 1-Trifluoromethylamino-2-pentyne, 1-Trifluoromethylamino-3-pentyne, 1-Trifluoromethylamino-4-pentyne, N-(2-Methoxyethyl)-2-amino-1,1-dimethyl-2-butyne, 1-Amino-2-butyne, 1-Amino-3-butyne, N-Methylamino-2-butyne, N-Methylamino-3-butyne, 1-Ethylamino-3-butyne, 2-(Aminomethyl)dioxane,.2-(2-Aminoethyl)dioxane, 2-(3-Aminopropyl)dioxane, 2-(2-Aminopropyl)dioxane, 2-(Methylaminomethyl)dioxane, 2-(1-Aminoethyl)dioxane, 2-Aminomethyl-2H-tetrahydropyran, 2-(2-Aminoethyl)-2H-tetrahydropyran, 2-(3-Aminopropyl)-2H-tetrahydropyran, 2-(2-Aminopropyl)-2H-tetrahydropyran, 2-(2-Aminoethyl)-5-ethyl-2H-tetrahydropyran, 2-Methylaminomethyl-2H-tetrahydropyran, 2-(1-Aminoethyl)-2H-tetrahydropyran, 2-(2-Aminopropyl) tetrahydrofuran, 2-Aminomethyl-5-ethyl-tetrahydrofuran, 2-Methylaminomethyl-tetrahydrofuran, 2-(Ethylaminomethyl)tetrahydrofuran, 2-(1-Aminoethyl) tetrahydrofuran, 4-(Methoxymethyl)benzylamine, 4-(2-Methoxyethyl)benzylamine, 4-(Ethoxymethyl) benzylamine, 4-(Acetoxyoxymethyl)benzylamine, 3-(Dimethylaminomethyl)benzylamine, 4-(Sulfonamidomethyl)benzylamine, 2–Chloro-6-fluoro-benzylamine, 3-Chloro-4-fluoro-benzylamine, 2–Chloro-4-fluoro-benzylamine, 3,5-Difluoro-benzylamine, 2,4-Difluoro-benzylamine, Pentafluorobenzylamine, 4-Methoxy-2,3,5,6-tetrafluorobenzylamine, 4-(Methyl) benzylamine, Benzylamine, 4-(Ethyl)benzylamine, 4-(Ethoxy)benzylamine, 4-(Isopropyl)benzylamine, 4-(Isobutyl)benzylamine, 4-(Isopropoxy)benzylamine, 4-(Isobutoxy)benzylamine, 4-(Allyl)benzylamine, 4-(Allyloxy)benzylamine, 4-(3,3,1,1-Tetrafluoroallyloxy) benzylamine, 4-(Trifluoromethoxy)benzylamine, 4-(2,2,2-trifluoroethoxy)benzylamine, 3,4-Ethylenedioxybenzylamine, 4-Methoxymethyl-2-chlorophenethylamine, 4-(2-Methoxyethyl)phenethylamine, 4-(Ethoxymethyl)phenethylamine, 4-(Acetoxyoxymethyl) phenethylamine, 3-(Dimethylaminomethyl) phenethylamine, 1-Phenyl-2,2,2-trifluoroethylamine, 4-(Trifluoromethoxy)aniline, 4-Methoxyaniline, 4-Ethoxyaniline, 3–Chloro-4-fluoro-aniline, 4–Chloro-2-fluoro-aniline, 4-(Acetoxy)aniline, 4-(Butoxy)aniline, 3-Chloroaniline, 4-(Methylthio)aniline, 5-(Aminomethyl) benzofuran, 5-(Methylaminomethyl)benzofuran, 4-(1-Aminoethyl)benzofuran, 5-(2-Aminoethyl)benzofuran, 5-Aminomethyl-2,3-dihydro-benzofuran, 5-Methylaminomethyl-2,3-dihydro-benzofuran, 4-1-Aminoethyl-2,3-dihydro-benzofuran, 5-2-Aminoethyl-2,3-dihydro-benzofuran, 5-Aminomethyl-2H-tetrahydrobenzopyran, 5-Methylaminomethyl-2H-tetrahydrobenzopyran, 4-1-Aminoethyl-2H-tetrahydrobenzopyran, 5-2-Aminoethyl-2H-tetrahydrobenzopyran, 5-Aminomethyl-2H-tetrahydrobenzopyran, 5-Methylaminomethyl-2H-tetrahydrobenzopyran, 4-(1-Aminoethyl)-2H-tetrahydrobenzopyran, 5-(2-Aminoethyl)-2H-tetrahydrobenzopyran, 5-Aminomethyl-benzo-1,4-dioxane, 5-Methylaminomethyl-benzo-1,4-dioxane, 4-1-Aminoethyl-benzo-1,4-dioxane, 5-2-Aminoethyl-benzo-1,4-dioxane, 5-Aminomethyl-benzo-1,4-dioxane, 5-Methylaminomethyl-benzo-1,4-dioxane, 4-(1-Aminoethyl)-benzo-1,4-dioxane, 5-(2-Aminoethyl)-benzo-1,4-dioxane, 3-Amino-5-methoxy-thiophene, 2-Amino-5- chloro-thiophene, 2-(2-Aminoethyl)thiophene, 2-(3-Aminopropyl)thiophene, 3-(3-Aminopropyl)thiophene, 3-(2-Methylaminoethyl)thiophene, 2–Chloro-3-(2-aminoethyl)-thiophene, 2-Aminoethyl-4-methoxy-thiophene, 2-Amino-3-ethyl-thiophene, 2-(Methylaminomethyl)thiophene, 3-(Aminomethyl) thiophene, 2-(2-Aminoethyl)-4-methoxy-thiophene, 1-(Aminomethyl)tetrazole, 1-(l-Aminoethyl)tetrazole, 1-(3-Aminopropyl)tetrazole, 5-Amino-3-methyl-isoxazole, 3-Aminopyridine, 25 4-Aminomethylthiazole, 2-(2-Aminoethyl)pyrazine, 2-(1-Aminoethyl)imidazole, 2-(Aminomethyl)isoxazole, 3-(2-Aminoethyl)pyrazole, 2-(Aminomethyl)-1,3,4-thiadiazole.

EXAMPLE 305

Methyl 29,30,31,32-tetrahydro-nodulisporate

To 1.3 mg methyl nodulisporate in 2 mL 1:1 benzene/water at room temperature was added 1 drop Adogen® 464 (Aldrich Chemical Co., Milwaukee, Wis.), 10 mg $NaHCO_3$ and 10 mg $Na_2S_2O_4$. The solution was heated to 80° C. for 10 minutes. The reaction was cooled to room temperature, extracted with ethyl acetate, dried with $Na_2SO_4$, filtered and concentrated under reduced pressure. Purified product was obtained following preparative TLC (1×0.5 mm silica gel) using 6:4 EtOAc/hexanes as eluant. The purified product was characterized by $^1$H NMR.

EXAMPLE 306

N-(2-Tetrahydrofuranylmethyl)-29,30,31,32-tetrahydro-nodulisporamide

To 40 mg N-(2-tetrahydrofuranylmethyl)-nodulisporamide in 2 mL methanol at room temperature was added 20 mg 10% Pd on carbon. One atmosphere of hydrogen was established and maintained for 2 hours using a balloon. After removal of the catalyst by filtration through Celite using methanol as eluant, the solution was concentrated under reduced pressure and 3 mg pure product was obtained following preparative TLC on silica gel (two 1000 micron plates). The product was characterized by NMR and mass spectrometry (m/z: 767 (M +1)).

EXAMPLE 307

N-Ethyl-N-methyl-29,30,31,32-tetrahydro-nodulisporamide

To 23 mg of N-ethyl-N-methyl-nodulisporamide in 2 mL methanol at room temperature was added 40 mg 10% Pd on carbon. One atmosphere of hydrogen was established and maintained for 3 hours using a balloon. After removal of the catalyst by filtration through Celite using methanol as eluant, the solution was concentrated under reduced pressure and 9.5 mg of reduced product was obtained following medium pressure liquid chromatography (93/7 methanol/water as eluant). The product was characterized by proton NMR and mass spectrometry (m/z: 723 (M+1)).

EXAMPLE 308

General Procedure for the Preparation of 29,30,31,32-Tetrahydro-nodulisporic Acid Derivatives Place 50 mg of a nodulisporamide or nodulisporate analog prepared from the amines listed in Table 6 or the alcohols listed in Table 2 in 4 mL methanol at room temperature. Hydrogenation may be accomplished using 10% Pd on carbon under 1 atmosphere of hydrogen from 15 minutes to 24 hours. The catalyst may be removed by filtration through a pad of Celite using methanol as eluant. Concentration of the solution under reduced pressure followed by purification on silica gel by either flash chromatography, preparative TLC or by reversed-phase liquid chromatography will yield the desired corresponding 29,30,31,32-tetrahydro derivative.

Alternatively, place 50 mg nodulisporic acid in 4 mL methanol at room temperature. Add 1 to 50 mg 10% Pd on carbon and establish an atmosphere of hydrogen using a balloon for 15 minutes to 24 hours. The catalyst may be subsequently removed by filtration through a pad of Celite using methanol as eluant. Concentration of the solution under reduced pressure followed by purification on silica gel by either flash chromatography, preparative TLC or by reversed-phase liquid chromatography will yield the desired corresponding 29,30,31,32-tetrahydro-nodulisporic acid. The 29,30,31,32-tetrahydro-nodulisporic acid thus obtained may be coupled to the amines in Table 6 or the alcohols listed in Table 2 to form the desired 29,30,31,32-tetrahydro-amide and ester derivatives.

EXAMPLE 309

29,30-Dihydro-nodulisporic acid

To 1 mg of nodulisporic acid in 1 mL of dichloromethane was added 1.6 mg of Wilkinson's catalyst. The mixture was stirred under a balloon atmosphere of hydrogen overnight (18 h). HPLC separation was obtained with a Magnum 9-ODS reverse phase column and 85:15 methanol:water to 100% methanol gradient. The purified product was isolated upon evaporation of the solvent and characterized by its $^1$H NMR.

EXAMPLE 311

General Procedure for the Preparation of 29,30-Dihydro-Nodulisporic Acid Derivatives To a solution of 30 mg of 29,30-dihydro-nodulisporic acid in 3 mL methylene chloride at 0° C. add 0.03 mL triethylamine and 12 mg N-hydroxybenzotriazole followed by 28 mg BOP reagent. Stir the solution for 10 minutes and then add 50 mg of an amine or an alcohol selected Li from Table 6. Stir overnight at 4° C. and then at room temperature for 2 hours. Pour the solution into 1/1 saturated sodium bicarbonate/brine. Extract the solution with methylene chloride and dry the combined organic layers over sodium sulfate. Remove the solids by filtration and concentrate the solution under reduced pressure. Pure product may be obtained following purification by flash chromatography, preparative TLC or reversed-phase liquid chromatography. Products may be characterized by proton NMR and or mass spectrometry.

EXAMPLE 312

General Procedure for the Preparation of 31,32-Dihydro-Compound B Derivatives

Place 50 mg of a ester or amide analog prepared from compound B and the amines listed in Table 6 or alcohols listed in Table 2 in 4 mL methanol at room temperature. Hydrogenation of the 31,32-double bond may be accomplished using 10% Pd on carbon under 1 atmosphere of hydrogen from 15 minutes to 24 hours. The catalyst may be removed by filtration through a pad of Celite using methanol as eluant. Concentration of the solution under reduced pressure followed by purification on silica gel by either flash chromatography, preparative TLC or by reversed-phase liquid chromatography will yield the desired 31,32-dihydro-Compound B derivative.

Alternatively, place 50 mg compound B in 4 mL methanol at room temperature. Add 1 to 50 mg 10% Pd on carbon and establish an atmosphere of hydrogen using a balloon for 15 minutes to 24 hours. The catalyst may be subsequently removed by filtration through a pad of Celite using methanol as eluant. Concentration of the solution under reduced pressure followed by purification on silica gel by either flash chromatography, preparative TLC or by reversed-phase liquid chromatography will yield the desired corresponding 31,32-dihydro-compound B. The 31,32-dihydro-compound B thus formed may be coupled to the amines listed in Table 6 and the alcohols listed in Table 2 to form the desired 31,32-dihydro-compound B amides and esters.

EXAMPLE 313

Nodulisporyl azide

To 1 mg of nodulisporic acid in 0.2 mL chloroform was added 50 μL triethylamine and 20 μL of diphenylphosphoryl azide. The reaction mixture was stirred at room temperature for 3 h before purification on silica gel (preparative TLC, 1×0.5 mm silica gel) using 1:1 EtOAc/hexanes to yield 0.8 mg of pure product which was characterized by $^1$H NMR and mass spectrometry.

EXAMPLE 314

29,30-Dihydro-20,30-oxa-nodulisporyl azide

To 1 mg 29,30-dihydro-20,30-oxa-nodulisporic acid in 0.2 mL chloroform add 0.05 mL triethylamine followed by 0.02 mL diphenylphosphoryl azide. Stir the reaction at room temperature for 3 h before purification by flash chromatography or preparative TLC on silica gel. The product which is obtained may be characterized by proton NMR and mass spectrometry.

EXAMPLE 315

29,30-Dihydro-20,30-oxa-32-descarboxy-32-isocyanato-nodulisporic acid

Heat 20 mg of 29,30-dihydro-20,30-oxa-nodulisporyl azide in 8 mL toluene to 90° C. for 2 h. The solvent may be removed by evaporation and the product which is obtained may be characterized by proton NMR and mass spectrometry.

EXAMPLE 316

32-Descarboxy-32-isocyanato-nodulisporic acid

A solution of 54 mg of nodulisporyl azide in toluene was heated at 90° C. for 2 h. The solvent was then evaporated and the isocyanate product was obtained in quantitative yield and was characterized by $^1$H NMR and mass spectrometry.

EXAMPLE 317

32-Descarboxy-32-(1-carbomethoxyamino)-nodulisporic acid

To 1.3 mg of isocyanate of Example 313 in 1 mL of methanol was added 20 microliters of triethylamine. The reaction mixture was heated for 45 min at 75° C. and the carbamate product (0.7 mg) was isolated by preparative TLC on silica gel (1×0.5 mm) and characterized by $^1$H NMR and mass spectrometry.

EXAMPLE 318

32-Descarboxy-32-(1-(3-benzyl)urea)-nodulisporic acid

To 1 mg of isocyanate of Example 313 in 0.2 mL of toluene was added 40 microliters of benzylamine. The mixture was stirred at 20° C. for 20 min and the urea product (0.2 mg) was isolated by preparative TLC (1×0.5 mm silica gel, 1:3 hexane:EtOAc) and characterized by its $^1$H NMR and MS.

The general procedure of Example 318 was repeated using the appropriate amino to provide urea compounds of Table 7.

TABLE 7

32-Descarboxy-32-[UREA]-Nodulisporic Acid Derivatives

| Example | Urea |
|---|---|
| 319 | NHC(O)-morpholinyl |
| 320 | NHC(O)NHCH$_2$Ph(4-OMe) |
| 321 | NHC(O)NHCH(Me)$_2$ |
| 322 | NHC(O)NH(CH$_2$)$_5$NH$_2$ |
| 323 | NHC(O)NHCH$_2$CH$_2$OH |
| 333 | NHC(O)NHCH$_2$CH$_2$CH$_2$NMe$_2$ |
| 334 | NHC(O)NHCH$_2$CH$_2$CH$_2$-1-morpholinyl |
| 335 | NHC(O)NHCH$_2$-(2-pyridyl) |
| 336 | NHC(O)NHCH$_2$CH$_2$-piperazinyl |

EXAMPLE 337

General Procedure for the Synthesis of 32-Descarboxy-32-[UREA]- or 32-Descarboxy-32-[CARBAMATE]-Nodulisporic Acid Derivatives To 1 mg of isocyanate of Example 313 in 0.2 mL of toluene add 40 mg of an amine selected from Table 6 or alcohol selected from Table 2. Stir the mixture at 20° C. from 20 minutes to 24 hours. Pure urea or carbamate product may be isolated by flash chromatography, preparative TLC or reversed-phase liquid chromatography. The purified products may be characterized by proton NMR and mass spectrometry.

EXAMPLE 338

29,30-Dihydro-20,30-oxa-32-descarboxy-32-isocyanato-nodulisporic acid

Heat a solution of 54 mg of 29,30-dihydro-20,30-oxa-nodulisporyl azide in toluene at 90° C. for 2 h. Evaporate the solvent and the isocyanate product thus obtained may be characterized by $^1$H NMR and mass spectrometry.

EXAMPLE 339

General Procedure for the Synthesis of 29,30-Dihydro-20,30-oxa-32-descarboxy-32-[UREA]- or 29,30-Dihydro-20,30-oxa-32-descarboxy-32-[CARBAMATE]-Nodulisporic Acid Derivatives To 1 mg of 29,30-dihydro-20,30-oxa-32-descarboxy-32-isocyanato-nodulisporic acid in 0.2 mL of toluene add 40 mg of an amine selected from Table 6 or alcohol selected from Table 2. Stir the mixture at 20° C. from 20 minutes to 24 hours. Pure urea or carbamate product may be isolated by flash chromatography, preparative TLC or reversed-phase liquid chromatography. The purified products may be characterized by proton NMR and mass spectrometry.

EXAMPLE 340

31-Hydroxy-20,30-oxa-29,30,31,32-tetrahydro-nodulisporyl azide

To 1 mg 31-hydroxy-20,30-oxa-29,30,31,32-tetrahydro-nodulisporic acid in 0.2 mL chloroform add 0.05 mL triethylamine followed by 0.02 mL diphenylphosphoryl azide. Stir the reaction at room temperature for 3 h before purification by flash chromatography or preparative TLC on silica gel. The product which is obtained may be characterized by proton NMR and mass spectrometry.

EXAMPLE 341

31-Hydroxy-20,30-oxa-29,30,31,32-tetrahydro-32-descarboxy-32-isocyanato-nodulisporic acid Heat a solution of 54 mg of 3 1-hydroxy-20,30-oxa-29,30,31,32-tetrahydro-nodulisporyl azide in toluene at 90° C. for 2 h. Evaporate the solvent and the isocyanate product thus obtained may be characterized by $^1$H NMR and mass spectrometry.

EXAMPLE 342

General Procedure for the Synthesis of 31-Hydroxy-20,30-oxa-32-descarboxy-32-[UREA]-29,30,31,32-tetrahydro- or 31-Hydroxy-20,30-oxa-32-descarboxy-32-[CARBAMATE]-29,30,31,32-tetrahydro-nodulisporic acid Derivatives To 1 mg of 31-hydroxy-20,30-oxa-29,30,31,32-tetrahydro-32-descarboxy-32-isocyanato-nodulisporic acid in 0.2 mL of toluene add 40 mg of an amine selected from Table 6 or alcohol selected from Table 2. Stir the mixture at 20° C. from 20 minutes to 24 hours. Pure urea or carbamate product may be isolated by flash chromatography, preparative TLC or reversed-phase liquid chromatography. The purified products may be characterized by proton NMR and mass spectrometry.

EXAMPLE 343

1-Hydroxy-nodulisporic acid

To 2.8 mg of nodulisporic acid in 0.8 mL of THF at 0° C. under argon was added 100 microliters of 2.0 M lithium borohydride in THF. The reaction was quenched with 400 microliters of 2N HCl after 5 min at 0° C. and the products were extracted with EtOAc. The extracts were dried over sodium sulfate and concentrated in vacuo. The reside was purified by preparative TLC (1 x 0.5 mm silica gel plate, 95:5:0.5 dichloromethane:methanol:acetic acid) to yield 0.8 mg of isomer A and 0.6 mg of isomer B characterized by their $^1$H NMR and MS.

EXAMPLE 344

1-Hydroxy-nodulisporic acid, methyl ester

To 0.5 mg methyl nodulisporate in 1 mL methanol at 0° C. was added 1 mg sodium borohydride. After 10 min at 0° C., the solution was purified by reversed-phase HPLC without workup using 30:70 to 15:85 (25 minute linear gradient) water/methanol to yield pure product. The product was characterized by $^1$H NMR.

EXAMPLE 345

N-Ethyl-N-methyl- 1 -hydroxy-nodulisporamide

To 30 mg N-ethyl-N-methyl-nodulisporamide in 2 mL tetrahydrofuran at room temperature was added 1 mL diisobutylaluminum hydride (1.0 M solution in hexanes). After 3 days at room temperature, the reaction was quenched by the addition of acetic acid. The solution was washed with saturated sodium bicarbonate and brine, dried over sodium sulfate and evaporated to dryness. The residue was purified by flash chromatography on silica gel using 1/1 acetone/hexanes as eluant. The purified product was characterized by proton NMR and mass spectrometry (m/z: 723 (M+1)).

EXAMPLE 346

1-Hydroxy-Compound B or C

To 5 mg of Compound B or C in 2 mL of methanol at 0° C. under argon add 5 mg of sodium borohydride. After 10 min at 0° C., extract the products with methylene chloride. Dry the combined extracts over sodium sulfate and concentrate the solution in vacuo. The residual solid may be purified purified by flash chroimatography, preparative TLC or reversed-phase liquid chromatography to yield 1-hydroxy-Compound B or C as a mixture of stereoisomers which may be characterized by proton NMR and mass spectrometry.

EXAMPLE 347

General Procedure for Synthesis of 1-Hydroxy-Amide and Ester Derivatives of Compounds A, B and C To a solution of 30 mg of 1-hydroxy-Compound A, B or C in 3 mL methylene chloride at 0° C. add 0.03 mL triethylamine and 12 mg N-hydroxybenzotriazole followed by 28 mg BOP reagent. Stir the solution for 10 minutes and then add 50 mg of an amine selected from Table 6 or an alcohol selected from Table 2. Stir overnight at 4° C. and then at room temperature for 2 hours. Pour the solution into 1/1 saturated sodium bicarbonate/brine. Extract the solution with methylene chloride and dry the combined organic layers over sodium sulfate. Remove the solids by filtration and concentrate the solution under reduced pressure. Pure product may be obtained following purification by flash chromatography, preparative TLC or reversed-phase liquid chromatography. Products may be characterized by proton NMR and/or mass spectrometry.

EXAMPLE 348

1-Hydroxy-1-methyl-nodulisporic acid

To 0.5 mL of 1.4 M methylmagnesium bromide in THF/toluene at 0° C. was added 1 mg of nodulisporic acid dissolved in 0.6 mL of THF. After 10 min, the reaction was quenched with 2N HCl and extracted with EtOAc. Preparative TLC (1×0.5 mm silica gel plate, 95:5:0.5 dichloromethane:methanol:acetic acid) gave 0.8 mg of product characterized by its $^1$H NMR.

EXAMPLE 349

1-Hydroxy-1-methyl-nodulisporic acid, methyl ester

To 1.2 mg of methyl nodulisporate in 1 mL of THF under argon at −78° C. was added 0.5 mL of 1.4M methylmagnesium bromide in THF/toluene. The mixture was stirred for 15 min before an aqueous solution of ammonium chloride was added. The mixture was extracted with EtOAc. Preparative TLC (1×0.5 mm silica gel plate, 2:3 hexane:EtOAc) gave 1 mg of the titled product characterized by its $^1$H NMR.

EXAMPLE 350

1-Hydroxy-1-Alkyl- or 1-Hydroxy-1-Aryl-Compounds A, B or C

To 0.5 mL solution of 1.0 M Grignard reagent selected from Table 8 in 1/1 THF/toluene at 0° C. add 1 mg Compound A, B or C dissolved in 0.6 mL THF. After 10 min at 0° C., quench the reaction with 2N HCl and extract with methylene chloride. Dry the combined organic layers over sodium sulfate, filter and concentrate under reduced pressure. Pure product may be obtained following flash chromatography, preparative TLC or reversed-phase liquid chromatography. Purified products may be characterized by proton NMR or mass spectrometry.

Table 8: Grignard Reagents
Methyl magnesium bromide
Ethyl magnesium chloride
iso-Propyl magnesium bromide
Phenyl magnesium iodide
Benzyl magnesium bromide
Allyl magnesium bromide
Propargyl magnesium bromide
Magnesium bromide acetilide

EXAMPLE 351

1-Hydroxy-32-descarboxy-32-hydroxymethyl-nodulisporic acid

To 1.2 mg methyl nodulisporate in 1.2 mL tetrahydrofuran at −78° C. was added 20 μL 1M lithium aluminum hydride in tetrahydrofuran. The yellow color rapidly disappeared. After 10 minutes, the reaction was quenched at −78° C. by dropwise addition of saturated $Na_2SO_4$. The solution was extracted with ethyl acetate, dried with $Na_2SO_4$, filtered and concentrated under reduced pressure. Pure product was obtained following preparative TLC (1×0.25 mm silica gel plate) using 85:15 EtOAc/hexanes as eluant. The purified product was characterized by $^1$H NMR.

EXAMPLE 352

31,32-Dihydro-31,32-dihydroxy-nodulisporic acid and Aldehyde (Compound IV)

To 3 mg of nodulisporic acid was added 1 mL of methanol and 100 microliters of 0.04 M $OsO_4$ in t-butanol stabilized with 1% t-butyl hydroperoxide. After 50 min at room temperature, 400 mg of sodium sulfite in 2 mL of water was then added to the reaction mixture and stirring was continued for another 20 minutes. The mixture was then extracted with EtOAc and the crude products were purified by preparative TLC (1×0.5 mm silica gel plate) eluted in 95:5:0.5 dichloromethane:methanol:acetic acid to yield the title compound (1 mg isomer A and 0.6 mg isomer B) and 0.5 mg of aldehyde derived from nodulisporic acid (Compound IV), each characterized by $^1$H NMR.

EXAMPLE 353

General Procedure for the Preparation of Ester and Amide Derivatives of 31,32-Dihydro-31,32-dihydroxy-nodulisporic acid To a solution of 30 mg of 31,32-dihydro-31,32-dihydroxy-nodulisporic acid in 3 mL methylene chloride at 0° C. add 0.03 mL triethylamine and 12 mg N-hydroxybenzotriazole followed by 28 mg BOP reagent. Stir the solution for 10 minutes and then add 50 mg of amine listed in Table 6 or an alcohol listed in Table 2. Stir the solution overnight at 4° C. and then pour into 1/1 saturated sodium bicarbonate/brine, extract with methylene chloride and dry the combined organic layers over sodium sulfate. Remove the solids by filtration and concentrate the solution to dryness under reduced pressure. Pure product may be obtained by flash chromatography or preparative TLC on silica gel or reversed-phase liquid chromatography. The purified product may be characterized by proton NMR and mass spectrometry.

EXAMPLE 354

4,20-bis-O-Acetyl-nodulisporic acid

To 1.2 mg of nodulisporic acid was added 300 microliters of acetic anhydride and 100 microliters of pyridine. The reaction mixture was heated at 65° C. for 1 h and excess solvent was removed in vacuo. The residual solid was purified by preparative TLC on silica gel eluted with 95:5 dichloromethane:methanol to yield 1.2 mg of the bis-acetate characterized by its $^1$H NMR.

EXAMPLE 355

N-Ethyl-N-methyl-20-dimethylaminocarbonyloxy-nodulisporamide

To 30 mg N-ethyl-N-methyl-nodulisporamide in 3 mL methylene chloride at 4° C. was added 60 mg carbonyldiimidazole. After 3 days at 4° C., 1 mL dimethylamine (25% in water) was added and the solution stirred for an additional 4 days. The solution was poured into brine, extracted with methylene chloride, dried with sodium sulfate and evaporated to dryness. Product was partially purified by flash chromatography on silica gel using 4/6 acetone/hexanes as eluant. Additional purification using medium pressure liquid chromatography (92/8 methanol/water as eluant) yielded 18 mg pure product. The purified product was characterized by proton NMR and mass spectrometry (m/z: 792 (M+1)).

EXAMPLE 356

N-Ethyl-N-methyl-1-desoxo-1-methoximino-nodulisporamide

To a solution of 30 mg N-ethyl-N-methyl-nodulisporamide and 30 mg methoxyamine hydrochloride in 4 mL ethanol was added 0.1 mL pyridine. The solution was heated to reflux for 2 days, cooled to room temperature and concentrated under reduced pressure. The residue was diluted with methylene chloride, washed with brine, dried over sodium sulfate and concentrated to dryness. The residue was purified by preparative TLC on silica gel (two 1000 micron plates) using ⅑ methanol/methylene chloride as eluant. The purified products (26 mg), as a mixture of E- and Z-methoximes, were characterized by proton NMR and mass spectrometry (m/z: 732,(M+1−1$H_2$O)).

EXAMPLE 357

N-Ethyl-N-methyl-i-desoxo-1-oximino-nodulisporamide

To a solution of 20 mg N-ethyl-N-methyl-nodulisporamide and 20 mg hydroxylamine hydrochloride in 2 mL ethanol at room temperature was added 0.02 mL pyridine. The solution was heated to reflux for 15 hours, cooled to room temperature and diluted with methylene chloride. The solution was washed with brine, dried over sodium sulfate and concentrated to dryness. The residue was purified by preparative TLC on silica gel (two 1000 micron plates) using ⅑ methanol/methylene chloride as eluant to yield 17 mg desired product as a mixture of E- and Z-oxime isomers. The purified products were characterized by proton NMR and mass spectrometry (m/z: 718 (M+1−1$H_2$O)).

EXAMPLE 358

General Procedure for the Preparation of 1-Oximino Derivatives of Compounds A, B and C To a solution of 20 mg of compound A, B or C and 20 mg hydroxylamine derivative selected from Table 9 in 2 mL ethanol at room temperature, add 0.02 mL pyridine. Heat the solution to reflux for 15 minutes to 24 hours, then cool to room temperature and dilute with methylene chloride. The solution may be washed with brine, the organic layer dried over sodium sulfate and concentrated to under reduced pressure. Pure product may be obtained following purification by flash chromatgraphy or preparative TLC on silica gel or reversed-phase liquid chromatography as a mixture of E- and Z-oxime isomers. The purified products may be characterized by proton NMR and mass spectrometry. Similarly, amide and ester derivatives of compounds A, B and C, prepared using the amines listed in Table 6 and alcohols in Table 2, may be substituted for compounds A, B and C in the above procedure.

Table 9: Oxime Reagents
Hydroxylamine
O-Methylhydroxylamine
O-Ethylhydroxylamine
O-Benzylhydroxylamine
O-tert-Butylhydroxylamine
O-(Pentafluorobenyzl)hydroxylamine
O-Allylhydroxylamine
O-Phenylhydroxylamine
O-iso-Butylhydroxylamine
O-(2–Chloro-6-fluoro-benzyl)hydroxylamine
O-(4Methoxybenzyl)hydroxylamine

EXAMPLE 359

General Procedure for the Preparation of Hydrazinyl Derivatives of Compounds A, B and C To a solution of 20 mg of compound A, B or C and 20 mg hydrazine selected from Table 10 in 2 mL ethanol at room temperature, add 0.02 mL pyridine. Heat the solution to reflux for 15 minutes to 24 hours, then cool to room temperature and dilute with methylene chloride. The solution may be washed with brine, the organic layer dried over sodium sulfate and concentrated to under reduced pressure. Pure product may be obtained following purification by flash chromatgraphy or preparative TLC on silica gel or reversed-phase liquid chromatography as a mixture of E- and Z-oxime isomers. The purified products may be characterized by proton NMR and mass spectrometry. Similarly, amide and ester derivatives of compounds A, B and C, prepared using the amines listed in Table 6 and alcohols in Table 2, may be substituted for compounds A, B and C in the above procedure.

Table 10: Hydrazine Reagents
Methylhydrazine
N,N-Dimethylhydrazine
tert-Butylhydrazine
4-Amino-morpholine
1-Amino-pyrrolidine
1-Amino-piperidine
Phenylhydrazine
4-(Methyl)phenylhydrazine
Benzylhydrazine
Ethyl hydrazinoacetate
2-(Fluoro)phenylhydrazine
1-Amino-4-methyl-piperazine
1-Amino-4-(2-hydroxyethyl)piperazine
2,5-Dichlorophenylhydrazine
Methanesulfonyl hydrazide
iso-Propylsulfonyl hydrazide
Benzenesulfonyl hydrazide

EXAMPLE 360

N-Ethyl-N-methyl-26-epi-nodulisporamide

To a solution of 5 mg N-ethyl-N-methyl-nodulisporamide in 2 mL acetonitrile was added 1 mL triethylamine. The solution was heated to reflux for 20 hours. The solution was concentrated to dryness under reduced pressure. The residue was purified by flash chromatography on silica gel using 1/9 methanol/methylene chloride to yield the desired product, which was characterized by proton NMR.

The general procedure of Example 40 was repeated using the appropriate amines listed in Table 11 below to provide the corresponding monosubstituted nodulisporamide compounds. These compounds were characterized by proton NMR and/or mass spectrometry (unless otherwise specified, m/z is for M+1).

TABLE 11

Additional Monosubstituted Aliphatic Nodulisoproamide Derivatives

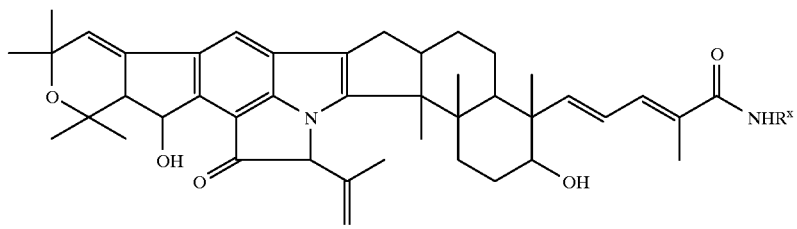

| Ex. | m/z | Amines | R$^x$ |
|---|---|---|---|
| 361 | 774.9 | 3,3,3-triflurorpropylamine | $CH_2CH_2CF_3$ |
| 362 | 779.0 | methyl 2-amino-2-methyl-propanoate | $C(CH_3)_2CO_2CH_3$ |
| 363 | 793.1 | ethyl 2-amino-2-methyl-propanoate | $C(CH_3)_2CO_2CH_2CH_3$ |
| 364 | 792.1 | 2-amino-2-methyl-(N,N-dimethyl)propanamide | $C(CH_3)_2CON(CH_3)_2$ |
| 365 | 846.1 | 2-amino-2-methyl-(N-(2,2,2-trifluoroethyl))propanamide | $C(CH_3)_2CONHCH_2CF_3$ |

TABLE 11-continued

Additional Monosubstituted Aliphatic Nodulisoproamide Derivatives

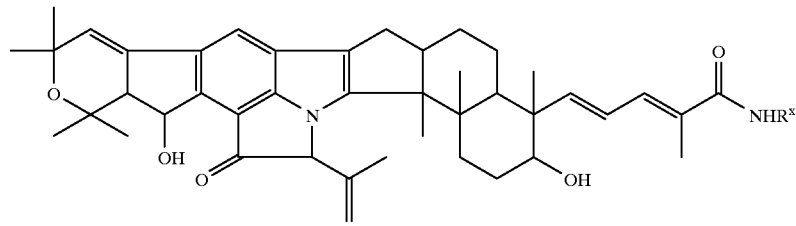

| Ex. | m/z | Amines | $R^x$ |
|---|---|---|---|
| 366 | 806.1 | 2-amino-2-methyl-(N-ethyl-N-methyl)propanamide | $C(CH_3)_2CON(CH_3)CH_2CH_3$ |
| 367 | 756.9 | 1,3-difluoro-2-propylamine | $CH(CH_2F)_2$ |
| 368 | 818.1 | N-(2-amino-2-methyl-propanoyl)pyrrolidine | 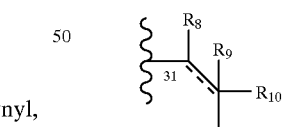 |
| 369 | 815.0 | methyl 2-amino-2,2-bis(fluoromethyl)acetate | $C(CH_2F)_2CO_2CH_3$ |
| 370 | 753.5 | 1,1-dimethyl-2-fluoroethylamine | $C(CH_3)_2CH_2F$ |

What is claimed is:

1. A compound having the formula I:

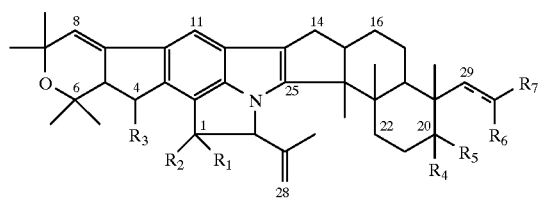

wherein $R_1$ is (1) hydrogen,
(2) optionally substituted $C_1$–$C_{10}$ alkyl,
(3) optionally substituted $C_2$–$C_{10}$ alkenyl,
(4) optionally substituted $C_2$–$C_{10}$ alkynyl,
(5) optionally substituted $C_3$–$C_8$ cycloalkyl,
(6) optionally substituted $C_5$–$C_8$ cycloalkenyl
where the substitutents on the alkyl, alkenyl, alkynyl, cycloalkyl and cycloalkenyl are 1 to 3 groups independently selected from
  (i) $C_1$–$C_5$ alkyl,
  (ii) X—$C_1$–$C_{10}$ alkyl, where X is O or $S(O)_m$.
  (iii) $C_3$–$C_8$ cycloalkyl,
  (iv) hydroxy,
  (v) halogen,
  (vi) cyano,
  (vii) carboxy,
  (viii) $NY^1Y^2$, where $Y^1$ and $Y^2$ are independently hydrogen or $C_1$–$C_{10}$ alkyl,
  (ix) $C_1$–$C_{10}$ alkanoylamino, and
  (x) aroyl amino wherein said aroyl is optionally substituted with 1 to 3 groups independently selected from $R^f$ (7) aryl $C_0$–$C_5$ alkyl wherein said aryl is optionally substituted with 1 to 3 groups independently selected from $R^f$,
(8) $C_1$–$C_5$ perfluoroalkyl
(9) a 5-membered heterocycle containing 1 heteroatom selected from oxygen, sulfur and nitrogen atoms optionally substituted by 1 to 3 groups independently selected from hydroxy, oxo, $C_1$–$C_{10}$ alkyl and halogen, and which may be saturated or partly unsaturated, $R_2$, $R_3$, and $R_4$ are independently $OR^a$, $OCO_2R^b$, $OC(O)NR^cR^d$; or $R_1+R_2$ represent =O, =$NOR^a$ or =N—$NR^cR^d$;

$R_5$ and R6 are hydrogen; or

R5 and R6 together represent —O—;

$R_7$ is (1) CHO, or
(2) the fragment

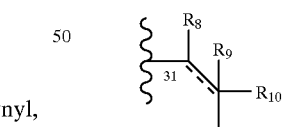

$R_8$ is (1) hydrogen,
(2) $OR^a$, or
(3) $NR^cR^d$ $R_9$ is (1) hydrogen, or
(2) $OR^a$;

$R_{10}$ is (1) CN,
(2) $C(O)OR^b$,
(3) $C(O)N(OR^b)R^c$,
(4) $C(O)NR^cR^d$,
(5) $NHC(O)OR^b$,
(6) $NHC(O)NR^cR^d$, (7) $CH_2OR^a$,
(8) $CH_2OCO_2R^b$,
(9) $CH_2OC(O)NR^cR^d$,
(10) $C(O)NR^cNR^cR^d$, or
(11) $C(O)NR^cSO_2R^b$;

---- represents a single or a double bond;

$R^a$ is (1) hydrogen,
(2) optionally substituted $C_1$–$C_{10}$ alkyl,
(3) optionally substituted $C_3$–$C_{10}$ alkenyl,
(4) optionally substituted $C_3$–$C_{10}$ alkynyl,
(5) optionally substituted $C_{1-10}$ alkanoyl,
(6) optionally substituted $C_3$–$C_{10}$ alkenoyl,
(7) optionally substituted $C_3$–$C_{10}$ alkynoyl,
(8) optionally substituted aroyl,
(9) optionally substituted aryl,
(10) optionally substituted $C_3$–$C_7$ cycloalkanoyl,
(11) optionally substituted $C_5$–$C_7$ cycloalkenoyl,
(12) optionally substituted $C_1$–$C_{10}$ alkylsulfonyl
(13) optionally substituted $C_3$–$C_8$ cycloalkyl
(14) optionally substituted $C_5$–$C_8$ cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, $C_1$–$C_6$ alkoxy, $C_3$–$C_7$ cycloalkyl, aryl $C_1$–$C_3$ alkoxy, $NR^gR^h$, $CO_2R^b$, $CONR^cR^d$ and halogen,
(15) $C_1$–$C_5$ perfluoroalkyl,
(16) arylsulfonyl optionally substituted with 1 to 3 groups independently selected from $C_1$–$C_5$ alkyl, $C_1$–$C_5$ perfluoroalkyl, nitro, halogen and cyano,
(17) a 5-membered heterocycle containing 1 heteroatom selected from oxygen, sulfur and nitrogen optionally substituted by 1 to 4 groups independently selected from $C_1$–$C_5$ alkyl, $C_1$–$C_5$ alkenyl, $C_1$–$C_5$ perfluoroalkyl, amino, $C(O)NR^cR^d$, cyano, $CO_2R^b$ and halogen, and which may be saturated or partly unsaturated;

$R^b$ is (1) hydrogen,
(2) optionally substituted aryl,
(3) optionally substituted $C_1$–$C_{10}$ alkyl,
(4) optionally substituted $C_3$–$C_{10}$ alkenyl,
(5) optionally substituted $C_3$–$C_{10}$ alkynyl,
(6) optionally substituted $C_3$–$C_{15}$ cycloalkyl,
(7) optionally substituted $C_5$–$C_{10}$ cycloalkenyl, or
(8) optionally substituted 5-membered heterocycle containing 1 heteroatom selected from oxygen, sulfur and nitrogen; where the substituents on the aryl, alkyl, alkenyl, cycloalkyl, cycloalkenyl, heterocycle, or alkynyl are from 1 to 10 groups independently selected from
(i) hydroxy,
(ii) $C_1$–$C_6$ alkyl,
(iii) oxo,
(iv) $SO_2NR^gR^h$,
(v) aryl $C_1$–$C_6$ alkoxy,
(vi) hydroxy $C_1$–$C_6$ alkyl,
(vii) $C_1$–$C_{12}$ alkoxy,
(viii) hydroxy $C_1$–$C_6$ alkoxy,
(ix) amino $C_1$–$C_6$ alkoxy,
(x) cyano,
(xi) mercapto,
(xii) $C_1$–$C_6$ alkyl-S(O)m,
(xiii) $C_3$–$C_7$ cycloalkyl optionally substituted with 1 to 4 groups independently selected from $R^e$,
(xiv) $C_5$–$C_7$ cycloalkenyl,
(xv) halogen,
(xvi) $C_1$–$C_5$ alkanoyloxy,
(xvii) $C(O)NR^gR^h$,
(xviii) $CO_2R^i$,
(xix) formyl,
(xx) —$NR^gR^h$,
(xxi) 5-membered heterocycle, which may be saturated or partially unsaturated, containing 1 heteroatom selected from oxygen, sulfur and nitrogen, and optionally substituted with 1 to 5 groups independently selected from $R^e$,
(xxii) optionally substituted aryl, wherein the aryl substituents are 1,2-methylenedioxy or 1 to 5 groups independently selected from $R^e$,
(xxiii) optionally substituted aryl $C_1$–$C_3$ alkoxy, wherein the aryl substituents are 1,2-methylenedioxy or 1 to 5 groups independently selected from $R^e$, and
(xxiv) $C_1$–$C_5$ perfluoroalkyl;

$R^c$ and $R^d$ are independently selected from $R^b$; or $R^c$ and $R^d$ together with the N to which they are attached form a 5-membered ring containing 0 additional heteroatom, optionally substituted with 1 to 3 groups independently selected from $R^g$, hydroxy, thioxo and oxo;

$R^e$ is (1) halogen,
(2) $C_1$–$C_7$ alkyl,
(3) $C_1$–$C_3$ perfluoroalkyl,
(4) —$S(O)_mR^i$,
(5) cyano,
(6) nitro,
(7) $R^iO(CH_2)_v$—,
(8) $R^iCO_2(CH_2)_v$—,
(9) $R^iOCO(CH_2)_v$,
(10) optionally substituted aryl where the substituents are from 1 to 3 of halogen, $C_1$–$C_6$ alkyl, $C_1$–$C_6$ alkoxy, or hydroxy,
(11) $SO_2NR^gR^h$, or
(12) amino;

$R^f$ is (1) $C_1$–$C_4$ alkyl,
(2) X—$C_1$–$C_4$ alkyl, where X is O or $S(O)_m$,
(3) $C_2$–$C_4$ alkenyl,
(4) $C_2$–$C_4$ alkynyl,
(5) $C_1$–$C_3$-perfluoroalkyl,
(6) $NY^1Y^2$, where $Y^1$ and $Y^2$ are independently H or $C_1$–$C_5$ alkyl,
(7) hydroxy,
(8) halogen, and
(9) $C_1$–$C_5$ alkanoyl amino, $R^g$ and $R^h$ are independently
(1) hydrogen,
(2) $C_1$–$C_6$ alkyl optionally substituted with hydroxy, amino, or $CO_2R^i$
(3) aryl optionally substituted with halogen, 1,2-methylenedioxy, $C_1$–$C_7$ alkoxy, $C_1$–$C_7$ alkyl or $C_1$–$C_3$ perfluoroalkyl,
(4) aryl $C_1$–$C_6$ alkyl, wherein the aryl is optionally substituted with $C_1$–$C_3$ perfluorolkyl or 1,2-methylenedioxy;
(5) $C_1$–$C_5$ alkoxycarbonyl,
(6) $C_1$–$C_5$ alkanoyl,
(7) $C_1$–$C_5$ alkanoyl $C_1$–$C_6$ alkyl,
(9) aryl $C_1$–$C_5$ alkoxycarbonyl,
(10) aminocarbonyl,
(11) $C_1$–$C_5$ monoalkylaminocarbonyl

(12) $C_1-C_5$ dialkylaminocarbonyl; or $R^g$ and $R^h$ together with the N to which they are attached form a 5-membered ring containing 0 additional heteroatom, optionally substituted with 1 to 3 groups independently selected from $R^e$ and oxo;

$R^i$ is (1) hydrogen,
(2) $C_1-C_3$ perfluoroalkyl,
(3) $C_1-C_6$ alkyl,
(4) optionally substituted aryl $C_0-C_6$ alkyl, where the aryl substituents are from 1 to 3 groups independently selected from halogen, $C_1-C_6$ alkyl, $C_1-C_6$ alkoxy, and hydroxy;

m is 0 to 2; and v is 0 to 3; and a pharmaceutically acceptable salt thereof; and excluding nodulisporic acid, 29,30-dihydro-20,30-oxa-nodulisporic acid, and 3s1-hydroxy-20,30-oxa-29,30, 31,32-tetrahydro-nodulisporic acid.

2. A compound of claim 1 wherein $R^i$ is (1) hydrogen,
(2) optionally substituted $C_1-C_6$ alkyl,
(3) optionally substituted $C_2-C_6$ alkenyl,
(4) optionally substituted $C_2-C_6$ alkynyl,
(5) optionally substituted $C_5-C_6$ cycloalkyl,
(6) optionally substitute d $C_5-C_6$ cycloalkenyl where the substitutents on the alkyl, alkenyl, alkynyl, cycloalkyl and cycloalkenyl are 1 to 3 groups independently selected from
(i) $C_1-C_3$ alkyl,
(ii) X—$C_1-C_6$ alkyl, where X is O or $S(O)_m$,
(iii) $C_5-C_6$ cycloalkyl,
(iv) hydroxy,
(v) halogen,
(vi) cyano,
(vii) carboxy, and
(viii) $NY^1Y^2$, where $Y^1$ and $Y^2$ are independently hydrogen or $C_1-C_6$ alkyl,
(7) aryl $C_0-C_3$ alkyl wherein said aryl is optionally substituted with 1 to 3 groups independently selected from $R^f$,
(8) $C_1-C_3$ perfluoroalkyl,
(9) a 5-membered heterocycle containing heteroatom selected from oxygen, sulfur and nitrogen atoms optionally substituted by 1 to 3 groups independently selected from hydroxy, oxo, $C_1-C_6$ alkyl and halogen, and which may be saturated or partly unsaturated, $R_8$ is (1) hydrogen,
(2) OH, or
(3) $NH_2$;

$R^g$ is (1) hydrogen or
(2) OH;

$R_{10}$ is (1) $C(O)OR^b$,
(2) $C(O)N(OR^b)R^c$,
(3) $C(O)NR^cR^d$,
(4) $NHC(O)OR^b$,
(5) $NHC(O)NR^cR^d$,
(6) $CH_2OR^a$, (
7) $CH_2OCO_2R^b$,
(8) $CH_2OC(O)NR^cR^d$,
(9) $C(O)NR^cNR^cR^d$, or
(10) $C(O)NR^cSO_2R^b$;

$R^a$ is (1) hydrogen,
(2) optionally substituted $C_1-C_6$ alkyl,
(3) optionally substituted $C_3-C_6$ alkenyl,
(4) optionally substituted $C_3-C_6$ alkynyl,
(5) optionally substituted $C_1-C_6$ alkanoyl,
(6) optionally substituted $C_3-C_6$ alkenoyl,
(7) optionally substituted $C_3-C_6$ alkynoyl,
(8) optionally substituted aroyl,
(9) optionally substituted aryl,
(10) optionally substituted $C_5-C_6$ cycloalkanoyl,
(11) optionally substituted $C_5-C_6$ cycloalkenoyl,
(12) optionally substituted $C_1-C_6$ alkylsulfonyl
(13) optionally substituted $C_5-C_6$ cycloalkyl
(14) optionally substituted $C_5-C_6$ cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, $C_1-C_4$ alkoxy, $C_5-C_6$ cycloalkyl, aryl $C_1-C_3$ alkoxy, $NR^gR^h$, $CO_2R^b$, $CONR^cR^d$ and halogen,
(15) $C_1-C_3$ perfluoroalkyl,
(16) arylsulfonyl optionally substituted with 1 to 3 groups independently selected from $C_1-C_3$ alkyl, $C_1-C_3$ perfluoroalkyl, halogen and cyano,
(17) a 5-membered heterocycle containing 1 heteroatom selected from oxygen, sulfur and nitrogen optionally substituted by 1 to 4 groups independently selected from $C_1-C_3$ alkyl, $C_1-C_3$ alkenyl, $C_1-C_3$ perfluoroalkyl, amino, $C(O)NR^cR^d$, cyano, $CO_2R^b$ and halogen, and which may be saturated or partly unsaturated;

$R^b$ is (1) hydrogen,
(2) optionally substituted aryl,
(3) optionally substituted $C_1-C_7$ alkyl,
(4) optionally substituted $C_3-C_7$ alkenyl,
(5) optionally substituted $C_3-C_7$ alkynyl,
(6) optionally substituted $C_5-C_7$ cycloalkyl,
(7) optionally substituted $C_5-C_7$ cycloalkenyl, or
(8) optionally substituted 5-membered heterocycle containing 1 heteroatom selected from oxygen, sulfur and nitrogen; where the substituents on the aryl, alkyl, alkenyl, cycloalkyl, cycloalkenyl, heterocycle, or alkynyl are from 1 to 10 groups independently selected from
(i) hydroxy,
(ii) $C_1-C_3$ alkyl,
(iii) oxo,
(iv) $SO_2NR^gR^h$,
(v) aryl $C_1-C_3$ alkoxy,
(vi) hydroxy $C_1-C_3$ alkyl,
(vii) $C_1-C_7$ alkoxy,
(viii) hydroxy $C_1-C_3$ alkoxy,
(ix) amino $C_1-C_3$ alkoxy,
(x) cyano,
(xi) $C_1-C_3$ perfluoroalkyl,
(xii) $C_1-C_3$ alkyl-S(O)m,
(xiii) $C_5-C_6$ cycloalkyl optionally substituted with 1 to 4 groups independently selected from $R^e$,
(xiv) $C_5-C_6$ cycloalkenyl,
(xv) halogen,
(xvi) $C_1-C_3$ alkanoyloxy,
(xvii) $C(O)NR^gR^h$,
(xviii) $CO_2R^i$,
(xix) optionally substituted aryl $C_1-C_3$ alkoxy, wherein the aryl substituents are 1,2-methylenedioxy or 1 to 5 groups independently selected from $R^e$,
(xx) —$NR^gR^h$,
(xxi) 5-membered heterocycle, which may be saturated or partially unsaturated, containing 1 heteroatom selected from oxygen, sulfur and nitrogen, and optionally substituted with 1 to 5 groups independently selected from $R^e$, and (xxii) optionally substituted aryl, wherein the aryl substituents are 1,2-methylenedioxy or 1 to 5 groups independently selected from $R^e$;

$R^e$ is (1) halogen,
(2) $C_1$–$C_3$ alkyl,
(3) $C_1$–$C_3$ perfluoroalkyl,
(4) —$S(O)_m R^i$,
(5) cyano,
(6) amino,
(7) $R^i O(CH_2)_v$—,
(8) $R^i CO_2(CH_2)_v$—,
(9) $R^i OCO(CH_2)_v$,
(10) optionally substituted aryl where the substituents are from 1 to 3 of halogen, $C_1$–$C_3$ alkyl, $C_1$–$C_3$ alkoxy, or hydroxy, or
(11) $SO_2 NR^g R^h$;

$R^f$ is (1) methyl,
(2) X—$C_1$–$C_2$ alkyl, where X is O or $S(O)_m$,
(3) halogen,
(4) acetylamino,
(5) trifluoromethyl,
(6) $NY^1 Y^2$, where $Y^1$ and $Y^2$ are independently H or methyl, and
(7) hydroxy;

$R^g$ and $R^h$ are independently
(1) hydrogen,
(2) $C_1$–$C_6$ alkyl optionally substituted with hydroxy, amino, or $CO_2 R^i$
(3) aryl optionally substituted with halogen, 1,2-methylenedioxy, $C_1$–$C_7$ alkoxy, $C_1$–$C_7$ alkyl or $C_1$–$C_3$ perfluoroalkyl,
(4) aryl $C_1$–$C_6$ alkyl, wherein the aryl is optionally substituted with $C_1$–$C_3$ perfluorolkyl or 1,2-methylenedioxy;
(5) $C_1$–$C_5$ alkoxycarbonyl,
(6) $C_1$–$C_5$ alkanoyl,
(7) $C_1$–$C_5$ alkanoyl $C_1$–$C_6$ alkyl,
(9) aryl $C_1$–$C_5$ alkoxycarbonyl,
(10) aminocarbonyl,
(11) $C_1$–$C_5$ monoalkylaminocarbonyl
(12) $C_1$–$C_5$ dialkylaminocarbonyl; or $R^g$ and $R^h$ together with the N to which they are attached form a 5-membered ring containing 0 additional heteroatom, optionally substituted with 1 to 3 groups independently selected from $R^e$ and oxo;

$R^i$ is (1) hydrogen,
(2) $C_1$–$C_3$ perfluoroalkyl,
(3) $C_1$–$C_4$ alkyl,
(4) optionally substituted aryl $C_0$–$C_4$ alkyl, where the aryl substituents are from 1 to 3 groups independently selected from halogen, $C_1$–$C_4$ alkyl, $C_1$–$C_4$ alkoxy, and hydroxy;

all other variables are as defined in claim 1.

3. A compound of claim 1 wherein $R_1$ is (1) hydrogen,
(2) optionally substituted $C_1$–$C_3$ alkyl,
(3) optionally substituted $C_2$–$C_3$ alkenyl,
(4) optionally substituted $C_2$–$C_3$ alkynyl, where the substitutents on the alkyl, alkenyl, and alkynyl are 1 to 3 groups independently selected from
(i) methyl,
(ii) X-methyl, where X is O or S(O)m and
(iii) halogen,
(5) aryl $C_0$–$C_1$ alkyl wherein said aryl is optionally substituted with 1 to 3 groups independently selected from $R^f$,
(6) trifluoromethyl $R_8$ is (1) hydrogen,
(2) OH, or
(3) $NH_2$ $R^g$ is (1) hydrogen, or
(2) OH;

$R_{10}$ is (1) $C(O)OR^b$,
(2) $C(O)N(OR^b)R^c$,
(3) $C(O)NR^c R^d$,
(4) $NHC(O)OR^b$,
(5) $NHC(O)NR^c R^d$,
(6) $CH_2 OR^a$,
(7) $CH_2 OCO_2 R^b$,
(8) $CH_2 OC(O)NR^c R^d$,
(9) $C(O)NR^c NR^c R^d$, or
(10) $C(O)NR^c SO_2 R^b$;

$R^a$ is (1) hydrogen,
(2) optionally substituted $C_1$–$C_4$ alkyl,
(3) optionally substituted $C_3$–$C_4$ alkenyl,
(4) optionally substituted $C_3$–$C_4$ alkynyl,
(5) optionally substituted $C_1$–$C_4$ alkanoyl,
(6) optionally substituted aroyl,
(7) optionally substituted $C_5$–$C_6$ cycloalkanoyl,
(8) optionally substituted $C_5$–$C_6$ cycloalkenoyl,
(9) optionally substituted $C_1$–$C_3$ alkylsulfonyl where the substituents on the alkyl, alkenyl, alkynyl, alkanoyl, aroyl, cycloalkanoyl, cycloalkenoyl, and alkylsulfonyl, are from 1 to 5 groups independently selected from hydroxy, $C_1$–$C_2$ alkoxy, aryl $C_1$–$C_3$ alkoxy, $NR^g R^h$, $CO_2 R^b$, $CONR^c R^d$ and halogen,
(10) trifluoromethyl,
(11) arylsulfonyl optionally substituted with 1 to 3 groups independently selected from methyl, trifluoromethyl and halogen,
(12) a 5-membered heterocycle containing 1 heteroatom selected from oxygen, sulfur and nitrogen optionally substituted by 1 to 4 groups independently selected from methyl, trifluoromethyl, $C(O)NR^c R^d$, $CO_2 R^b$ and halogen, and which may be saturated or partly unsaturated;

$R^b$ is (1) hydrogen,
(2) optionally substituted aryl,
(3) optionally substituted $C_1$–$C_6$ alkyl,
(4) optionally substituted $C_3$–$C_6$ alkenyl,
(5) optionally substituted $C_3$–$C_6$ alkynyl,
(6) optionally substituted $C_5$–$C_6$ cycloalkyl,
(7) optionally substituted $C_5$–$C_6$ cycloalkenyl, or
(8) optionally substituted 5-membered heterocycle containing 1 heteroatom selected from oxygen, sulfur and nitrogen;

where the substituents on the aryl, alkyl, alkenyl, cycloalkyl, cycloalkenyl, heterocycle, or alkynyl are from 1 to 10 groups independently selected from
(i) hydroxy,
(ii) $C_1$–$C_3$ alkyl,
(iii) oxo,
(iv) $SO_2 NR^g R^h$,
(v) aryl $C_1$–$C_3$ alkoxy, (vi) hydroxy $C_1$–$C_4$ alkyl,
(vii) $C_1$–$C_4$ alkoxy,
(viii) hydroxy $C_1$–$C_4$ alkoxy,
(ix) amino $C_1$–$C_4$ alkoxy,
(x) cyano,
(xi) $C_1$–$C_4$ alkyl-S(O)m,
(xii) $C_5$–$C_6$ cycloalkyl optionally substituted with 1 to 4 groups independently selected from $R^e$,
(xiii) $C_5$–$C_6$ cycloalkenyl,
(xiv) halogen,
(xv) $C_1$–$C_3$ alkanoyloxy,
(xvi) $C(O)NR^gR^h$,
(xvii) $CO_2R^i$,
(xvii) —$NR^gR^h$
(xix) 5-membered heterocycle, which may be saturated or partially unsaturated, containing 1 heteroatom selected from oxygen, sulfur and nitrogen, and optionally substituted with 1 to 5 groups independently selected from $R^e$,
(xx) optionally substituted aryl, wherein the aryl substituents are 1,2-methylenedioxy or 1 to 5 groups independently selected from $R^e$,
(xxi) optionally substituted aryl $C_1$–$C_3$ alkoxy, wherein the aryl substituents are 1,2-methylenedioxy or 1 to 5 groups independently selected from $R^e$, and
(xxii) $C_1$–$C_3$ perfluoroalkyl;
$R^e$ is (1) halogen,
(2) $C_1$–$C_3$ alkyl,
(3) $C_1$–$C_3$ perfluoroalkyl,
(4) —$S(O)_mR^i$,
(5) cyano,
(6) $R^iO(CH_2)_v$—,
(7) $R^iCO_2(CH_2)_v$—,
(8) $R^iOCO(CH_2)_v$,
(9) optionally substituted aryl where the substituents are from 1 to 3 of halogen, $C_1$–$C_3$ alkyl, $C_1$–$C_3$ alkoxy, or hydroxy,
(10) $SO_2NR^gR^h$, or
(11) amino;
$R^f$ is (1) methyl,
(2) X—$C_1$–$C_2$ alkyl, where X is O or $S(O)_m$,
(3) trifluoromethyl,
(4) $NY^1Y^2$, where $Y^1$ and $Y^2$ are independently H or methyl,
(5) hydroxy,
(6) halogen, and
(7) acetylamino,
$R^g$ and $R^h$ are independently
(1) hydrogen,
(2) $C_1$–$C_6$ alkyl optionally substituted with hydroxy, amino, or $CO_2R^i$
(3) aryl optionally substituted with halogen, 1,2-methylenedioxy, $C_1$–$C_7$ alkoxy, $C_1$–$C_7$ alkyl or $C_1$–$C_3$ perfluoroalkyl,
(4) aryl $C_1$–$C_6$ alkyl, wherein the aryl is optionally substituted with $C_1$–$C_3$ perfluorolkyl or 1,2-methylenedioxy;
(5) $C_1$–$C_5$ alkoxycarbonyl,
(6) $C_1$–$C_5$ alkanoyl,
(7) $C_1$–$C_5$ alkanoyl $C_1$–$C_6$ alkyl,
(9) aryl $C_1$–$C_5$ alkoxycarbonyl,
(10) aminocarbonyl,
(11) $C_1$–$C_5$ monoalkylaminocarbonyl
(12) $C_1$–$C_5$ dialkylaminocarbonyl; or
$R^g$ and $R^h$ together with the N to which they are attached form a 5-membered ring containing 0 additional heteroatom, optionally substituted with 1 to 3 groups independently selected from $R^e$ and oxo;
$R^i$ is (1) hydrogen,
(2) $C_1$–$C_3$ perfluoroalkyl,
(3) $C_1$–$C_4$ alkyl,
(4) optionally substituted aryl $C_0$–$C_6$ alkyl, where the aryl substituents are from 1 to 3 groups independently selected from halogen, $C_1$–$C_6$ alkyl, $C_1$–$C_6$ alkoxy, and hydroxy all other variables are as defined in claim 1.

4. A compound of claim 1 wherein $R_7$ is CHO.

5. A compound of claim 1 wherein $R_7$ is the fragment $$\begin{array}{c} R_8 \\ \overset{|}{\underset{31}{\diagdown}} R_9 \\ R_{10} \end{array}$$

$R_{10}$ is (1) $C(O)OR^b$,
(2) $C(O)N(OR^b)R^c$,
(3) $C(O)NR^cR^d$,
(4) $C(O)NR^cNR^cR^d$, or
(5) $C(O)NR^cSO_2R^b$
$R_8$, $R_9$, $R^b$, $R^c$ and $R^d$ are as defined in claim 1.

6. A compound of claim 5 wherein
$R_{10}$ is $C(O)OR^b$;
$R^b$ is (1) optionally substituted aryl,
(2) optionally substituted $C_1$–$C_6$ alkyl,
(3) optionally substituted $C_3$–$C_6$ alkenyl,
(4) optionally substituted $C_3$–$C_6$ alkynyl,
(5) optionally substituted $C_3$–$C_6$ cycloalkyl, or
(6) optionally substituted 5-membered heterocycle containing 1 heteroatom selected from oxygen, sulfur and nitrogen;
where the substituents on the aryl, alkyl, alkenyl, cycloalkyl, heterocycle, or alkynyl are from 1 to 10 groups independently selected from
(i) hydroxy,
(ii) $C_1$–$C_3$ alkyl,
(iii) oxo,
(iv) $SO_2NR^gR^h$,
(v) aryl $C_1$–$C_3$ alkoxy,
(vi) hydroxy $C_1$–$C_4$ alkyl,
(vii) $C_1$–$C_4$ alkoxy,
(viii) hydroxy $C_1$–$C_4$ alkoxy,
(ix) amino $C_1$–$C_4$ alkoxy,
(x) cyano,
(xi) $C_1$–$C_4$ alkyl-S(O)m,
(xii) $C_5$–$C_6$ cycloalkyl optionally substituted with 1 to 4 groups independently selected from $R^e$,
(xiii) $C_5$–$C_6$ cycloalkenyl,
(xiv) halogen,
(xv) $C_1$–$C_3$ alkanoyloxy,
(xvi) $C(O)NR^gR^h$,
(xvii) $CO_2R^i$,
(xvii) —$NR^gR^h$,
(xix) 5-membered heterocycle, which may be saturated or partially unsaturated, containing 1 heteroatom selected from oxygen, sulfur and nitrogen, and optionally substituted with 1 to 5 groups independently selected from $R^e$,
(xx) optionally substituted aryl, wherein the aryl substituents are 1,2-methylenedioxy or 1 to 5 groups independently selected from $R^e$,
(xxi) optionally substituted aryl $C_1$–$C_3$ alkoxy, wherein the aryl substituents are 1,2-methylenedioxy or 1 to 4 groups independently selected from $R^e$, and (xxii) $C_1-C_3$ perfluoroalkyl;
$R^e$ is (1) halogen,
(2) $C_1-C_7$ alkyl,
(3) $C_1-C_3$ perfluoroalkyl
(4) nitro,
(6) $R^iO(CH_2)_v$,
(7) $R^iOC(O)(CH_2)_v$,
(8) $SO_2NR^gR^h$,
v is 0;
$R^g$ and $R^h$ are independently
(1) hydrogen,
(2) $C_1-C_6$ alkyl optionally substituted with hydroxy or $CO_2R^b$,
(3) aryl optionally substituted with halogen, 1,2-methylenedioxy, $C_1-C_7$ alkyl or $C_1-C_3$ perfluoroalkyl,
(4) $C_1-C_5$ alkanoyl, or
$R^g$ and $R^h$ together with the N to which they are attached form a 5- membered ring containing 0 additional heteroatom, optionally substituted with 1 to 3 groups independently selected from $R^e$ and oxo;
$R^i$ is (1) hydrogen, or
(2) $C_1-C_6$ alkyl;
m is 0 to 2; and
all other variables are as defined in claim 5.

7. A compound of claim 5 wherein
$R^{10}$ is (1) $C(O)N(OR^b)R^c$,
(2) $C(O)NR^cR^d$
(3) $C(O)NR^cNR^cR^d$, or
(4) $C(O)NR^cSO_2R^i$;
$R^b$, $R^c$, $R^d$ and $R^i$ are as defined in claim 5.

8. A compound of claim 3 wherein
$R^{10}$ is $C(O)NR^cR^d$; and $R_c$ and $R^d$ are as defined in claim 3.

9. A compound of claim 5 wherein
$R_{10}$ is $C(O)NR^cR^d$;
$R^b$ is (1) hydrogen,
(2) optionally substituted aryl,
(3) optionally substituted $C_1-C_6$ alkyl,
(4) optionally substituted $C_3-C_6$ alkenyl,
(5) optionally substituted $C_3-C_6$ alkynyl,
(6) optionally substituted $C_3-C_6$ cycloalkyl,
(7) optionally substituted $C_5-C_6$ cycloalkenyl, or
(8) optionally substituted 5-membered heterocycle containing 1 heteroatom selected from oxygen, sulfur and nitrogen;
where the substituents on the aryl, alkyl, alkenyl, cycloalkyl, cycloalkenyl, heterocycle, or alkynyl are from 1 to 10 groups independently selected from
(i) hydroxy,
(ii) $C_1-C_3$ alkyl,
(iii) oxo,
(iv) $SO_2NR^gR^h$,
(v) aryl$C_1-C_3$ alkyl,
(vi) hydroxy $C_1-C_4$ alkyl,
(vii) $C_1-C_{12}$ alkoxy,
(viii) hydroxy $C_1-C_4$ alkoxy,
(ix) amino $C_1-C_4$ alkoxy,
(x) cyano,
(xi) $C_1-C_3$ perfluoroalkyl,
(xii) $C_1-C_4$alkyl-S(O)$_m$,
(xiii) $C_5-C_6$ cycloalkyl optionally substituted with 1 to 4 groups selected from $R^e$,
(xiv) $C_5-C_6$ cycloalkenyl,
(xv) halogen,
(xvi) $C(O)NR^gR^h$,
(xvii) $CO_2R^i$,
(xviii) —$NR^gR^h$,
(xix) 5-membered heterocycle containing 1 heteroatom selected from oxygen, sulfur and nitrogen, and optionally substituted with 1 to 3 groups independently selected from $R^e$,
(xx) optionally substituted aryl, wherein the aryl substituents are 1,2-methylenedioxy or 1 to 5 groups independently selected from $R^e$ and
(xxi) optionally substituted aryl $C_1-C_3$ alkoxy, wherein the aryl substituents are 1,2-methylenedioxy or 1 to 5 groups independently selected from $R^e$;
$R^c$ and $R^d$ are independently selected from $R^b$; or
$R^c$ and $R^d$ together with the N to which they are attached form a 1 membered ring containing 0 additional heteratom, optionally substituted with 1 to 3 groups independently selected from $R^g$, hydroxy, thioxo and oxo;
$R^e$ is (1) halogen,
(2) $C_1-C_3$ alkyl,
(3) $C_1-C_3$ perfluoroalkyl,
(4) $R^iO(CH_2)_v$—,
(5) $R^{ji}CO_2(CH_2)_v$,
(6) $R^iOCO(CH_2)_v$,
(7) $SO_2NR^gR^h$;
(8) amino
v is 0;
$R^g$ and $R^h$ are independently
(1) hydrogen,
(2) $C_1-C_6$ alkyl optionally substituted with hydroxy, amino, or $CO_2R^i$,
(3) aryl optionally substituted with halogen, 1,2-methylenedioxy, $C_1-C_7$ alkoxy, $C_1-C_7$ alkyl or $C_1-C_3$ perfluoroalkyl,
(4) aryl $C_1-C_6$ alkyl, wherein the aryl is optionally substituted with $C_1-C_3$ perfluoroalkyl or 1,2-methylenedioxy,
(5) $C_1-C_5$ alkoxycarbonyl,
(6) $C_1-C_5$ alkanoyl,
(7) aryl $C_1-C_5$ alkoxycarbonyl,
(8) aminocarbonyl, or
$R^g$ and $R^h$ together with the N to which they are attached form a 5-membered ring containing 0 additional heteroatom, optionally substituted with 1 to 3 groups independently selected from $R^e$ and oxo;
$R^i$ is (1) hydrogen or
(2) optionally substituted $C_0-C_6$ alkyl wherein the substituents are aryl or substituted aryl, and the aryl substituents are from 1 to 3 groups independently selected from halogen, $C_1-C_6$ alkyl, $C_1-C_6$ alkoxy, and hydroxy; and
all other variables are as defined in claim 5.

10. A compound of claim 1 wherein $R_7$ is the fragment

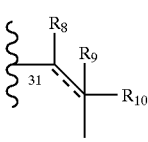

$R_{10}$ is $CH_2OR^a$, $NHC(O)OR^b$ or $NHC(O)NR^cR^d$;
$R_8$, $R_9$, $R^a$, $R^b$, $R^c$, $R^d$ and ---- are as defined in claim 1.

11. A compound of claim 1 wherein $R_7$ is the fragment

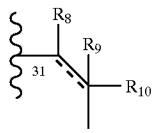

$R_{10}$ is $CO_2H$; and $R_8$, $R_9$ and ---- are as defined in claim 1.

12. A compound of the formula

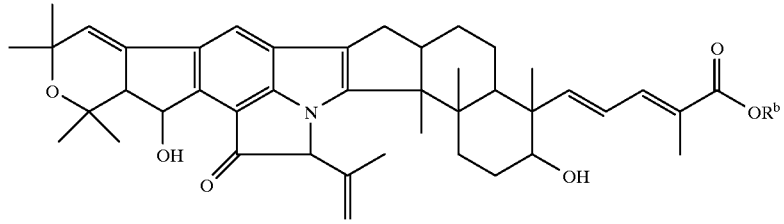

wherein $R^b$ is selected from the group consisting of:
$CH_3$, $CH_2CH_3$, $CH_2CH_2OH$, $CH_2CH_2N(CH(CH_3)_2)_2$, $CH_2CH_2CH_2OH$, $CH_2CH_2CH_2CH_2OH$, $CH_2CH_2CH_2CH_2CH_2OH$, $CH_2CH_2N(CH_3)_2$, $CH_2CH(OH)CH_2N(CH(CH_3)_2)_2$, $CH_2CH_2OCH_2CH_2OH$, $CH_2Ph(4-NO_2)$, $CH_2Ph(3-NO_2)$, $CH_2CF_3$, $CH_2CH_2CH_2C(=O)CH_3$, $CH_2CH_2CH_2Ph$, $CH_2CH_2C(CH_3)_2CH_3$, $CH(CF_3)_2$, $CH_2Ph(2-CF_3)$,

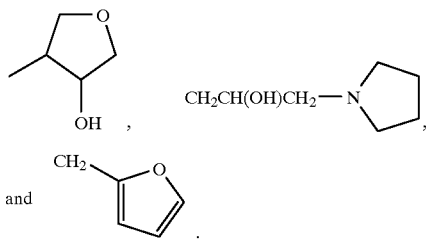

and

13. A compound of the formula

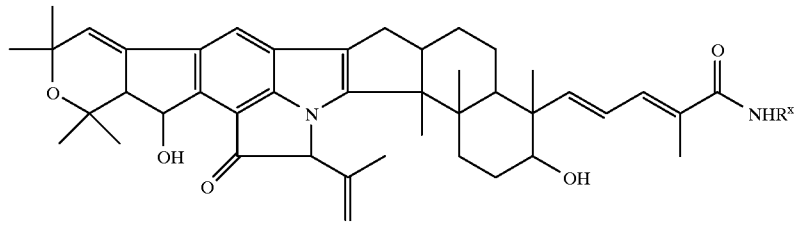

wherein $R^x$ is selected from the group consisting of:
H, $CH_3$, $CH_2CH_3$, $C(CH_3)_3$, $CH_2CH_2CH_3$, $CH_2CH_2OH$, $CH(COCH_3)CH_2OH$, $CH_2CO_2CH_3$, $CH_2CH(OCH_2CH_3)_2$, $CH_2CH_2OCH_2CH_2OH$, $CH(CH_3)(CH_2)_3C(CH_3)_2OH$, $(CH_2)_3OH$, $(CH_2)_4OH$, $(CH_2)_5OH$, $CH(CH_2OH)CH_2CH_3$, $NHC(CH_3)_3$, $CH_2CN$, $(CH_2)_6OH$, $CH_2CH(OH)CH_3$, $CH(CH_2OH)CH_2CH_2CH_3$, $CH_2CH_2SCH_3$, $CH_2CH_2SCH_2CH_3$, $CH_2CONH_2$, $CH(CH_3)(CH_2OH)_2$, $CH_2CH_2NHCH_2CH_2OH$, $CH(CH_2OH)(CH_2)_3CH_3$, $CH(CH_2OCH_3)CH_3$, $(CH_2)$ $_2SH$, $(CH_2)_4NH_2$, $CH_2CH_2SO_2CH_3$, $CH_2CH_2S(O)CH_3$, $CH(CH(CH_3)_2)CH_2OH$, $(CH_2)_3NH_2$, $(CH_2)_3N(CH_2CH_3)_2$, $(CH_2)_3N(CH_3)_2$, $OCH_2CH_3$, $CH_2CH(OH)CH_2OH$, $OCH_3$, $CH_2CH_2OCH_3$, $CH_2CH_2NHC(O)CH_3$, $C(CH_3)_2CH_2OH$, $c-C_3H_5$, $c-C_6H_{11}$, $(CH_2)3OCH_2CH_3$, $CH_2CH=CH_2$, $C(CH_2CH_3)(CH_2OH)_2$, $CH_2C\equiv CH$, $CH_2CO_2CH_2CH_3$, $CH_2CH_2F$, $(CH_2)_3O(CH_2)_{11}CH_3$, $CH_2CH_2N(CH_3)_2$, $CH_2CH_2OCH_2CH_2NH_2$, $CH_2CF_3$, $NHCH_2CO_2CH_2CH_3$, $CH(CH_3)CO_2CH_3$, $C(CH_3)_2CH_2C(O)CH_3$, $CH(CO_2CH_2CH_3)_2$, $CH_2CH_3$, $CH(CH_2CH_2CH_3)CO_2CH_3$, $CH_2CH_2CH_2OCH_3$, $C(CH_3)_2C=CH$, $(CH_2)_4CH_3$, $CH(CH_2CH_2CH_3)_2$, $(CH_2)_5CH_3, CH_2CH_2CO_2H$, $CH(CH(CH_3)_2)CO_2CH_3$, $OCH_2CO_2H$, $CH(CH(CH_3)_2)CH_2OH$, $CH(CH(CH_3)_2)CH_2OH$, $CH(CH_3)CH_2OH$, $CH(CH_3)CH_2OH$, $CH(CH_3)_2$, $C(CH_3)_3$, $(CH_2)CH(CH_3)_2$, $CH(CH_3)CH_2CH_3$, $CH_2CH(CH_3)OH$, $(CH_2)_3CH_3$, $(CH_2)_2OCH_2CH_3$, 1-adamantyl, $(CH_2)_8CH_3$, $CH(CH_3)CH(CH_3)_2$, $(CH_2)_3NHCH_3$, $(CH_2)_2N(CH_2CH_3)_2$,

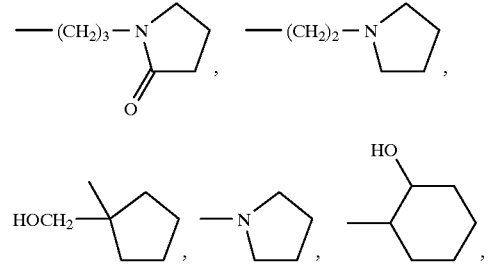

-continued

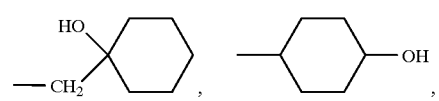

-continued

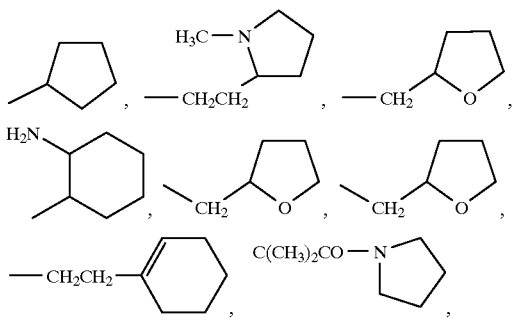

C(CH₃)₂CO₂CH₃, C(CH₃)₂CO₂CH₂CH₃, C(CH₃)₂CON(CH₃)₂, C(CH₃)₂CONHCH₂CF₃, C(CH₃)₂CON(CH₃)CH₂CH₃, CH(CH₂F)₂, C(CH₂F)₂CO₂CH₃, C(CH₃)₂CH₂F.

14. A compound of the formula

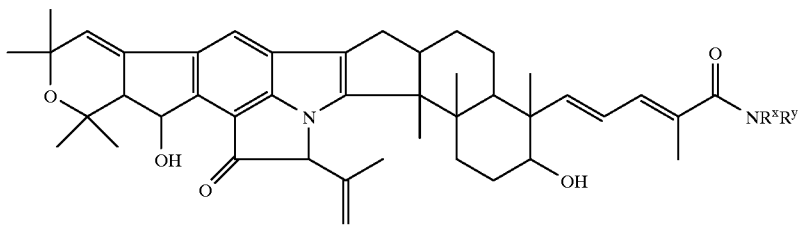

wherein NR$^x$R$^y$ is selected from the group consisting of:
N(CH₃)CH₂C≡N, N(CH₃)CH₂CH₃, N(CH₃)CH(CH₃)₂, N(CH₃)CH₂CH₂CH₃, N(CH₃)CH₂CH₂CH₂CH₃, N(CH₂CH₃)CH₂CH₂OCH₃, N(CH₃)CH₂CH₂OCH₃, N(CH₂CH₃)CH₂CH₂CH₃, N(CH₂CH=CH₂)₂, N(CH₃)CH₂CH₂OH, N(CH₂CH(CH₃)OH)₂, N(CH₂CH₃)₂, N(CH₂CH₂OH)₂, N(CH₂CH₃)CH(CH₃)₂, N(CH₂CH₂CH₂CH₃)₂, N(CH₂CH₂CH₂CH₂CH₃)₂, N(CH₃)₂, N(CH₂CH₂CH₃)₂, N((CH₂)₂CH₃)CH₂CH₂OH, N(CH₃)CH₂C≡CH, N((CH₂)₈CH₃)₂, N((CH₂)₇CH₃)₂, N(CH₃)(CH₂)₂NHCH₃, N(CH₃)(CH₂)₃NH₂, NHCH(CH₂OH)CH₂Ph, NHPh(2-OH,4-CH₃), NHCH₂Ph(4-NH₂), NHPh(4-Cl), NHPh(4-CH₂CH₂OH), NHPh(2-CH₂CH₂OH), NHCH₂CH₂Ph, NHPh(2-CH₂OH), NHPh(3-N(CH₃)₂, NHPh(4-SO₂NH₂), NHNHPh, NHPh(2-CONH₂), NHCH₂CH₂Ph(4-OH), NHCH₂CH₂Ph(4-SO₂NH₂), NHPh(2-NH₂), NHCH(CH₂CH(CH₃)₂)CO₂CH₂Ph, NHSO₂CH₂Ph(4-C(CH₃)₃), NHSO₂CH₂Ph, NHNHPh(2-F), NHCH₂Ph(4-CF₃), NHPh(4-OCH₂Ph), NHPh(4-SCH₃), NHCH(CH₂Ph)CO₂CH₂CH₃, NHCH(CH₂Ph)CO₂CH₃, NHCH₂Ph(4-OCH₃), NHCH₂-1-naphthyl, NHPh(4-F), NHCH₂Ph(2-F), NHCH₂CH(Ph)OH, NHCH₂CH₂Ph(4-F), NHC(CH₃)₂CH₂Ph(3-F), NHPh(3,4-diF), NHCH₂Ph(3-CH₃), NHNH(3–CH₃)Ph, NHCH₂Ph(2–Cl), NHCH₂Ph(2,4-diCl), NHNHPh(4–CH₃), NHCH₂Ph(4-Cl), NH(CH₂)₃Ph, NHCH₂CH₂Ph(4-Cl), NHCH₂CH₂N(CH₃)Ph, NHCH₂Ph(3-CF₃), NHCH₂Ph(2-CF₃), NH(CH₂)₄Ph, N(CH₃)CH(CH₃)CH(CH₃)Ph, N(CH₃)CH(CH₃)CH(CH₃)Ph, N(CH₂Ph)(CH₂)₃CH₃, NHOCH₂Ph, NCH₂Ph(2,6-diF), N(CH₃)CH(CH₃)Ph, NHCH(CH₃)Ph, N(CH₃)CH₂Ph, NHCH₂Ph(3,4-diCl), N(CH₃)CH(CH₃)Ph, N(CH₂Ph)CH₂CH₂Ph, NHNHCH₂Ph, NHCH₂Ph(2,4-diF), NHNHPh(2,5-diCl), NHCH₂Ph(3-F), NHCH(Ph)CH₂Ph, NHCH₂Ph(3,4-diOH), NHCH₂Ph(3,4-diOCH₃), N(CH₃)CH₂Ph, N(CH₂CH₃)CH₂Ph, N(CH₃)CH(CH₃)Ph, NHCH₂CH₂(3-F)Ph, NHCH(CH₂Ph)CH₂OH,

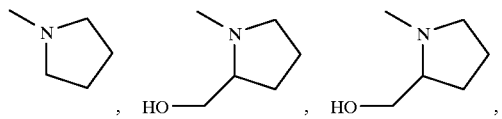

-continued

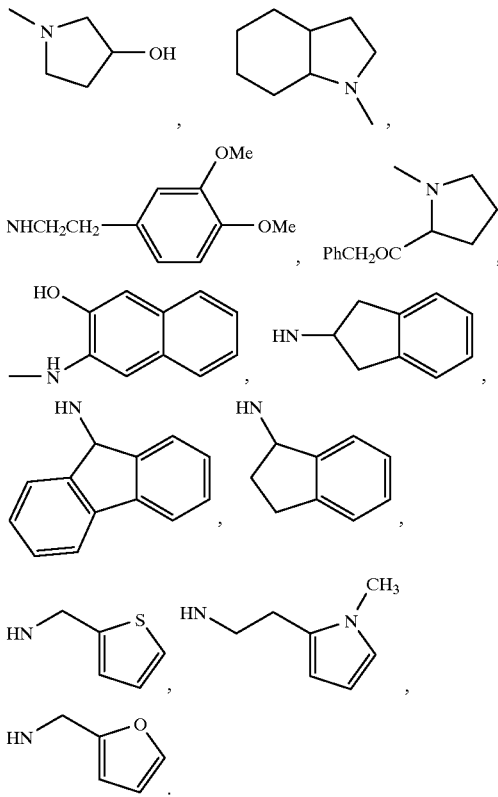

15. A compound having the formula

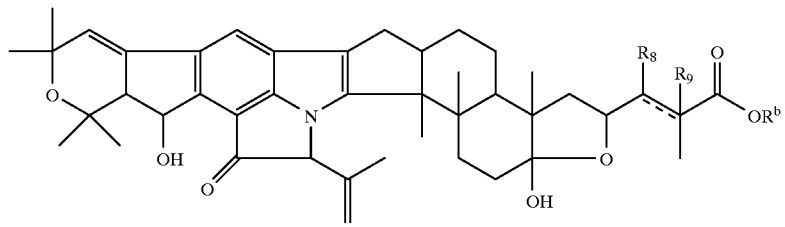

wherein
- $R_8$ and $R_9$ are hydrogen and ---- is a double bond, or
- $R_8$ is hydroxy, $R_9$ is hydrogen and ---- is a single bond; and
- $R^b$ is as defined in claim 12.

16. A compound having the formula

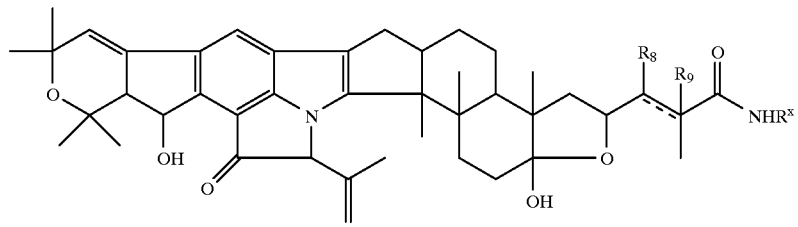

wherein
- $R_8$ and $R_9$ are hydrogen and ---- is a double bond, or
- $R_8$ is hydroxy, $R_9$ is hydrogen and ---- is a single bond; and
- $R^x$ is as defined in claim 13.

17. A compound having the formula

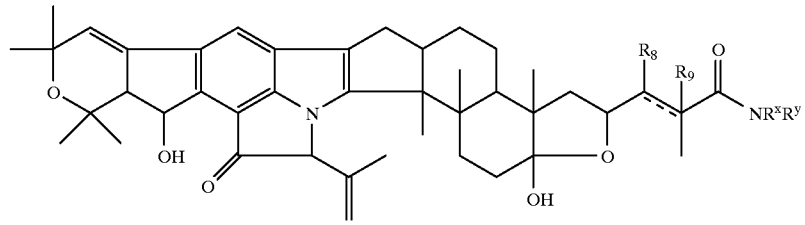

wherein
- $R_8$ and $R_9$ are hydrogen and ---- is a double bond, or
- $R_8$ is hydroxy, $R_9$ is hydrogen and ---- is a single bond; and
- $R^x$ and $R^y$ are as defined in claim 14.

18. A compound having the formula

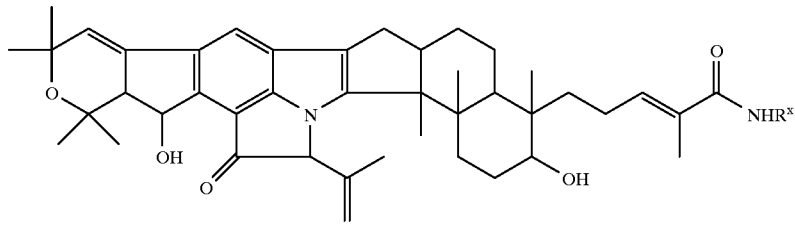

wherein R$^x$ is as defined in claim 13.
19. A compound having the formula
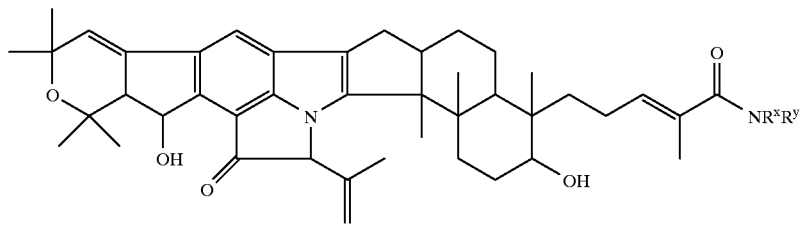
wherein NR$^x$R$^y$ is as defined in claim 14.
20. A compound having the formula
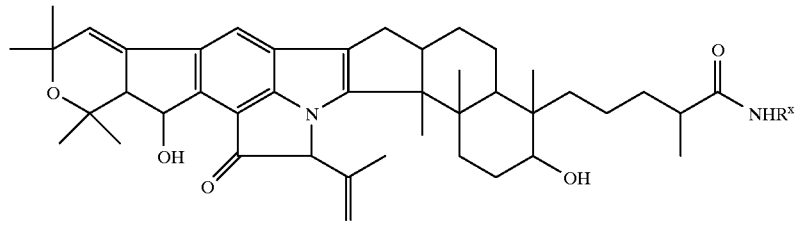
wherein R$^x$ is as defined listed in claim 13.
21. A compound having the formula
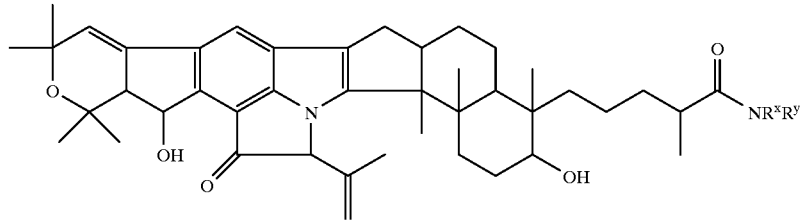
wherein NR$^x$R$^y$ is as defined in claim 14.
22. A compound having the formula
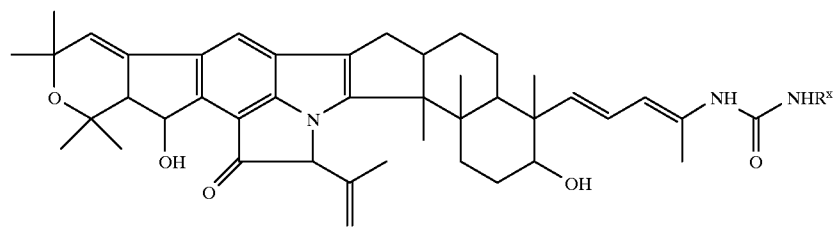
wherein R$^x$ is as defined listed in claim 13.
23. A compound having the formula

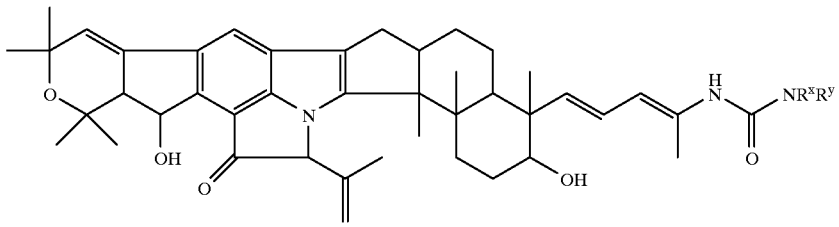

wherein $NR^xR^y$ is as defined in claim 14.

24. A compound having the formula

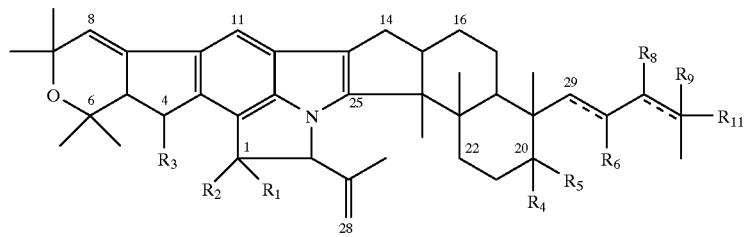

where $R_1$–$R_6$, $R_8$ and $R_9$ are as defined in claim 1;

$R_{11}$ is (1) COCl,
(2) $CON_3$, or
(3) NCO.

25. A pharmaceutical composition comprising a compound of claim 1 and a pharmaceutically acceptable carrier.

26. A composition of claim 25 further comprising an anthelmintic agent.

27. A composition of claim 26 wherein said anthelmintic agent is selected from the group consisting of: ivermectin, avermectin 5-oxime, abamectin, emamectin, eprinamectin, doramectin, doramectin monosaccharide 5-oximes, fulladectin, milbemycin, milbamycin 5-oxime, moxidectin, Interceptor™, nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

28. A composition of claim 25 further comprising fipronil, imidacloprid, lufenuron or an ecdysone agonist.

29. A method for the treatment or prevention of a parasitic disease caused by an arthropod parasite in a mammal which comprises administering to said mammal an antiparasitic effective amount of a compound of claim 1.

30. A method of claim 29 further comprising administering an anthelmintic agent.

31. A method of claim 29 further comprising administering fipronil, imidacloprid or lufenuron.

* * * * *